United States Patent
Chatre et al.

(10) Patent No.: US 11,287,433 B2
(45) Date of Patent: Mar. 29, 2022

(54) METHODS FOR IN VITRO INVESTIGATING MITOCHONDRIAL REPLICATION DYSFUNCTION IN A BIOLOGICAL SAMPLE, KITS AND USES THEREOF, THERAPEUTIC METHODS AGAINST PROGEROID-LIKE SYNDROMES OR SYMPTOMS AND SCREENING METHOD FOR IDENTIFYING PARTICULAR PROTEASE INHIBITOR(S) AND/OR NITROSO-REDOX STRESS SCAVENGER COMPOUND(S)

(71) Applicants: INSTITUT PASTEUR, Paris (FR); CENTRE NATIONAL DE LA RECHERCHE SCIENTIFIQUE, Paris (FR); COMMISSARIAT A L'ENERGIE ATOMIQUE ET AUX ENERGIES ALTERNATIVES, Paris (FR)

(72) Inventors: Laurent Arnaud Chatre, Saint Gratien (FR); Miria Ricchetti, Paris (FR); Alain Sarasin, Thiais (FR); Denis Biard, Thiais (FR)

(73) Assignees: INSTITUT PASTEUR, Paris (FR); CENTRE NATIONAL DE LA RECHERCHE SCIENTIFIQUE, Paris (FR); COMMISSARIAT A L'ENERGIE ATOMIOUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 16/447,890

(22) Filed: Jun. 20, 2019

(65) Prior Publication Data

US 2020/0049718 A1 Feb. 13, 2020

Related U.S. Application Data

(63) Continuation of application No. 15/118,333, filed as application No. PCT/EP2015/053167 on Feb. 13, 2015, now Pat. No. 10,338,082.

(30) Foreign Application Priority Data

Feb. 14, 2014 (EP) .................................... 14305203

(51) Int. Cl.
 C12Q 1/68       (2018.01)
 G01N 33/68      (2006.01)
 C12Q 1/6883     (2018.01)

(52) U.S. Cl.
 CPC ....... *G01N 33/6893* (2013.01); *C12Q 1/6883* (2013.01); *G01N 33/6872* (2013.01);
 (Continued)

(58) Field of Classification Search
 CPC ...................................................... C12Q 1/68
 (Continued)

(56) References Cited

U.S. PATENT DOCUMENTS

2006/0212954 A1  9/2006  Rolla
2007/0277251 A1  11/2007 Wartiovaara
(Continued)

FOREIGN PATENT DOCUMENTS

DE  102007024382 A1  11/2008
KR  20100079360 A    7/2010
(Continued)

OTHER PUBLICATIONS

Lynne Wolfe, Mitochondrial Disease, INS National Meeting, May 18, 2013, published Apr. 30, 2013.*
(Continued)

*Primary Examiner* — Aaron A Priest
(74) *Attorney, Agent, or Firm* — Arrigo, Lee, Guttman & Mouta-Bellum LLP

(57) ABSTRACT

The invention relates to a method for in vitro investigating mitochondrial replication dysfunction in a biological sample removed from a subject susceptible of suffering from physi-
(Continued)

Figure 1A:
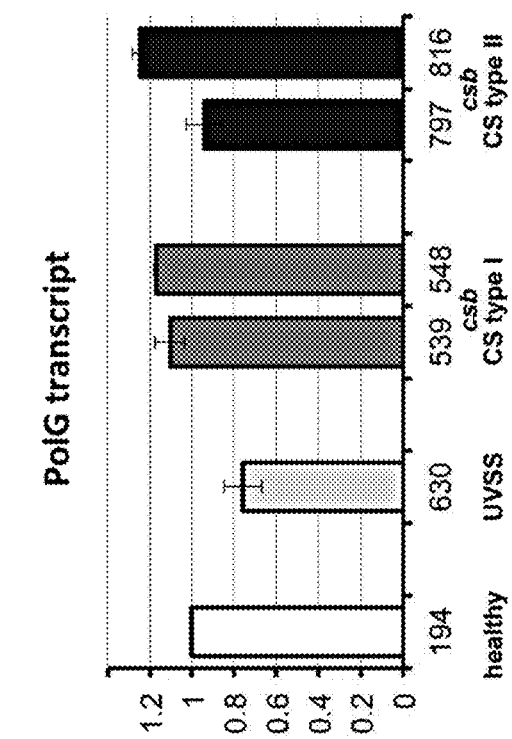
Figure 1B:
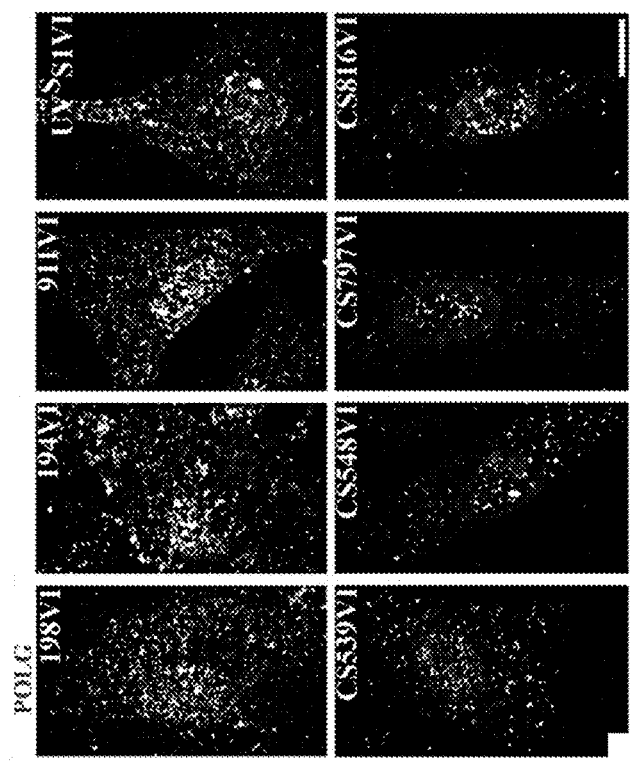
Figure 1C:
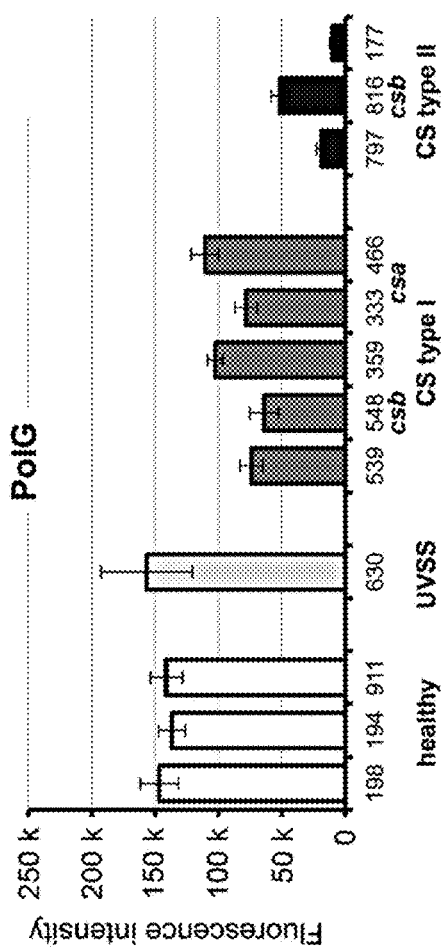
Figure 1D:
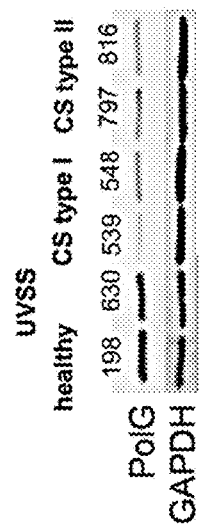

ological ageing or physiopathological conditions related to physiological ageing, or physiopathological ageing or associated symptoms or conditions, in particular premature ageing or accelerated ageing, or of a progeroid syndrome, such as Cockayne syndrome (CS), or neurodegenerative disorders or symptoms thereof, in which the levels of at least one species selected in the group of: POLG1 protein, POLG1 RNA, POLG2 protein, protease(s) which have POLG as a target, in particular serine protease(s) such as HTRA3 protein, HTRA2 protein and, HTRA3 RNA or HTRA2 RNA, or any combination of these species, are investigated. The invention also relates to kits and uses thereof, therapeutic methods against progeroid-like syndromes or symptoms and screening method for identifying particular protease inhibitor(s) and/or nitroso-redox stress scavenger compound(s) having relevance for the symptoms discussed herein.

8 Claims, 14 Drawing Sheets

Specification includes a Sequence Listing.

(52) U.S. Cl.
CPC .......... *C12Q 2600/158* (2013.01); *G01N 2333/9126* (2013.01); *G01N 2333/96411* (2013.01); *G01N 2333/96433* (2013.01); *G01N 2800/04* (2013.01); *G01N 2800/2821* (2013.01); *G01N 2800/2835* (2013.01); *G01N 2800/7009* (2013.01); *G01N 2800/7042* (2013.01)

(58) Field of Classification Search
USPC .............................................. 435/6
See application file for complete search history.

(56) References Cited

U.S. PATENT DOCUMENTS

| 2010/0130597 | A1  | 5/2010  | Hung    |           |
|--------------|-----|---------|---------|-----------|
| 2011/0008310 | A1  | 1/2011  | Cataldo |           |
| 2011/0071049 | A1  | 3/2011  | Heintz  |           |
| 2012/0010178 | A1* | 1/2012  | Rubin   | A61P 25/28 |
|              |     |         |         | 514/158   |
| 2012/0164243 | A1  | 6/2012  | Rinsch  |           |
| 2015/0065556 | A1  | 3/2015  | Birsoy  |           |

FOREIGN PATENT DOCUMENTS

| WO | 2004/104225 A1 | 12/2004 |
| WO | 2013/149306 A1 | 10/2013 |
| WO | 2016/113357 A1 | 7/2016  |

OTHER PUBLICATIONS

Scheibye-Knudsen et al, Mitochondrial deficiency in Cockayne syndrome, Mech Ageing Dev. May-Jun. 2013; 134(0): 275-283. Published online Feb. 19, 2013.*
Karim Harhouri, et al., "MG132-induced progerin clearance is mediated by autophagy activation and splicing regulation," EMBO Molecular Medicine (2017) e201607315.
Ropp PH A et al: "Cloning and characterization o f the human mitochondrial DNA polymerase, DNA polymerase gamma", Genomics,Academic Press, San Diego, US, vol. 36, No. 3, Sep. 1, 1996 (Sep. 1, 1996), pp. 449-458.
B. R. Berquist et al: "Human Cockayne syndrome B protein reciprocally communicates with mitochondria] proteins and promotes transcriptional elongation", Nucleic Acids Research, vol. 40, No. 17, Jun. 28, 2012 (Jun. 28, 2012), pp. 8392-8405.
Peter J. Mckinnon: "DNA repair deficiency and neurological disease", Nature Reviews Neuroscience, vol. 10, No. 2, Jan. 15, 2009 (Jan. 15, 2009), pp. 100-112.
Bowden M A et al.: "High-temperature requirement factor A3 (Htra3): A novel serine protease and its potential role in ovarian function and ovarian cancers", Molecularand Cellular Endocrinology, Elsevier Ireland Ltd, IE, vol. 327, No. 1-2, Oct. 7, 2010 (Oct. 7, 2010), pp. 13-18.
Lin Michael I et al.: "Mitochondrial dysfunction and oxidative stress in neurodegenerative diseases", Nature, Nature Publishing Group, United Kingdom, vol. 443, No. 7113, Oct. 19, 2006 (Oct. 19, 2006), pp. 787-795.
Savopoulos J W et al: "Expression, Purification, and Functional Analysis of the Human Serine Protease HtrA2", Protein Expression and Purification, Academicpress, San Diego, CA, vol. 19, No. 2, Jul. 1, 2000 (Jul. 1, 2000), pp. 227-234.
Barbarapascucci et al.: "A n altered redox balance mediates the hypersensitivity of Cockayne syndrome primary fibroblasts t o oxidative stress", Aging Cell, vol. 11, No. 3, Apr. 5, 2012 (Apr. 5, 2012), pp. 520-529.
Cleaver J E et al.: "Clinical implications of the basic defects in Cockayne syndrome and xeroderma pigmentosum and the DNA lesions responsible for cancer, neurodegeneration and aging", Mechanisms of Ageing and Development, Elsevier Sequoia, Lausanne, CH, vol. 129, No. 7-8, Jul. 1, 2008 (Jul. 1, 2008), pp. 492-497.
European Search Report, Application No. EP14305203, dated Jul. 7, 2014.
International Search Report, Application No. PCT/EP2015/053167, dated Apr. 15, 2015.
Tumurhuu, G et al., MntBAP, a synthetic metalloporphyrin, inhibits production of tumor necrosis factor-alpha in lipopolyasccharide-stimulated RAW 264.7 macrophages cells via inhibiting oxidative stress-mediating p38 and SAPK/JNK signaling, FEMS Immunology and Medical Microbiology, 2007, vol. 49, pp. 304 to 311.
Cline, Mitochondrial DNA damage and its consequences for mitochondrial gene expression, Biochim Biophys Acta. Sep.-Oct. 2012; 1819(9-10):979-91. Epub Jun. 19, 2012.
Furda et al., Quantitative PCR-Based Measurement of Nuclear and Mitochondrial DNA Damage and Repair in Mammalian Cells, Methods Mol Biol. 2014; 1105:419-437, Feb. 4, 2014.
Schei bye-Knudsen et al., Mitochondrial deficiency in Cockayne syndrome, Meeh Ageing Dev. May-Jun. 2013; 134 (5-6):275-83. Epub Feb. 19, 2013.
Kamenisch et al., Proteins of nucleotide and base excision repair pathways interact in mitochondria to protect from loss of subcutaneous fat, a hallmark of aging, J Exp Med. Feb. 15, 2010;207(2):379-90. Epub Jan. 25, 2010.
Grau et al., The role of human HtrA 1 in arthritic disease, J Biol Chem. Mar. 10, 2006;281(10):6124-9. Epub Dec. 22, 2005.
Hakonen et al., Mitochondrial DNA polymerase W748S mutation: a common cause of autosomal recessive ataxia with ancient European origin, Am J Hum Genet. Sep. 2005;77(3):430-41. Epub Jul. 27, 2005.
Han et al.. Mouse Models of Age-related Mitochondrial Neurosensory Hearing Loss, Mol Cell Neurosci. Jul. 2013; 55: 95-100, Published online Jul. 20, 2012.
Longley et al.. Mutant POLG2 disrupts DNA polymerase gamma subunits and causes progressive external ophthalmoplegia. Am J Hum Genet. Jun. 2006;78(6):1026-34. Epub May 4, 2006.
Trifunovic et al.. Premature ageing in mice expressing defective mitochondrial DNA polymerase, Nature. May 27, 2004;429(6990): 417-23.

* cited by examiner

SEQUENCE LISTING

```
<160> NUMBER OF SEQ ID NOS: 18

<210> SEQ ID NO 1
<211> LENGTH: 1239
<212> TYPE: PRT
<213> ORGANISM: Homo sapiens
<220> FEATURE:
<221> NAME/KEY: MISC_FEATURE
<223> OTHER INFORMATION: PolG protein (access number NP_001119603.1)

<400> SEQUENCE: 1

Met Ser Arg Leu Leu Trp Arg Lys Val Ala Gly Ala Thr Val Gly Pro
1               5                   10                  15

Gly Pro Val Pro Ala Pro Gly Arg Trp Val Ser Ser Ser Val Pro Ala
            20                  25                  30

Ser Asp Pro Ser Asp Gly Gln Arg Arg Arg Gln Gln Gln Gln Gln Gln
        35                  40                  45

Gln Gln Gln Gln Gln Gln Gln Pro Gln Gln Pro Gln Val Leu Ser Ser
    50                  55                  60

Glu Gly Gly Gln Leu Arg His Asn Pro Leu Asp Ile Gln Met Leu Ser
65                  70                  75                  80

Arg Gly Leu His Glu Gln Ile Phe Gly Gln Gly Gly Glu Met Pro Gly
                85                  90                  95

Glu Ala Ala Val Arg Arg Ser Val Glu His Leu Gln Lys His Gly Leu
            100                 105                 110

Trp Gly Gln Pro Ala Val Pro Leu Pro Asp Val Glu Leu Arg Leu Pro
        115                 120                 125

Pro Leu Tyr Gly Asp Asn Leu Asp Gln His Phe Arg Leu Leu Ala Gln
    130                 135                 140

Lys Gln Ser Leu Pro Tyr Leu Glu Ala Ala Asn Leu Leu Leu Gln Ala
145                 150                 155                 160

Gln Leu Pro Pro Lys Pro Pro Ala Trp Ala Trp Ala Glu Gly Trp Thr
                165                 170                 175

Arg Tyr Gly Pro Glu Gly Glu Ala Val Pro Val Ala Ile Pro Glu Glu
            180                 185                 190

Arg Ala Leu Val Phe Asp Val Glu Val Cys Leu Ala Glu Gly Thr Cys
        195                 200                 205

Pro Thr Leu Ala Val Ala Ile Ser Pro Ser Ala Trp Tyr Ser Trp Cys
```

```
                    210                 215                 220
Ser Gln Arg Leu Val Glu Glu Arg Tyr Ser Trp Thr Ser Gln Leu Ser
225                 230                 235                 240

Pro Ala Asp Leu Ile Pro Leu Glu Val Pro Thr Gly Ala Ser Ser Pro
                    245                 250                 255

Thr Gln Arg Asp Trp Gln Glu Gln Leu Val Val Gly His Asn Val Ser
                260                 265                 270

Phe Asp Arg Ala His Ile Arg Glu Gln Tyr Leu Ile Gln Gly Ser Arg
                275                 280                 285

Met Arg Phe Leu Asp Thr Met Ser Met His Met Ala Ile Ser Gly Leu
        290                 295                 300

Ser Ser Phe Gln Arg Ser Leu Trp Ile Ala Ala Lys Gln Gly Lys His
305                 310                 315                 320

Lys Val Gln Pro Pro Thr Lys Gln Gly Gln Lys Ser Gln Arg Lys Ala
                    325                 330                 335

Arg Arg Gly Pro Ala Ile Ser Ser Trp Asp Trp Leu Asp Ile Ser Ser
                340                 345                 350

Val Asn Ser Leu Ala Glu Val His Arg Leu Tyr Val Gly Gly Pro Pro
                355                 360                 365

Leu Glu Lys Glu Pro Arg Glu Leu Phe Val Lys Gly Thr Met Lys Asp
370                 375                 380

Ile Arg Glu Asn Phe Gln Asp Leu Met Gln Tyr Cys Ala Gln Asp Val
385                 390                 395                 400

Trp Ala Thr His Glu Val Phe Gln Gln Gln Leu Pro Leu Phe Leu Glu
                    405                 410                 415

Arg Cys Pro His Pro Val Thr Leu Ala Gly Met Leu Glu Met Gly Val
                420                 425                 430

Ser Tyr Leu Pro Val Asn Gln Asn Trp Glu Arg Tyr Leu Ala Glu Ala
                435                 440                 445

Gln Gly Thr Tyr Glu Glu Leu Gln Arg Glu Met Lys Lys Ser Leu Met
            450                 455                 460

Asp Leu Ala Asn Asp Ala Cys Gln Leu Leu Ser Gly Glu Arg Tyr Lys
465                 470                 475                 480

Glu Asp Pro Trp Leu Trp Asp Leu Glu Trp Asp Leu Gln Glu Phe Lys
                    485                 490                 495

Gln Lys Lys Ala Lys Lys Val Lys Lys Glu Pro Ala Thr Ala Ser Lys
                500                 505                 510

Leu Pro Ile Glu Gly Ala Gly Ala Pro Gly Asp Pro Met Asp Gln Glu
            515                 520                 525

Asp Leu Gly Pro Cys Ser Glu Glu Glu Phe Gln Gln Asp Val Met
        530                 535                 540

Ala Arg Ala Cys Leu Gln Lys Leu Lys Gly Thr Thr Glu Leu Leu Pro
545                 550                 555                 560

Lys Arg Pro Gln His Leu Pro Gly His Pro Gly Trp Tyr Arg Lys Leu
                    565                 570                 575

Cys Pro Arg Leu Asp Asp Pro Ala Trp Thr Pro Gly Pro Ser Leu Leu
                580                 585                 590

Ser Leu Gln Met Arg Val Thr Pro Lys Leu Met Ala Leu Thr Trp Asp
            595                 600                 605

Gly Phe Pro Leu His Tyr Ser Glu Arg His Gly Trp Gly Tyr Leu Val
        610                 615                 620

Pro Gly Arg Arg Asp Asn Leu Ala Lys Leu Pro Thr Gly Thr Thr Leu
625                 630                 635                 640
```

-continued

```
Glu Ser Ala Gly Val Val Cys Pro Tyr Arg Ala Ile Glu Ser Leu Tyr
            645                 650                 655

Arg Lys His Cys Leu Glu Gln Gly Lys Gln Gln Leu Met Pro Gln Glu
            660                 665                 670

Ala Gly Leu Ala Glu Glu Phe Leu Leu Thr Asp Asn Ser Ala Ile Trp
            675                 680                 685

Gln Thr Val Glu Glu Leu Asp Tyr Leu Glu Val Glu Ala Glu Ala Lys
            690                 695                 700

Met Glu Asn Leu Arg Ala Ala Val Pro Gly Gln Pro Leu Ala Leu Thr
705                 710                 715                 720

Ala Arg Gly Gly Pro Lys Asp Thr Gln Pro Ser Tyr His His Gly Asn
            725                 730                 735

Gly Pro Tyr Asn Asp Val Asp Ile Pro Gly Cys Trp Phe Phe Lys Leu
            740                 745                 750

Pro His Lys Asp Gly Asn Ser Cys Asn Val Gly Ser Pro Phe Ala Lys
            755                 760                 765

Asp Phe Leu Pro Lys Met Glu Asp Gly Thr Leu Gln Ala Gly Pro Gly
            770                 775                 780

Gly Ala Ser Gly Pro Arg Ala Leu Glu Ile Asn Lys Met Ile Ser Phe
785                 790                 795                 800

Trp Arg Asn Ala His Lys Arg Ile Ser Ser Gln Met Val Val Trp Leu
            805                 810                 815

Pro Arg Ser Ala Leu Pro Arg Ala Val Ile Arg His Pro Asp Tyr Asp
            820                 825                 830

Glu Glu Gly Leu Tyr Gly Ala Ile Leu Pro Gln Val Val Thr Ala Gly
            835                 840                 845

Thr Ile Thr Arg Arg Ala Val Glu Pro Thr Trp Leu Thr Ala Ser Asn
850                 855                 860

Ala Arg Pro Asp Arg Val Gly Ser Glu Leu Lys Ala Met Val Gln Ala
865                 870                 875                 880

Pro Pro Gly Tyr Thr Leu Val Gly Ala Asp Val Asp Ser Gln Glu Leu
            885                 890                 895

Trp Ile Ala Ala Val Leu Gly Asp Ala His Phe Ala Gly Met His Gly
            900                 905                 910

Cys Thr Ala Phe Gly Trp Met Thr Leu Gln Gly Arg Lys Ser Arg Gly
            915                 920                 925

Thr Asp Leu His Ser Lys Thr Ala Thr Val Gly Ile Ser Arg Glu
930                 935                 940

His Ala Lys Ile Phe Asn Tyr Gly Arg Ile Tyr Gly Ala Gly Gln Pro
945                 950                 955                 960

Phe Ala Glu Arg Leu Leu Met Gln Phe Asn His Arg Leu Thr Gln Gln
            965                 970                 975

Glu Ala Ala Glu Lys Ala Gln Gln Met Tyr Ala Ala Thr Lys Gly Leu
            980                 985                 990

Arg Trp Tyr Arg Leu Ser Asp Glu Gly Glu Trp Leu Val Arg Glu Leu
            995                 1000                1005

Asn Leu Pro Val Asp Arg Thr Glu Gly Gly Trp Ile Ser Leu Gln
       1010                1015                1020

Asp Leu Arg Lys Val Gln Arg Glu Thr Ala Arg Lys Ser Gln Trp
       1025                1030                1035

Lys Lys Trp Glu Val Val Ala Glu Arg Ala Trp Lys Gly Gly Thr
       1040                1045                1050
```

| | | | | | | | | | | | | |
|---|---|---|---|---|---|---|---|---|---|---|---|---|
|Glu|Ser|Glu|Met|Phe|Asn|Lys|Leu|Glu|Ser|Ile|Ala|Thr Ser Asp|
| |1055| | | |1060| | | |1065| | | |

Ile Pro Arg Thr Pro Val Leu Gly Cys Cys Ile Ser Arg Ala Leu
    1070            1075            1080

Glu Pro Ser Ala Val Gln Glu Glu Phe Met Thr Ser Arg Val Asn
    1085            1090            1095

Trp Val Val Gln Ser Ser Ala Val Asp Tyr Leu His Leu Met Leu
    1100            1105            1110

Val Ala Met Lys Trp Leu Phe Glu Glu Phe Ala Ile Asp Gly Arg
    1115            1120            1125

Phe Cys Ile Ser Ile His Asp Glu Val Arg Tyr Leu Val Arg Glu
    1130            1135            1140

Glu Asp Arg Tyr Arg Ala Ala Leu Ala Leu Gln Ile Thr Asn Leu
    1145            1150            1155

Leu Thr Arg Cys Met Phe Ala Tyr Lys Leu Gly Leu Asn Asp Leu
    1160            1165            1170

Pro Gln Ser Val Ala Phe Phe Ser Ala Val Asp Ile Asp Arg Cys
    1175            1180            1185

Leu Arg Lys Glu Val Thr Met Asp Cys Lys Thr Pro Ser Asn Pro
    1190            1195            1200

Thr Gly Met Glu Arg Arg Tyr Gly Ile Pro Gln Gly Glu Ala Leu
    1205            1210            1215

Asp Ile Tyr Gln Ile Ile Glu Leu Thr Lys Gly Ser Leu Glu Lys
    1220            1225            1230

Arg Ser Gln Pro Gly Pro
    1235

<210> SEQ ID NO 2
<211> LENGTH: 4452
<212> TYPE: DNA
<213> ORGANISM: Homo sapiens
<220> FEATURE:
<221> NAME/KEY: source
<222> LOCATION: (1)..(4452)
<223> OTHER INFORMATION: POLG DNA sequence

<400> SEQUENCE: 2

```
gcggaccggc cgggtggagg ccacacgcta ccccgaggct gcgtaggccg cgcgaagggg      60
gacgccgtgc cgtgggcctg ggtcggggg agcagcagac cgggaagcac cgatttgggg     120
tggaaggcag gcatggtcaa acccatttca ctgacaggag agcagagaca ggacgtgtct    180
ctctccacgt cttccagcca gtaaaagaag ccaagctgga gcccaaagcc aggtgttctg    240
actcccagcg tgggggtccc tgcaccaacc atgagccgcc tgctctggag gaaggtggcc    300
ggcgccaccg tcgggccagg gccggttcca gctccgggc gctgggtctc cagctccgtc    360
cccgcgtccg accccagcga cgggcagcgg cggcggcagc agcagcagca gcagcagcag    420
cagcagcaac agcagcctca gcagccgcaa gtgctatcct cggagggcgg gcagctgcgg    480
cacaacccat ggacatcca gatgctctcg agagggctgc acgagcaaat cttcgggcaa    540
ggaggggaga tgcctggcga ggccgcggtg cgccgcagcg tcgagcacct gcagaagcac    600
gggctctggg ggcagccagc cgtgcccttg ccgacgtgg agctgcgcct gccgccctc    660 tacggggaca acctggacca gcacttccgc ctcctggccc agaagcagag cctgccctac    720
ctggaggcgg ccaacttgct gttgcaggcc cagctgcccc gaagccccc ggcttgggcc    780 tgggcggagg gctggacccg gtacggcccc gaggggagg ccgtaccgt ggccatcccc    840
```

```
gaggagcggg ccctggtgtt cgacgtggag gtctgcttgg cagagggaac ttgccccaca    900
ttggcggtgg ccatatcccc ctcggcctgg tattcctggt gcagccagcg gctggtggaa    960
gagcgttact cttggaccag ccagctgtcg ccggctgacc tcatcccect ggaggtccct   1020 actggtgcca gcagcccac ccagagagac tggcaggagc agttagtggt ggggcacaat   1080
gtttcctttg accgagctca tatcagggag cagtacctga tccagggttc ccgcatgcgt   1140
ttcctggaca ccatgagcat gcacatggcc atctcagggc taagcagctt ccagcgcagt   1200
ctgtggatag cagccaagca gggcaaacac aaggtccagc cccccacaaa gcaaggccag   1260
aagtcccaga ggaaagccag aagaggccca gcgatctcat cctgggactg gctggacatc   1320
agcagtgtca acagtctggc agaggtgcac agactttatg taggggggcc tcccttagag   1380
aaggagcctc gagaactgtt tgtgaagggc accatgaagg acattcgtga gaacttccag   1440
gacctgatgc agtactgtgc ccaggacgtg tgggccaccc atgaggtttt ccagcagcag   1500
ctaccgctct tcttggagag gtgtccccac ccagtgactc tggccggcat gctggagatg   1560
ggtgtctcct acctgcctgt caaccagaac tgggagcgtt acctggcaga ggcacagggc   1620
acttatgagg agctccagcg ggagatgaag aagtcgttga tggatctggc caatgatgcc   1680
tgccagctgc tctcaggaga gaggtacaaa aagacccct ggctctggga cctggagtgg   1740
gacctgcaag aatttaagca gaagaaagct aagaaggtga agaaggaacc agccacagcc   1800
agcaagttgc ccatcgaggg ggctgggggcc cctggtgatc ccatggatca ggaagacctc   1860
ggcccctgca gtgaggagga ggagtttcaa caagatgtca tggcccgcgc ctgcttgcag   1920
aagctgaagg ggaccacaga gctcctgccc aagcggcccc agcaccttcc tggacaccct   1980
ggatggtacc ggaagctctg cccccggcta gacgaccctg catggacccc gggccccagc   2040
ctcctcagcc tgcagatgcg ggtcacacct aaactcatgg cacttacctg ggatggcttc   2100
cctctgcact actcagagcg tcatggctgg ggctacttgg tgcctgggcg gcgggacaac   2160
ctggccaagc tgccgacagg taccaccctg gagtcagctg gggtggtctg ccctacaga   2220 gccatcgagt ccctgtacag gaagcactgt ctcgaacagg ggaagcagca gctgatgccc   2280
caggaggccg gcctggcgga ggagttcctg ctcactgaca atagtgccat atggcaaacg   2340
gtagaagaac tggattactt agaagtggag gctgaggcca agatggagaa cttgcgagct   2400
gcagtgccag gtcaacccct agctctgact gcccgtggtg gccccaagga cacccagccc   2460
agctatcacc atggcaatgg accttacaac gacgtggaca tccctggctg ctggttttc   2520 aagctgcctc acaaggatgg taatagctgt aatgtgggaa gccccttgc caaggacttc   2580 ctgcccaaga tggaggatgg caccctgcag gctggcccag gaggtgccag tgggccccgt   2640
gctctggaaa tcaacaaaat gatttctttc tggaggaacg cccataaacg tatcagctcc   2700
cagatggtgg tgtggctgcc caggtcagct ctgccccgtg ctgtgatcag gcaccccgac   2760
tatgatgagg aaggcctcta tggggccatc ctgccccaag tggtgactgc cggcaccatc   2820
actcgccggg ctgtggagcc cacatggctc accgccagca tgcccggcc tgaccgagta   2880 ggcagtgagt tgaaagccat ggtgcaggcc ccacctggct acacccttgt gggtgctgat   2940
gtggactccc aagagctgtg gattgcagct gtgcttggag acgccacttt gccggcatg   3000 catggctgca cagccttggg gtggatgaca ctgcagggca ggaagagcag gggcactgat   3060
ctacacagta agacagccac tactgtgggc atcagccgtg agcatgccaa aatcttcaac   3120 tacgccgca tctatggtgc tgggcagccc tttgctgagc gcttactaat gcagtttaac   3180
caccggctca cacagcagga ggcagctgag aaggcccagc agatgtacgc tgccaccaag   3240
```

```
ggcctccgct ggtatcggct gtcggatgag ggcgagtggc tggtgaggga gttgaacctc   3300
ccagtggaca ggactgaggg tggctggatt ccctgcagg atctgcgcaa ggtccagaga    3360
gaaactgcaa ggaagtcaca gtggaagaag tgggaggtgg ttgctgaacg ggcatggaag   3420
gggggcacag agtcagaaat gttcaataag cttgagagca ttgctacgtc tgacatacca   3480
cgtaccccgg tgctgggctg ctgcatcagc cgagccctgg agccctcggc tgtccaggaa   3540
gagtttatga ccagccgtgt gaattgggtg gtacagagct ctgctgttga ctacttacac   3600
ctcatgcttg tggccatgaa gtggctgttt gaagagtttg ccatagatgg gcgcttctgc   3660
atcagcatcc atgacgaggt tcgctacctg gtgcgggagg aggaccgcta ccgcgctgcc   3720
ctggccttgc agatcaccaa cctcttgacc aggtgcatgt ttgcctacaa gctgggtctg   3780
aatgacttgc cccagtcagt cgccttttc agtgcagtcg atattgaccg gtgcctcagg   3840
aaggaagtga ccatggattg taaaacccct tccaacccaa ctgggatgga aaggagatac   3900
gggattcccc agggtgaagc gctggatatt taccagataa ttgaactcac caaaggctcc   3960
ttggaaaaac gaagccagcc tggaccatag cactgcctgg aggctctgta tttgctcccg   4020
tggagcttca tcggggtggt gcaggctccc aaactcaggc tttcagctgt gcttttttgca  4080 aaagggcttg cctaaggcca gccattttc agtagcagga cctgccaaga agattccttc   4140
taactgaagg tgcagttgaa ttcagtgggt tcagaaccaa gatgccaaca tcggtgtgga   4200
ctacaggaca agggcattg ttgcttgttg ggtaaaaatg aagcagaagc cccaaagttc    4260
acattaactc aggcatttca tttatttttt ccttttcttc ttggctggtt ctttgttctg   4320
tcccccatgc tctgatgcag tgccctagaa ggggaaagaa ttaatgctct aacgtgataa   4380
acctgctcca aggcagtgga aataaaaaga aggaaaaaaa agactctatc ttctcaaaaa   4440
aaaaaaaaaa aa                                                       4452
```

<210> SEQ ID NO 3
<211> LENGTH: 485
<212> TYPE: PRT
<213> ORGANISM: Homo sapiens
<220> FEATURE:
<221> NAME/KEY: MISC_FEATURE
<223> OTHER INFORMATION: POLG2 protein (access number NP_009146.2)

<400> SEQUENCE: 3

Met Arg Ser Arg Val Ala Val Arg Ala Cys His Lys Val Cys Arg Cys
1               5                   10                  15

Leu Leu Ser Gly Phe Gly Gly Arg Val Asp Ala Gly Gln Pro Glu Leu
            20                  25                  30

Leu Thr Glu Arg Ser Ser Pro Lys Gly Gly His Val Lys Ser His Ala
        35                  40                  45

Glu Leu Glu Gly Asn Gly Glu His Pro Glu Ala Pro Gly Ser Gly Glu
    50                  55                  60

Gly Ser Glu Ala Leu Leu Glu Ile Cys Gln Arg His Phe Leu Ser
65                  70                  75                  80

Gly Ser Lys Gln Gln Leu Ser Arg Asp Ser Leu Ser Gly Cys His
            85                  90                  95

Pro Gly Phe Gly Pro Leu Gly Val Glu Leu Arg Lys Asn Leu Ala Ala
            100                 105                 110

Glu Trp Trp Thr Ser Val Val Val Phe Arg Glu Gln Val Phe Pro Val
        115                 120                 125

Asp Ala Leu His His Lys Pro Gly Pro Leu Leu Pro Gly Asp Ser Ala

```
            130                 135                 140
Phe Arg Leu Val Ser Ala Glu Thr Leu Arg Glu Ile Leu Gln Asp Lys
145                 150                 155                 160

Glu Leu Ser Lys Glu Gln Leu Val Ala Phe Leu Glu Asn Val Leu Lys
                165                 170                 175

Thr Ser Gly Lys Leu Arg Glu Asn Leu Leu His Gly Ala Leu Glu His
            180                 185                 190

Tyr Val Asn Cys Leu Asp Leu Val Asn Lys Arg Leu Pro Tyr Gly Leu
            195                 200                 205

Ala Gln Ile Gly Val Cys Phe His Pro Val Phe Asp Thr Lys Gln Ile
        210                 215                 220

Arg Asn Gly Val Lys Ser Ile Gly Glu Lys Thr Glu Ala Ser Leu Val
225                 230                 235                 240

Trp Phe Thr Pro Pro Arg Thr Ser Asn Gln Trp Leu Asp Phe Trp Leu
                245                 250                 255

Arg His Arg Leu Gln Trp Trp Arg Lys Phe Ala Met Ser Pro Ser Asn
            260                 265                 270

Phe Ser Ser Ser Asp Cys Gln Asp Glu Glu Gly Arg Lys Gly Asn Lys
        275                 280                 285

Leu Tyr Tyr Asn Phe Pro Trp Gly Lys Glu Leu Ile Glu Thr Leu Trp
290                 295                 300

Asn Leu Gly Asp His Glu Leu Leu His Met Tyr Pro Gly Asn Val Ser
305                 310                 315                 320

Lys Leu His Gly Arg Asp Gly Arg Lys Asn Val Val Pro Cys Val Leu
                325                 330                 335

Ser Val Asn Gly Asp Leu Asp Arg Gly Met Leu Ala Tyr Leu Tyr Asp
            340                 345                 350

Ser Phe Gln Leu Thr Glu Asn Ser Phe Thr Arg Lys Lys Asn Leu His
        355                 360                 365

Arg Lys Val Leu Lys Leu His Pro Cys Leu Ala Pro Ile Lys Val Ala
370                 375                 380

Leu Asp Val Gly Arg Gly Pro Thr Leu Glu Leu Arg Gln Val Cys Gln
385                 390                 395                 400

Gly Leu Phe Asn Glu Leu Leu Glu Asn Gly Ile Ser Val Trp Pro Gly
                405                 410                 415

Tyr Leu Glu Thr Met Gln Ser Ser Leu Glu Gln Leu Tyr Ser Lys Tyr
            420                 425                 430

Asp Glu Met Ser Ile Leu Phe Thr Val Leu Val Thr Glu Thr Thr Leu
        435                 440                 445

Glu Asn Gly Leu Ile His Leu Arg Ser Arg Asp Thr Thr Met Lys Glu
450                 455                 460

Met Met His Ile Ser Lys Leu Lys Asp Phe Leu Ile Lys Tyr Ile Ser
465                 470                 475                 480

Ser Ala Lys Asn Val
                485

<210> SEQ ID NO 4
<211> LENGTH: 1607
<212> TYPE: DNA
<213> ORGANISM: Homo sapiens
<220> FEATURE:
<221> NAME/KEY: source
<222> LOCATION: (1)..(1607)
<223> OTHER INFORMATION: POLG2 DNA sequence

<400> SEQUENCE: 4
```

-continued

```
gcctgcgccg tggcctctcc ggattctgtt aacggtagtg gtggcttgtt gggatccgtt       60
gagtgatggg agagtgtgct ctttaacttc ggagagagat cgcgctctcgt gtagccgtca     120 gggcctgcca aaggtctgc aggtgcctgt tgtctgggtt tgggggtcga gtagatgcgg       180
ggcagccgga gctgttgacg gaaaggagta gccccaaagg agggcatgtg aagtcgcacg      240
cggagctcga ggggaacggc gagcacccag aagcccccgg gtctggagag ggaagcgagg     300
cgctgttaga gatctgtcag agaaggcatt tcctaagtgg aagcaagcag cagcttagcc     360
gggattctct tctgagtggg tgccaccccg gcttcggacc cttgggcgta gagttgcgga     420
agaacctggc cgcagaatgg tggacctcgg tggtggtgtt cagggagcag gtattcccgg     480
tggacgccct ccaccacaaa ccaggccctt tgctacccgg ggacagtgcc ttcaggttag     540
tttctgcaga aactctacgc gaaatcttgc aagacaaaga gctgagtaag gaacagctag     600
tagcatttct tgagaacgta ttaaaaactt ctgggaaact acgggagaac cttcttcacg     660
gtgccttgga acactatgtt aattgcctgg atctggtaaa caagaggcta ccttatggcc     720
ttgctcagat tggagtgtgt tttcatcctg ttttgacac taagcagata cgaaatggtg      780
ttaaaagtat tggtgagaag actgaagctt cgttagtatg gtttactcct ccgagaactt    840
caaaccagtg gcttgatttc tggttacgtc atcgactcca gtggtggaga aagtttgcca     900
tgagtccatc taacttcagc agcagtgact gtcaggatga agaaggccgg aaaggaaaca    960
aactttacta caattttccc tggggaaagg agttaataga aaccctgtgg aacctaggag    1020
atcacgaact tttacacatg tatcctggca atgtgtctaa attacatggc cgagatggac    1080
gaaaaaatgt ggttccttgt gttctctctg taaatgggga cctagaccga ggcatgctgg    1140
cctacctcta tgattctttc cagctgacag agaactcctt tacaagaaag aaaaatcttc    1200
atagaaaggt acttaaactt cacccttgtt tagcccctat taaggttgct ttggatgtag    1260
gaagaggccc cacattggaa ctaagacagg tttgtcaagg gctatttaat gagttactag    1320
aaaatgggat ttctgtgtgg cctggttatt tggaaactat gcagtcctca ttggaacaac    1380
tttattcgaa gtatgatgaa atgagtattc tcttcacagt tttggttact gaaactactt    1440
tggagaatgg attaatacat ctgagaagca gagacaccac aatgaaggaa atgatgcata    1500
tatccaaatt aaaagacttt ttgattaagt atatatcatc agctaagaat gtatagattt    1560
ttatatttgt ataataaata ttcttctctc ctaaaaaaaa aaaaaaa                   1607
```

<210> SEQ ID NO 5
<211> LENGTH: 453
<212> TYPE: PRT
<213> ORGANISM: Homo sapiens
<220> FEATURE:
<221> NAME/KEY: MISC_FEATURE
<223> OTHER INFORMATION: HTRA3 protein (access number NP_444272.1)

<400> SEQUENCE: 5

```
Met Gln Ala Arg Ala Leu Leu Leu Ala Ala Leu Ala Ala Leu Ala Leu
1               5                   10                  15

Ala Arg Glu Pro Pro Ala Ala Pro Cys Pro Ala Arg Cys Asp Val Ser
                20                  25                  30

Arg Cys Pro Ser Pro Arg Cys Pro Gly Gly Tyr Val Pro Asp Leu Cys
            35                  40                  45

Asn Cys Cys Leu Val Cys Ala Ala Ser Glu Gly Glu Pro Cys Gly Gly
        50                  55                  60

Pro Leu Asp Ser Pro Cys Gly Glu Ser Leu Glu Cys Val Arg Gly Leu
```

```
            65                  70                  75                  80

Cys Arg Cys Arg Trp Ser His Ala Val Cys Gly Thr Asp Gly His Thr
                        85                  90                  95

Tyr Ala Asn Val Cys Ala Leu Gln Ala Ser Arg Arg Ala Leu Gln
                        100                 105                 110

Leu Ser Gly Thr Pro Val Arg Leu Gln Lys Gly Ala Cys Pro Leu
                        115                 120                 125

Gly Leu His Gln Leu Ser Ser Pro Arg Tyr Lys Phe Asn Phe Ile Ala
        130                 135                 140

Asp Val Val Glu Lys Ile Ala Pro Ala Val His Ile Glu Leu Phe
        145                 150                 155                 160

Leu Arg His Pro Leu Phe Gly Arg Asn Val Pro Leu Ser Ser Gly Ser
                        165                 170                 175

Gly Phe Ile Met Ser Glu Ala Gly Leu Ile Ile Thr Asn Ala His Val
                        180                 185                 190

Val Ser Ser Asn Ser Ala Ala Pro Gly Arg Gln Gln Leu Lys Val Gln
                        195                 200                 205

Leu Gln Asn Gly Asp Ser Tyr Glu Ala Thr Ile Lys Asp Ile Asp Lys
                        210                 215                 220

Lys Ser Asp Ile Ala Thr Ile Lys Ile His Pro Lys Lys Lys Leu Pro
        225                 230                 235                 240

Val Leu Leu Leu Gly His Ser Ala Asp Leu Arg Pro Gly Glu Phe Val
                        245                 250                 255

Val Ala Ile Gly Ser Pro Phe Ala Leu Gln Asn Thr Val Thr Thr Gly
                        260                 265                 270

Ile Val Ser Thr Ala Gln Arg Glu Gly Arg Glu Leu Gly Leu Arg Asp
                        275                 280                 285

Ser Asp Met Asp Tyr Ile Gln Thr Asp Ala Ile Ile Asn Tyr Gly Asn
                        290                 295                 300

Ser Gly Gly Pro Leu Val Asn Leu Asp Gly Glu Val Ile Gly Ile Asn
        305                 310                 315                 320

Thr Leu Lys Val Thr Ala Gly Ile Ser Phe Ala Ile Pro Ser Asp Arg
                        325                 330                 335

Ile Thr Arg Phe Leu Thr Glu Phe Gln Asp Lys Gln Ile Lys Asp Trp
                        340                 345                 350

Lys Lys Arg Phe Ile Gly Ile Arg Met Arg Thr Ile Thr Pro Ser Leu
                        355                 360                 365

Val Asp Glu Leu Lys Ala Ser Asn Pro Asp Phe Pro Glu Val Ser Ser
        370                 375                 380

Gly Ile Tyr Val Gln Glu Val Ala Pro Asn Ser Pro Ser Gln Arg Gly
        385                 390                 395                 400

Gly Ile Gln Asp Gly Asp Ile Ile Val Lys Val Asn Gly Arg Pro Leu
                        405                 410                 415

Val Asp Ser Ser Glu Leu Gln Glu Ala Val Leu Thr Glu Ser Pro Leu
                        420                 425                 430

Leu Leu Glu Val Arg Arg Gly Asn Asp Asp Leu Leu Phe Ser Ile Ala
                        435                 440                 445

Pro Glu Val Val Met
                        450

<210> SEQ ID NO 6
<211> LENGTH: 2589
<212> TYPE: DNA
<213> ORGANISM: Homo sapiens
```

```
<220> FEATURE:
<221> NAME/KEY: source
<222> LOCATION: (1)..(2589)
<223> OTHER INFORMATION: HTRA3 DNA sequence

<400> SEQUENCE: 6
ggagggagct ggtccctgcg ctccctgcgc cctggggatg cccctgccgc cctgacgccc      60
gccagcctga gccaccggcg catgtgaccg cgcgtccgcc ccagtcccat ccgtaggcgc     120
ccggcgcccg gccccgcagc ggcctcgttg tccccgccgg ccccgcccg gtctcccgcg     180 ctgccacccg ccgccggccc tgccgccatg caggcgcgag cgctgctcct ggccgcgttg     240
gccgcgctgg cgctggcccg ggagcccccct cgggcgccgt gtcccgcgcg ctgcgacgtg     300
tcgcggtgtc ccagccccg ctgccccggc ggctacgtgc ccgacctctg caactgctgc     360
ctggtgtgcg ccgccagcga gggcgagccc tgtggcggcc ctctggactc gccttgcggc     420
gagagcctgg agtgcgtgcg cggcctatgc cgctgccgct ggtcgcacgc cgtgtgtggc     480
accgacgggc acacctatgc caacgtgtgc gcgctgcagg cggccagccg ccgcgcgctg     540
cagctctccg ggacgcccgt gcgccagctg cagaagggcg cctgcccgtt gggtctccac     600
cagctgagca gccgcgcta caagttcaac ttcattgctg acgtggtgga aagatcgca     660 ccagccgtgg tccacataga gctcttcctg agacaccgc tgtttggccg caacgtgccc     720
ctgtccagcg gttctggctt catcatgtca gaggccggcc tgatcatcac caatgcccac     780
gtggtgtcca gcaacagtgc tgccccgggc aggcagcagc tcaaggtgca gctacagaat     840
ggggactcct atgaggccac catcaaagac atcgacaaga gtcggacat tgccaccatc     900 aagatccatc ccaagaaaaa gctccctgtg ttgttgctgg gtcactcggc cgacctgcgg     960
cctggggagt ttgtggtggc catcggcagt cccttcgccc tacagaacac agtgacaacg    1020
ggcatcgtca gcactgccca gcgggagggc agggagctgg gcctccggga ctccgacatg    1080
gactacatcc agacggatgc catcatcaac tacgggaact ccgggggacc actggtgaac    1140
ctggatggcg aggtcattgg catcaacacg ctcaaggtca cggctggcat ctcctttgcc    1200
atcccctcag accgcatcac acggttcctc acagagttcc aagacaagca gatcaaagac    1260
tggaagaagc gcttcatcgg catacggatg cggacgatca caccaagcct ggtggatgag    1320
ctgaaggcca gcaacccgga cttcccagag gtcagcagtg aatttatgt gcaagaggtt    1380 gcgccgaatt caccttctca gagaggcgg atccaagatg tgacatcat cgtcaaggtc    1440 aacgggcgtc ctctagtgga ctcgagtgag ctgcaggagg ccgtgctgac cgagtctcct    1500
ctcctactgg aggtgcggcg ggggaacgac gacctcctct tcagcatcgc acctgaggtg    1560
gtcatgtgag gggcgcattc ctccagcgcc aagcgtcaga gcctgcagac aacggagggc    1620 agcgccccc cgagatcagg acgaaggacc accgtcggtc ctcagcaggg cggcagcctc    1680
ctcctggctg tccggggcag agcggaggct gggcttggcc aggggcccga atttccgcct    1740
ggggagtgtt ggatccacat cccggtgccg ggagggaag cccaacatcc ccttgtacag    1800
atgatcctga aagtcacttc caagttctcc ggatattcac aaaactgcct tccatggagg    1860 tccctcctc tcctagcttc ccgcctctgc cctgtgaac acccatctgc agtatcccct    1920
gctcctgccc ctcctactgc aggtctgggc tgccaagctt cttccccct gacaaacgcc    1980 cacctgacct gaggcccag cttccctctg ccctaggact taccaagctg tagggccagg    2040
gctgctgcct gccagcctgg ggtccctgga ggacaggtca catctgatcc ctttggggtg    2100
cgggggtggg gtccagccca gagcaggcac tgagtgaatg cccctggct gcggagctga    2160
```

-continued

```
gccccgccct gccatgaggt tttcctcccc aggcaggcag gaggccgcgg ggagcacgtg    2220
gaaagttggc tgctgcctgg ggaagcttct cctccccaag gcggccatgg ggcagcctgc    2280
agaggacagt ggacgtggag ctgcggggtg tgaggactga gccggcttcc ccttcccacg    2340
cagctctggg atgcagcagc cgctcgcatg gaagtgccgc ccagaggcat gcaggctgct    2400
gggcaccacc ccctcatcca gggaacgagt gtgtctcaag gggcatttgt gagctttgct    2460
gtaaatggat tcccagtgtt gcttgtactg tatgtttctc tactgtatgg aaaataaagt    2520
ttacaagcac acggttctca gccaaaaaaa aaaaaaaaaa aaaaaaaaaa aaaaaaaaaa    2580
aaaaaaaaa                                                           2589
```

<210> SEQ ID NO 7
<211> LENGTH: 458
<212> TYPE: PRT
<213> ORGANISM: Homo sapiens
<220> FEATURE:
<221> NAME/KEY: MISC_FEATURE
<223> OTHER INFORMATION: HTRA2 PROTEIN (access number NP_037379.1)

<400> SEQUENCE: 7

```
Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu Thr
            20                  25                  30

Pro Asp Leu Arg Ala Leu Leu Thr Ser Gly Thr Ser Asp Pro Arg Ala
        35                  40                  45

Arg Val Thr Tyr Gly Thr Pro Ser Leu Trp Ala Arg Leu Ser Val Gly
    50                  55                  60

Val Thr Glu Pro Arg Ala Cys Leu Thr Ser Gly Thr Pro Gly Pro Arg
65                  70                  75                  80

Ala Gln Leu Thr Ala Val Thr Pro Asp Thr Arg Thr Arg Glu Ala Ser
                85                  90                  95

Glu Asn Ser Gly Thr Arg Ser Arg Ala Trp Leu Ala Val Ala Leu Gly
            100                 105                 110

Ala Gly Gly Ala Val Leu Leu Leu Leu Trp Gly Gly Gly Arg Gly Pro
        115                 120                 125

Pro Ala Val Leu Ala Ala Val Pro Ser Pro Pro Pro Ala Ser Pro Arg
    130                 135                 140

Ser Gln Tyr Asn Phe Ile Ala Asp Val Val Glu Lys Thr Ala Pro Ala
145                 150                 155                 160

Val Val Tyr Ile Glu Ile Leu Asp Arg His Pro Phe Leu Gly Arg Glu
                165                 170                 175

Val Pro Ile Ser Asn Gly Ser Gly Phe Val Val Ala Ala Asp Gly Leu
            180                 185                 190

Ile Val Thr Asn Ala His Val Val Ala Asp Arg Arg Arg Val Arg Val
        195                 200                 205

Arg Leu Leu Ser Gly Asp Thr Tyr Glu Ala Val Val Thr Ala Val Asp
    210                 215                 220

Pro Val Ala Asp Ile Ala Thr Leu Arg Ile Gln Thr Lys Glu Pro Leu
225                 230                 235                 240

Pro Thr Leu Pro Leu Gly Arg Ser Ala Asp Val Arg Gln Gly Glu Phe
                245                 250                 255

Val Val Ala Met Gly Ser Pro Phe Ala Leu Gln Asn Thr Ile Thr Ser
            260                 265                 270

Gly Ile Val Ser Ser Ala Gln Arg Pro Ala Arg Asp Leu Gly Leu Pro
```

```
                    275                 280                 285
        Gln Thr Asn Val Glu Tyr Ile Gln Thr Asp Ala Ala Ile Asp Phe Gly
            290                 295                 300

Asn Ser Gly Gly Pro Leu Val Asn Leu Asp Gly Glu Val Ile Gly Val
        305                 310                 315                 320

Asn Thr Met Lys Val Thr Ala Gly Ile Ser Phe Ala Ile Pro Ser Asp
                        325                 330                 335

Arg Leu Arg Glu Phe Leu His Arg Gly Glu Lys Lys Asn Ser Ser Ser
                    340                 345                 350

Gly Ile Ser Gly Ser Gln Arg Arg Tyr Ile Gly Val Met Met Leu Thr
                355                 360                 365

Leu Ser Pro Ser Ile Leu Ala Glu Leu Gln Leu Arg Glu Pro Ser Phe
            370                 375                 380

Pro Asp Val Gln His Gly Val Leu Ile His Lys Val Ile Leu Gly Ser
        385                 390                 395                 400

Pro Ala His Arg Ala Gly Leu Arg Pro Gly Asp Val Ile Leu Ala Ile
                        405                 410                 415

Gly Glu Gln Met Val Gln Asn Ala Glu Asp Val Tyr Glu Ala Val Arg
                    420                 425                 430

Thr Gln Ser Gln Leu Ala Val Gln Ile Arg Arg Gly Arg Glu Thr Leu
                435                 440                 445

Thr Leu Tyr Val Thr Pro Glu Val Thr Glu
            450                 455

<210> SEQ ID NO 8
<211> LENGTH: 2550
<212> TYPE: DNA
<213> ORGANISM: Homo sapiens
<220> FEATURE:
<221> NAME/KEY: source
<222> LOCATION: (1)..(2550)
<223> OTHER INFORMATION: HTRA2 DNA sequence

<400> SEQUENCE: 8
cgtggatccc gagaaagagg cgcaggacga ggaggcagaa cccgactggc gcgtagagca      60
gcagcacgag cagtaggaag cagtcacccg gaagcctggg ggcgagaggc gaagtggtca     120
ggcgccgaag gccgagagca cgcggggatc ggtctcttcc cgccgggtct cttaccggtg     180
cgagtcaaag agccgctccg gccccggccc tgagggaagc tccataactg ctgcttcagg     240
agcgcccggc cgtcgccgcc gccgccatt  tcgcgcccgg ccgcaggggc tcttgggaag     300
gcggagtctt tgggcatccg cccggggtga ggggaccccga agtcctgagg cgcgccggaa     360
gggctagcgg tcccagcata ccccgcggcc ccttgggccg tctcacaact cgcgtccggc     420
ggagaccaca attcccggca ttcgtggggc agggaggagt cggcctcccg gaatcctggt     480
cccggcgtgc acttctgaag gacttcaggt accggcgtgc cccgcgtcct actgtccgcc     540
tgctcgcgtc ctgggtgccg cctctgagta gggcgggcga ggaggcagcc aaggcggagc     600
tgatggctgc gccgagggcg gggcggggtg caggctggag ccttcgggca tggcgggctt     660
tggggggcat cgctgggggg aggagacccc gtttgacccc tgacctccgg gccctgctga     720
cgtcaggaac ttctgacccc cgggcccgag tgacttatgg accccccagt ctctgggccc     780
ggttgtctgt tggggtcact gaaccccgag catgcctgac gtctgggacc ccgggtcccc     840
gggcacaact gactgcggtg accccagata ccaggacccg ggaggcctca gagaactctg     900
gaacccgttc gcgcgcgtgg ctggcggtgg cgctgggcgc tggggggca gtgctgttgt     960
```

```
tgttgtgggg cggggtcgg ggtcctccgg ccgtcctcgc cgccgtccct agcccgccgc    1020
ccgcttctcc ccggagtcag tacaacttca tcgcagatgt ggtggagaag acagcacctg    1080
ccgtggtcta tatcgagatc ctggaccggc accctttctt gggccgcgag gtccctatct    1140
cgaacggctc aggattcgtg gtggctgccg atgggctcat tgtcaccaac gcccatgtgg    1200
tggctgatcg gcgcagagtc cgtgtgagac tgctaagcgg cgacacgtat gaggccgtgg    1260
tcacagctgt ggatcccgtg gcagacatcg caacgctgag gattcagact aaggagcctc    1320
tccccacgct gcctctggga cgctcagctg atgtccggca aggggagttt gttgttgcca    1380
tgggaagtcc ctttgcactg cagaacacga tcacatccgg cattgttagc tctgctcagc    1440
gtccagccag agacctggga ctcccccaaa ccaatgtgga atacattcaa actgatgcag    1500
ctattgattt tggaaactct ggaggtcccc tggttaacct ggatggggag gtgattggag    1560
tgaacaccat gaaggtcaca gctggaatct cctttgccat cccttctgat cgtcttcgag    1620
agtttctgca tcgtggggaa aagaagaatt cctcctccgg aatcagtggg tcccagcggc    1680
gctacattgg ggtgatgatg ctgaccctga gtcccagcat ccttgctgaa ctacagcttc    1740
gagaaccaag ctttcccgat gttcagcatg gtgtactcat ccataaagtc atcctgggct    1800
cccctgcaca ccgggctggt ctgcggcctg gtgatgtgat tttggccatt ggggagcaga    1860
tggtacaaaa tgctgaagat gtttatgaag ctgttcgaac ccaatcccag ttggcagtgc    1920
agatccggcg gggacgagaa acactgacct tatatgtgac ccctgaggtc acagaatgaa    1980
tagatcacca agagtatgag gctcctgctc tgatttcctc cttgcctttc tggctgaggt    2040
tctgagggca ccgagacaga gggttaaatg aaccagtggg ggcaggtccc tccaaccacc    2100
agcactgact cctgggctct gaagaatcac agaaacactt tttatataaa ataaaattat    2160
acctagcaac atattatagt aaaaaatgag gtgggagggc tggatctttt cccccaccaa    2220
aaggctagag gtaaagctgt atccccctaa acttagggga gatactggag ctgaccatcc    2280
tgacctccta ttaaagaaaa tgagctgctg ccatctttg tgggcagtta gtcaggtgct    2340
gctctttgtg gtgtggtggg ctctggtctg ttctgctcgg tgctgggcct gggagcaaag    2400
attcccatgc ttggctacag atactgacag ctggcctctg aaggagggtg aaaacttctg    2460
cttgacagtt ccacatccat agtgcatggt ctgatgagtg cggttgctga catgggtttc    2520
ttggtaagct cctgaggtaa tggcagcctc                                    2550
```

<210> SEQ ID NO 9
<211> LENGTH: 20
<212> TYPE: DNA
<213> ORGANISM: Artificial Sequence
<220> FEATURE:
<223> OTHER INFORMATION: POLG forward primer

<400> SEQUENCE: 9
gagaaggccc agcagatgta                                                 20

<210> SEQ ID NO 10
<211> LENGTH: 18
<212> TYPE: DNA
<213> ORGANISM: Artificial Sequence
<220> FEATURE:
<223> OTHER INFORMATION: POLG reverse primer

<400> SEQUENCE: 10
atccgacagc cgatacca                                                   18

-continued

```
<210> SEQ ID NO 11
<211> LENGTH: 20
<212> TYPE: DNA
<213> ORGANISM: Artificial Sequence
<220> FEATURE:
<223> OTHER INFORMATION: POLG2 forward primer

<400> SEQUENCE: 11
gagctgttga cggaaaggag                                                     20

<210> SEQ ID NO 12
<211> LENGTH: 20
<212> TYPE: DNA
<213> ORGANISM: Artificial Sequence
<220> FEATURE:
<223> OTHER INFORMATION: POLG2 reverse primer

<400> SEQUENCE: 12
gttcttccgc aactctacgc                                                     20

<210> SEQ ID NO 13
<211> LENGTH: 20
<212> TYPE: DNA
<213> ORGANISM: Artificial Sequence
<220> FEATURE:
<223> OTHER INFORMATION: Long HTRA3 reverse primer

<400> SEQUENCE: 13
atgcggacga tcacaccaag                                                     20

<210> SEQ ID NO 14
<211> LENGTH: 19
<212> TYPE: DNA
<213> ORGANISM: Artificial Sequence
<220> FEATURE:
<223> OTHER INFORMATION: Long HTRA3 reverse primer

<400> SEQUENCE: 14
cgctgccctc cgttgtctg                                                      19

<210> SEQ ID NO 15
<211> LENGTH: 20
<212> TYPE: DNA
<213> ORGANISM: Artificial Sequence
<220> FEATURE:
<223> OTHER INFORMATION: Short HTRA3 forward primer

<400> SEQUENCE: 15
gagggctggt cacatgaaga                                                     20

<210> SEQ ID NO 16
<211> LENGTH: 18
<212> TYPE: DNA
<213> ORGANISM: Artificial Sequence
<220> FEATURE:
<223> OTHER INFORMATION: Short HTRA3 reverse primer

<400> SEQUENCE: 16
gctccgctaa tttccagt                                                       18

<210> SEQ ID NO 17
<211> LENGTH: 20
<212> TYPE: DNA
<213> ORGANISM: Artificial Sequence
<220> FEATURE:
<223> OTHER INFORMATION: HTRA2 forward primer
```

```
<400> SEQUENCE: 17
tttgccatcc cttctgatcg                                               20

<210> SEQ ID NO 18
<211> LENGTH: 20
<212> TYPE: DNA
<213> ORGANISM: Artificial Sequence
<220> FEATURE:
<223> OTHER INFORMATION: HTRA2 reverse primer

<400> SEQUENCE: 18
acaccatgct gaacatcggg                                               20
```

METHODS FOR IN VITRO INVESTIGATING MITOCHONDRIAL REPLICATION DYSFUNCTION IN A BIOLOGICAL SAMPLE, KITS AND USES THEREOF, THERAPEUTIC METHODS AGAINST PROGEROID-LIKE SYNDROMES OR SYMPTOMS AND SCREENING METHOD FOR IDENTIFYING PARTICULAR PROTEASE INHIBITOR(S) AND/OR NITROSO-REDOX STRESS SCAVENGER COMPOUND(S)

SEQUENCE LISTING

The instant application contains a Sequence Listing which has been submitted electronically in ASCII format and is hereby incorporated by reference in its entirety. Said ASCII copy, created on May 5, 2017, is named B10292A.txt and is 41,124 bytes in size.

The present invention relates to the field of in vitro testing methods for investigating impaired mitochondrial DNA (mtDNA) replication phenomema in biological samples collected from individuals, animals or humans, and in particular relates to methods that can be applied to the monitoring and/or diagnosing of the health status of a subject susceptible of suffering from physiological ageing (also referred to as chronological ageing or organismal ageing herein), or physiopathological ageing, in particular premature ageing or accelerated ageing or of a progeroid syndrome, such as Cockayne syndrome (CS), or neurodegenerative disorders or symptoms thereof. The invention also relates to kits for performing the methods of the invention and their uses.

The present invention also relates to a method for treating or delaying the symptoms of a subject suffering from physiological ageing or pathophysiological ageing, in this last case in particular premature ageing or accelerated ageing, or of a progeroid syndrome, such as Cockayne syndrome (CS), or neurodegenerative disorders, through administration of protease inhibitor(s), in particular serine protease inhibitor(s), having influence on the pathways associated with mtDNA replication, dysfunction and/or mismanagement of oxidative stress at the mitochondrial level, in particular defective pathways leading to abnormal levels of the functional POLG entity as defined hereafter, more particularly to the functional POLG1 protein, in particular abnormally low levels of POLG1 protein.

The present invention also relates to a nitroso-redox stress scavenger compound for use in a patient in need thereof to treat or delay Cockayne syndrome (CS) or symptoms thereof, and/or restore level(s) of protein(s) as disclosed herein, in particular to treat or delay Cockayne syndrome (CS) or symptoms thereof, said nitroso-redox stress scavenger compound being, according to a particular embodiment, MnTBAP.

The present invention also relates to a screening method for identifying particular protease inhibitor(s) and/or nitroso-redox stress scavenger compound(s) of interest within the context of the invention.

The present invention is of particular relevance in the context of diseases and symptoms directly associated with physiological ageing or physiopathological ageing, in particular premature ageing syndromes, especially progeroid syndromes—such as Cockayne syndrome (CS)—, which are a group of diseases all characterized by signs of premature ageing, and in the context of analysis of mitochondrial dysfunctions associated either with precocious ageing or observed during the onset and the establishment of neurodegenerative disorders.

The present invention relies on experiments emphasizing the relevance of the pathways associated with the management of oxidative stress in altered cells, in particular at the mitochondrial level.

Cockayne syndrome (CS), (OMIM entry 216400 http://www.omim.org/entry/216400, OMIM entry 133540 http://www.omim.org/entry/133540), also called Weber-Cockayne syndrome or Neill-Dingwall syndrome, is a rare genetic disorder characterized by neurological abnormalities and several growth and developmental defects, which include photosensitivity, hypersensitivity to oxidative damage, skeletal abnormalities, hearing loss, pigmentary retinopathy, progressive neurological disorders, mental retardation and premature ageing[1].

CS is an autosomal recessive disorder with an incidence of 1 per 2.7 million births in western Europe[2]. The incidence is extremely high in immigrant populations, likely for the consanguineous marriages[2].

CS is due to mutation in genes CSA (or ERCC8)[3] and/or CSB (or ERCC6)[4], which are required for nucleotide excision repair (NER), a DNA repair mechanism that removes bulky DNA adducts such as UV-induced DNA damage. About 70% of identified CS patients carry a mutation in CSB[5]. In particular, CSB is implicated in a sub type of NER, TC-NER (or transcription-coupled NER) also called TCR, that acts specifically on lesions located on the transcribed strand of expressed genes[6]. The other NER subtype GG-NER (or global genome NER) acts anywhere throughout the genome, and is normal in CS patients. The absence of TCR in cells treated by genotoxic agents leads to apoptosis. Mutations in the CSA or CSB genes are known to affect the proper performance repair of altered DNA structures resulting from UV damage, via transcription-coupled nucleotide excision repair (TC-NER) pathway. In a CS diagnosis situation however, the situation is complicated by the fact that some mutations in CSA exist, which affect the TC-NER pathway but do not affect the oxidative stress response, and are accordingly associated with a much milder syndrome (UV-sensitivity syndrome, $UV^S S$) with no sign of precocious ageing[11].

There are at least two forms of CS: type I, which is characterized by normal foetal growth and abnormalities appearing in the first two years or later and degeneration between 10-20 years, and type II, which is associated with little neurological development early after birth and death usually during the first decade.

It is important to note that currently neither large-scale diagnosis method nor a pre-natal test exists for CS, other than genotyping for CSA and CSB mutations. In spite of the devastating phenotype of CS, to date there is no indication of relevant, and easy to detect, cellular alterations in CS cells compared to $UV^S S$ and to normal cells.

According to another aspect, the Cockayne syndrome (CS) may be characterized by two major impairments, which are related to each other: appearance of premature ageing and neurological/developmental abnormalities.

In relation to these impairments, CS patients also display a variety of symptoms that include short stature, failure to gain weight and to thrive, microcephaly, hearing loss, eye abnormalities, severe tooth decay, bone abnormalities, and changes in the brain that can be detected on brain scans. These patients are also very sensitive to sun light (photosensitivity).

CS defects are strictly related to each other in a way that no indication enables to uncouple any of these defects from the other. Thus, treatments or conditions that alleviate or rescue the CS defects would be expected to act on multiple if not all the symptoms of CS. It happens that nervous cells and the nervous system are amongst the most sensitive targets of the CS impairment. Therefore treatments expected to act on CS can be advantageously considered both in the context of premature ageing and neurological abnormalities. Including the nervous system in the paradigm of CS results in an appropriate understanding and consequently enables the possibility of an appropriate care of this disease.

Therefore treatments that reverse or alleviate critical molecular impairment(s) in cells from individuals with CS, i.e., CS cells herein, extend to the cells of the nervous system, which are systematically included. It also has to be noted that to date, there is no perfect model to study neurodegenerative diseases in laboratory. In particular, analysis and treatment on, in particular, fibroblast cells, can be considered as representative of the impact of the same on neuron-type cells for CS-related alterations.

In addition, alterations observed in the premature ageing syndromes are considered to be representative, although at a much faster rate, of physiological deteriorations occurring during normal, i.e., physiological ageing, which includes neurodegeneration. Consequently, treatment(s) that reverse, at least partly, these impairments in disease should also be intended in the context of deteriorations due to normal ageing and neurodegeneration.

Turning to the molecular mechanism(s) involved in the CS, the current prevalent view is that TC-NER is impaired in CSA and CSB mutants, which results in the inability to repair the DNA lesions or clearing stalled RNA polymerase II in front of DNA damage, thereby blocking transcription after UV damage resulting in global transcription arrest. However, it seems that CSB-mutated cells, which have been extensively studied, have a transcription defect beyond the TC-NER impairment[7]. In this context, CSB appears as a transcription factor implicated in the activation of several genes and networks.

The severe phenotype of CS patients is however hard to reconcile with a sole defect in TC-NER and transcription[7].

In fact, CSB cells, i.e. cells from patients known to have an impaired CSB gene, as disclosed in Nardo et al, 2009 PNAS 106 (15): 620914, are also hypersensitive to oxidative damage. Indeed CSA and CSB appear to be involved in the repair of oxidative DNA lesions, produced by endogenous reactive oxygen species and normally repaired by the base excision repair (BER) pathway[8]. CSA/CSB modulate the BER pathway by direct interaction with BER proteins, and also by modulating the expression of BER genes. Both nuclear and mitochondrial BER are involved. Indeed CSA and CSB have been detected not only in the nucleus, but also in mitochondria[9, 10]. The implication of CSA/CSB in the repair of oxidative stress could explain developmental defects and the neurological degeneration observed in CS. However, the impairment of BER due to CSA or CSB deficiency is mild, suggesting an additional role of the CS proteins in the response to oxidative stress and more in general in the etiology of CS[8].

Interestingly, a mutation in CSA has been associated with the UV-sensitive syndrome ($UV^S S$), an autosomal recessive disorder characterized by mild cutaneous symptoms and defective TC-NER, but not with other symptoms of the CS, in particular no hypersensitivity to oxidative damage and no precocious ageing[11]. Thus defects in TC-NER and oxidative damage repair have been uncoupled in the phenotype of CSA mutations, suggesting that much of CS symptoms are due to the management of oxidative stress rather than to transcription-related DNA repair.

In fact, defects in NER are associated not only with CS, but also with xeroderma pigmentosum (XP), characterized by increased sensitivity to tumors in sun-exposed areas of the skin, and trichothiodystropy (TTD), characterized by developmental and neurological abnormalities, and premature ageing[12]. CS and TTD are cancer-free disorders. XP and TTD are essentially associated with defective GG-NER[12].

More generally, Cockayne syndrome is considered to pertain to progeroid syndromes, which are a group of diseases all characterized by signs of premature ageing. These syndromes include: Hutchinson-Guilford progeria syndrome (HGPS), Werner syndrome (WS), Bloom syndrome (BS), Rothmund-Thomson syndrome (RTS), Fanconi anemia (FA), Ataxia telangiectasia (A-T), Cockayne syndrome (CS), Xeroderma pigmentosum (XP) and trichothiodystropy (TTD)[13].

Several of these syndromes are classified as segmental progeroid syndromes as multiple organs and tissues replicate phenotypes associated with normal ageing[14].

HGPS and WS are two of the best characterized human progeroid diseases[15]. HGPS, which is one of the most severe forms of progeria, has an incidence of 1 in 4-8 million births and distinct clinical symptoms are developed during the first year of life, and patients die at a median age of 11-13 years. HGPS is also called "progeria of the childhood". WS has an incidence of 1 per million births (but 1:100,000 in Japan), and Werner heterozygotes are $^1/_{180}$ in the general population. Symptoms appear in the first-second decade and the life expectancy reaches 47-54 years. WS is also called "progeria of the adult".

Most progeroid syndromes include defects in distinct repair systems such as NER, BER, and double strand break repair (DSB)[13, 15]. The exact mechanism(s) by which these mutations lead to progeria is/are not known yet. Moreover, the extent of progeria is different among these syndromes. At present, there is no also no indication why mutation in some genes result in more severe progeria syndromes than mutations in other genes.

HGPS is mutated in LMNA that encodes for the four different types of lam ins. Mutations activate a cryptic splice site that lead to deletion of 50 aminoacids (the deleted protein is called progerin) that cannot undergo further processing. Lamins constitute the major component of the nuclear lamina, which provide structure and shape to the nucleus and are also involved in chromatin organization and DNA replication, transcription, and repair. The prevalent view is that lamin mutations lead to deficient DNA damage response, probably by sequestering replication and repair factors, leading to stalled DNA replication forks that collapse into DSBs. Moreover, lamin defects would increase DNA damage signalling at the level of telomeres and reduce the telomere length, leading to early cell senescence.

The Werner syndrome is associated with mutation of WRN, an ATPase-helicase (of the family of RECQ helicases, which unwinds the DNA double strands by hydrolyzing ATP). WRN protein is involved in DNA replication, recombination and telomere maintenance and its impairment results in chromosomal aberrations.

The Bloom syndrome and the Rothmunds-Thomson syndrome are due to mutation in the RECQ helicases BLM and RECQ4, respectively. As with the WRN helicase, the RECQ4 and BLM helicases are necessary to maintain genome integrity, but they differ in their functions and in their interaction partners[16]. Bloom syndrome is characterized by a very high level of spontaneous sister chromatid exchanges (SCE).

At least 16 genes responsible for the Fanconi anemia have been identified, and they are all linked to a DNA damage signalling pathway (the FA pathway) that is activated in response to DNA damage, in particular DSBs. Eight FA proteins form a nuclear-localized complex with E3 ubiquitin ligase and thereby catalyze monoubiquitination in target proteins. This monoubiquitination does not lead to proteasomal degradation but it can alter cellular localization or the function of the target protein.

Ataxia-telangiectasia is due to mutation in the ATM gene, a serine threonine kinase that is important at the level of DNA damage (in particular DSB) signalling and activation of DNA repair mechanisms.

All progeroid diseases display clinical features mimicking physiological ageing at an early age. They might provide insights into the process of normal human ageing and/or dysfunctions linked to normal human ageing (also referred to as physiological or chronological or organismal ageing herein), which is itself characterized by dysfunction of several physiological processes, as well as insights into physiopathological ageing, in particular premature ageing, as disclosed herein[15].

By "early age" within the expression "physiological ageing at an early age" recited above, it is meant an age that is earlier than the age of normal onset of the symptoms of physiological ageing or an age that is not consistent with increased frequency of a condition or a disease that is generally related to aging.

Clinical symptoms of physiological ageing or physiopathological ageing, in particular premature aging, include skin atrophy with loss of cutaneous elasticity, dysfunction of cutaneous appendices, degeneration of the central nervous system, neurodegenerative symptoms, diabetes mellitus, changes in the volume of the adipose tissue, pigmentary changes with hyper- and hypopigmentation of the skin (poikiloderma), regional skin fibrosis, premature hair graying or hair loss, osteoporosis, and in certain cases tumors typical of those seen in patients of older age[13]. These symptoms are also associated with physiological ageing, although they appear at a later age in normal individuals.

In this context, inventors' investigations focused on the mechanism(s) underlying the etiology of CS in particular, which are also applicable to all diseases displaying symptoms of physiological ageing or physiopathological ageing, in particular premature ageing. These investigations have put in light dysfunctional mitochondrial pathways, in particular associated with ageing in general, and a completely new mechanism that may in particular explain defects in CS cells.

Back to the considerations introduced above regarding the management of oxidative stress, mitochondria are largely responsible for the production of oxidative stress, and CS patients are highly sensitive to oxidative damage. Oxidative damage is known to affect replication and transcription of mitochondrial DNA resulting in a decline of the mitochondrial function[18]. A large set of data suggests that oxidative damage is also associated with physiological ageing.[18] Therefore, alterations in syndromes of precocious ageing like CS are considered informative also for understanding physiological ageing, since they recapitulate the dysfunction(s) observed in physiological ageing (Dreesen and Stewart, 2011 Aging, 3:889-895; Scaffidi and Misteli, 2006 Science 312: 1059-1063).

The present invention is based on the findings of new elements paving the way to a better diagnosis and treatment of symptoms of physiopathological ageing, in particular premature ageing or accelerated ageing or diagnosis and treatment of progeroid syndrome(s), such as Cockayne syndrome (CS), or neurodegenerative disorders or associated symptoms.

The invention therefore relates to an in vitro method for investigating mtDNA replication dysfunction (defective mtDNA replication or, differently said, mtDNA replication impairment or dysfunction of the mtDNA replication apparatus and/or machinery) in a biological sample removed from a subject susceptible of suffering from physiological ageing or physiopathological conditions related to physiological ageing, or physiopathological ageing or associated symptoms or conditions, in particular premature ageing or accelerated ageing, or of a progeroid syndrome, such as Cockayne syndrome (CS), or neurodegenerative disorders or symptoms thereof, said method comprising the steps of:

a. contacting said biological sample with at least one marker specific for at least one species selected in the group of: POLG1 protein, POLG1 RNA, POLG2 protein, protease(s) which have POLG as a target, in particular serine protease(s) such as HTRA3 protein, HTRA2 protein and, HTRA3 RNA, HTRA2 RNA or any combination of these species, in conditions enabling said marker(s) to react with their respective targets (in particular, species), and b. determining the level of at least one species selected in step a) from the group of: POLG1 protein, POLG1 RNA, POLG2 protein, protease(s) which have POLG as a target, in particular serine protease(s) such as HTRA3 protein, HTRA2 protein, and HTRA3 RNA, HTRA2 RNA or any combination of these species in said biological sample through measurement of the marker(s) that has(have) reacted with its (their) respective species in step a), or through measurement of the reaction product(s) obtained after reacting the marker(s) with its (their) respective species in step a), and c. comparing the level(s) determined in step b) with respective normal threshold value(s) determined for healthy subject(s) for each species selected in the group set forth in step a) and b) to carry out said steps, and d. from the comparison made in step c), concluding about the existence of a dysfunction in mtDNA replication.

Within the context of the invention, it has been shown by the inventors that dysfunctional mtDNA replication can be correlated to the observed levels of the expressed POLG entity, as defined herein, in particular the expressed POLG1 or POLG1 and POLG2, although not due to a mutation affecting the POLG entity in way rendering this entity, in particular the POLG1 protein or POLG1 and POLG2, dysfunctional in themselves. It is documented that mutations affecting POLG are associated to mtDNA depletion syndromes. However, within the context of the invention, impaired mtDNA replication due to reduced level of the key replicating enzyme (which otherwise works well), which is POLG1, can be evidenced.

Mitochondrial DNA replication is catalyzed by a mitochondria-specific mitochondrial complex comprising the so-called mitochondrial DNA polymerase gamma (γ) holoenzyme, which is an heterotrimer consisting of a single 140 kDa catalytic unit (encoded by the POLG1 gene at the nuclear chromosomal locus 15q25) and a 55 kDa accessory subunit that forms a tight dimer (encoded by the POLG2 gene at nuclear chromosomal locus 17q).

The POLG1 protein (SEQ ID NO:1) (NCBI Reference POLG1: Gene ID 5428 http://www.ncbi.nlm.nih.gov/gene/ 5428, Primary source HGNC: 9179, POLG1 protein NCBI Reference Sequence: NP_001119603.1 http:// www.ncbi.nlm.nih.gov/protein/NP_001119603.1) is therefore the catalytic subunit of the so-called mitochondrial DNA polymerase gamma (γ), needed for mtDNA replication. The POLG1 protein is also referred to in the literature under the common name POLG, or POLGA (see the synonymy annotation at http://www.ncbi.nlm.nih.gov/ gene/?term=NP_001119603.1). Human POLG1 (SEQ ID NO:2) is discussed in Stumpf and Copeland, 2011, Cell. Mol. Life Science 68:219-233 or Ropp & Copeland, 1996 Genomics 36:449-458. As shown on page http://www.ensembl.org/Homo_sapiens/Gene/Fam ily?family=ENSFM006100009647 34;g=ENSG00000140521;r=15:89859534-89878092, there are several protein transcripts (splicing variants) corresponding to human POLG1. Accordingly, by POLG1 protein as referred to herein, it is meant the native form of the protein having a sequence as disclosed in databases and/or literature and/or herein, but also isoforms or variants thereof having a polypeptidic sequence showing 60% or 70% or 80% or 90% or 95% and up to 99% identity with the polypeptidic sequence of the native POLG1 protein.

POLG2 protein (SEQ ID NO:3) (NCBI Reference POLG2: Gene ID 11232 http://www.ncbi.nlm.nih.gov/gene/ 11232, Primary source HGNC: 9180, POLG2 protein NCBI Reference Sequence: NP_009146.2 http://www.ncbi. nlm.nih.gov/protein/NP_009146.2), also called mitochondrial DNA polymerase subunit gamma-2, is a protein that in humans is encoded by the POLG2 gene, and is an accessory protein that increases the processivity of the catalytic subunit of the POLG protein. The POLG2 protein is also referred to in the literature under the common name POLGB (see the synonymy annotation at http://www.ncbi.nlm. nih.gov/gene/?term=NP_009146.2). Human POLG2 (SEQ ID NO:4) is discussed in Young et al, 2011 Human Molecular Genetics 20 (15): 3052-3066. As shown on page http:// www.ensembl.org/Homo_sapiens/Gene/Fam ily/ Genes?cdb=compara;db=core; family=ENSFM00250000007196; g=ENSG00000256525; r=17:62473902-62493154, there are several protein transcripts (splicing variants) corresponding to human POLG2. Accordingly, by POLG2 protein as referred to herein, it is meant the native form of the protein having a sequence as disclosed in databases and/or literature and/or herein, but also isoforms or variants thereof having a polypeptidic sequence showing 60%, 70% or 80% or 90% or 95% and up to 99% identity with the polypeptidic sequence of the native POLG2 protein.

When reference is made herein to the POLG entity, reference is made to the POLG1 protein, or the POLG2 protein, or both.

HTRA3 protein (SEQ ID NO:5) (NCBI Reference HTRA3: Gene ID 94031 http://www.ncbi.nlm.nih.gov/gene/ 94031, Primary source HGNC: 9180, HTRA3 protein NCBI Reference Sequence: NP_444272.1 http://www.ncbi. nlm.nih.gov/protein/NP_444272.1) is a serine peptidase (or serine protease) that is a member of the mammalian HTRA family. Human HTRA3 (SEQ ID NO:6) and human HTRA3 are discussed in Nie et al, 2003 Biochemical Journal 371: 39-48 or Narkiewicz et al, 2009 Oncology reports 21: 1529-1237. As shown on page http://www.ensembl.org/ Homo_sapiens/Transcript/Summary?db=core; g=ENSG00000170801; r=4:8271492-8308838; t=ENST00000307358, there are several protein transcripts (splicing variants) corresponding to human HTRA3. More particularly, there are two (2) transcripts for HTRA3 (different splicing), giving a long (L) and a short (S) form, which are both discussed herein. Accordingly, by HTRA3 protein as referred to herein, it is meant the native form of the protein having a sequence as disclosed in databases and/or literature and/or herein, but also isoforms or variants thereof having a polypeptidic sequence showing 60%, 70% or 80% or 90% or 95% and up to 99% identity with the polypeptidic sequence of the native HTRA3 protein.

In a particular embodiment, the conclusion of step d) of the method of investigating the existence of a mtDNA replication dysfunction of the invention is made if the level of each species selected to carry out the above disclosed steps is as follows:
  the level of POLG1 protein determined in step b) is decreased with respect to the normal threshold value introduced in step c) by at least 10%, and/or
  the level of POLG2 protein determined in step b) is increased with respect to the normal threshold value introduced in step c) by at least 15%, and/or
  the level of HTRA3 protein, in particular the long isoform of HTRA3 protein, and/or HTRA3 RNA determined in step b) is increased with respect to the normal threshold value introduced in step c) by at least 2 folds, or at least two of the above measurements meet the above thresholds.

By "mtDNA replication dysfunction", it is meant that mtDNA replication is altered or is totally impaired in cells of the assayed biological sample. This expression is used herein as a synonym of defective mtDNA replication or mtDNA replication impairment. Indeed, the inventors showed that in cells of a sample wherein mtDNA replication is dysfunctional, only the amount of the enzyme responsible for synthesizing of mtDNA that is POLG1, is lower or much lower than in healthy control cells. Moreover the mtDNA content and the levels of TFAM, which is a factor involved in mtDNA transcription and maintenance is generally altered in one sense or the other, indicating that, within the context of the invention, it is the process of mtDNA replication that is affected, and not POLG1 that is defective in itself. Finally, the inventors have also evidenced that ATP production by mitochondria is reduced in all tested CS samples that have POLG defects, showing that the mitochondrial function itself is affected in the tested cases. These methods may be used for demonstrating that mtDNA replication is impaired in a given assayed sample.

As a synonym for "mtDNA replication dysfunction" can also be used the expression "dysfunction of the mtDNA replication apparatus and/or machinery". Indeed, POLG1 is the key replication enzyme for mtDNA replication. If POLG1 declines, it is a fact that the replication apparatus is dysfunctional, as illustrated above. In addition, it is stated by the inventors that POLG1 decrease results in altered mtDNA content (essentially decrease but also increase). Therefore, there is a direct relationship between the levels of the species monitored within the present invention and the fact that mtDNA replication is impaired, which is also correlated with a dysfunctional mtDNA replication apparatus and/or machinery. Impaired mtDNA replication is indeed evidenced by a dysfunctional mtDNA replication apparatus and/or machinery, as illustrated above.

By "biological sample" it is meant a sample originating from the sampling of biological tissue(s) or fluid(s), especially body tissue(s) or fluid(s), which is therefore substantially constituted of cells, for example bodily fluid such as a cerebrospinal fluid, saliva, mucus, urine or blood sample, or include a cell lysate of the same origin, and/or include a conditioned culture medium, and is optionally derived from a tissue (e.g., a tissue homogenate), a biopsy.

In a particular embodiment, the assayed biological sample comprises or contains fibroblasts or culture(s) thereof, or consists of isolated cells, in particular fibroblasts, or culture(s) thereof. However, other cells should also be considered as much as they grow in culture or they are used as isolated cells from a biological sample (for example from a body fluid), as described above.

According to a particular embodiment, the in vitro method of the invention is used within a prenatal testing procedure, wherein the tested subject is an embryo or a fetus. In addition to samples generally used for this type of testing (such as amniotic tissue), it is also possible to test parent(s) material (such as fibroblasts, cells from biopsies). Parents may be heterozygotes for the CSA or CSB mutation and their POLG/HTRA3 values might be different from controls (and from CS). This seems indeed the case for the parent that the inventors have tested (CS358), as described herein, and who has no CS phenotype.

By "physiopathological ageing or associated symptoms or conditions, in particular premature ageing or accelerated ageing, or of a progeroid syndrome, such as Cockayne syndrome (CS), or neurodegenerative disorders or symptoms thereof", it is meant all conditions disclosed above and herein, which are not clinically consistent with the age of the subject, in particular a condition resulting in skin atrophy with loss of cutaneous elasticity, dysfunction of cutaneous appendices, degeneration of the central nervous system, neurodegenerative symptoms, diabetes mellitus, changes in the volume of the adipose tissue, pigmentary changes with hyper- and hypopigmentation of the skin (poikiloderma), regional skin fibrosis, premature hair graying or hair loss, osteoporosis, muscle atrophy, weight loss, alopecia, kyphosis, anaemia, reduced fertility, and in certain cases tumors typical of those seen in patients of older age, as well as symptoms typical of neurodegenerative disorders like ophthalmoplegia, ataxic neuropathy, inflammation, cerebellar ataxia, cachexia, neuron loss, deterioration of cognitive and kinetic body response.

According to a particular embodiment, the methods and means described herein are applied to subjects undergoing physiological ageing or suffering therefrom, with related detrimental consequences on their health or their capabilities or appearance. In this context, "physiological ageing" or "physiopathological condition related to physiological ageing" means the deterioration of the physiological processes, which appears with the aging of a subject, i.e., in an extent compatible with the observations commonly made on persons subject to normal ageing, when their age is taken in account. In a more particular embodiment, the state of "physiological ageing" in a subject can be determined by symptoms of hair and/or skin damage, including loss of cutaneous elasticity and/or observation of hair and/or cutaneous alterations that are nevertheless in correlation with the age of the subject.

According to another particular embodiment, the methods and means described herein are applied to subjects susceptible of suffering from physiopathological ageing. In this context, "physiopathological ageing" means the deterioration of the physiological processes appearing in a subject, which can be qualified as going beyond the observations that can be made, in average, on normal subjects having around the same age, and not diagnosed with a health disorder or condition, than the observed subject. This category includes subjects having diseases as invalidating as diseases entering in the category of premature ageing or accelerated ageing, or of a progeroid syndrome, such as Cockayne syndrome (CS), or neurodegenerative disorders or symptoms thereof.

By "marker specific for at least one species selected in the group of: POLG1 protein, POLG1 RNA, POLG2 protein, protease(s) which have POLG as a target, in particular serine protease(s) such as HTRA3 protein, HTRA2 protein and, HTRA3 RNA, HTRA2 RNA", it is meant a marker suitable for directly or indirectly specifically revealing the qualitative and/or quantitative presence of, respectively, one of the following species: POLG1 protein, POLG1 RNA, POLG2 protein, protease(s) which have POLG as a target, in particular serine protease(s) such as HTRA3 protein, HTRA2 protein and, HTRA3 RNA, HTRA2 RNA when further performing detection methods, in particular methods such as immunofluorescence, Western Blotting, ELISA or a PCR-based amplification method, such as RT-qPCR.

The specificity of the marker is assessed with respect to its ability to react with its target but not to react in a detectable or in a functionally effective manner with other compounds of the sample.

For example, nucleotide probes specifically binding to DNAs or RNAs and carrying a ligand at one end, which is recognized by a specific antibody, have been developed. Molecular beacons (antisense nucleotide probes targeting DNA or RNA with a fluorophore and a quencher at opposite ends), which emit a signal when hybridizing their targets (and are thus detected by fluorescence) have also been developed. These embodiments are encompassed in the definition provided above with respect to the markers that can appropriately be used within the present invention.

In the case of, but not exclusively, proteins, in particular POLG1, POLG2, protease(s) as identified above, HTRA3, HTRA2, such marker(s) may be an antibody specific for said protein(s), in particular POLG2 and/or HTRA3 protein(s) or a combination of several antibodies altogether specific for said protein(s), and, optionally, one or several of secondary antibody(ies) or reagent(s) (such as dye(s)) to reveal a complex between specific antibody(ies) recited above and its (their) target.

In case of RNA determination, in particular POLG1 RNA or HTRA3 RNA, such marker(s) may be at least one pair of specific oligonucleotide primers specific for hybridization (by base pairing) with the cDNA corresponding to the RNA target (e.g. POLG1 or HTRA3 RNA) or at least one pair of specific oligonucleotide primers specific for directly hybridizing with the corresponding target RNA, and, optionally, at least one label or marker for detection of nucleic acids, in particular a dye detectable in a real-time PCR equipment, for revealing the HTRA3 RNA or cDNA marker. According to a particular embodiment, the pair of specific oligonucleotide primers that is used is capable to hybridize both with the target RNA and the cDNA synthesized using the target RNA as a template.

According to a particular embodiment, protein(s) as defined above are detected together with RNA(s) as defined above, and use is made of a suitable combination of markers for this purpose: the markers used in combination can therefore, according to this embodiment, be all those mentioned above in all combinations thereof. They may in particular consist of at least one antibody specific for a protein selected amongst: POLG1, POLG2, HTRA3, HTRA2 or a combination of several antibodies specific respectively for POLG1, POLG2, HTRA3, HTRA2 and, at least one pair of specific oligonucleotide primers specific for hybridization with HTRA3 or POLG1 cDNA, and/or at least one pair of specific oligonucleotide primers specific for hybridization with HTRA3 RNA and/or POLG RNA or a combination of primer pairs specific for each of said HTRA3 or POLG1 cDNA or RNA.

A "marker specific for POLG1 protein" is a marker suitable for specifically targeting and optionally revealing the qualitative and/or quantitative presence of POLG1 protein when further performing, in particular, immunofluorescence, Western Blotting or ELISA detection methods.

In the case of POLG1 protein level measurement, such a marker may be an antibody specific for POLG1 protein or a combination of several antibodies specific for POLG1 protein, and, optionally, one or several secondary antibody(ies) or reagent(s) to reveal a complex between specific antibody(ies) recited above and its (their) target, as in particular described herein within the Materials and Methods section. Other markers may include detectable molecules having a binding capacity or interaction capacity with POLG1.

By "conditions enabling said marker(s) to react with their respective targets", it is meant either "conditions enabling a marker to react with its respective target RNA and/or cDNA", or "conditions enabling a marker to react with its respective target protein".

By "conditions enabling a marker to react with its respective target RNA and/or cDNA", it is meant conditions enabling hybridization of primers to their nucleic acid target(s) for further performing an amplification method, as known by a person skilled in the art and/or described in notices provided by manufacturers when commercial kits are used, as in particular described herein within the Materials and Methods section.

By "conditions enabling said marker to react with a protein", in particular the POLG1 protein, it is meant, in particular, but not exclusively, conditions enabling an immunological reaction to take place, as known by a person skilled in the art and/or described in notices provided by manufacturers when commercial kits and/or reagents are used, as in particular described herein within the Materials and Methods section.

By "measurement of the marker(s) that has(have) reacted with its (their) respective species it is therefore in particular made reference to the process of measurement of level(s) of protein(s), as described above, in particular by Immunofluorescence (IF), Western Blot or ELISA detection methods.

By "measurement of the reaction product(s) obtained after reacting the marker(s) with its (their) respective species", it is therefore in particular made reference to the process of measurement of level(s) of RNA(s), as described above, in particular as reflected by the amplification product obtained after performing a PCR-based amplification method, such as RT-qPCR, on said RNA present in the assayed sample.

By "determining the level of at least one species selected in step a) from the group of: POLG1 protein, POLG1 RNA, POLG2 protein, protease(s) which have POLG as a target, in particular serine protease(s) such as HTRA3 protein, HTRA2 protein, and HTRA3 RNA, HTRA2 RNA, or any combination of these species in said biological sample", it is meant obtaining an absolute or relative value representative of the amount of target species in the assayed sample, in particular by either:

interpreting the results (raw data or transformed data) obtained through immunofluorescence, Western Blotting or ELISA detection methods as mentioned above, or as described herein within the Materials and Methods section, in order to evaluate the amount of target protein present in the assayed sample, or interpreting the results (raw data or transformed data) obtained after performing a PCR-based amplification method, such as RT-qPCR, on nucleic acids present in the assayed sample, the level being deduced from the quantity of amplicons present after amplification and the amount of PCR cycles, as in particular described in the Material and Methods section herein.

In particular, by "determining the level of POLG1 protein", it is meant obtaining an absolute or relative value, in particular by interpretation of the results (raw data or transformed data) obtained through the immunofluorescence, Western Blotting or ELISA detection methods mentioned above, or as described herein within the Materials and Methods section, which is suitable for evaluating the amount of POLG1 protein present in the assayed sample.

It will be understood from the above that marker(s) used within the present invention to obtain level(s) of specific species(s) as disclosed herein, are means suitable for revealing, directly or not, said level(s), if necessary after further steps based on the formation of an immunological complex between a particular marker and its target (e.g. when antibodies or labeled antibodies or set of antibodies are used), and/or further steps based on the hybridization between a particular marker and a nucleic acid target (e.g. when primers are used), and subsequent nucleic acid amplification and counting, according to methods known in the art and/or disclosed herein.

According to a particular embodiment, the level of POLG1 protein determined in step b) is decreased with respect to the normal threshold value introduced in step c) by at least 10%, in particular when the detection method that is used is not immunofluorescence.

In a general manner, percentages are evaluated with respect to the unit value(s) appropriate in the method carried out for the described measurement(s).

According to a particular embodiment, the level of POLG1 protein determined in step b) is decreased with respect to the normal threshold value introduced in step c) by at least 20%, or at least 30% or at least 40%, and up to 80% or up to 90%, in particular when the detection method that is used is immunofluorescence staining.

According to a particular embodiment, the level of POLG2 protein determined in step b) is increased with respect to the normal threshold value introduced in step c) by at least 15%, in particular when the detection method that is used is not immunofluorescence.

According to a particular embodiment, the level of POLG2 protein determined in step b) is increased with respect to the normal threshold value introduced in step c) by at least 25%, or at least 35% or at least 45%, in particular when the detection method that is used is immunofluorescence staining.

According to a particular embodiment, the level of HTRA3 protein, in particular the long isoform of HTRA3 protein, and/or HTRA3 RNA determined in step b) is increased with respect to the normal threshold value introduced in step c) by at least folds, in particular when the detection method that is used is not immunofluorescence staining.

The level of increase with respect to a normal threshold value may depend on the quantification sensitivity of the detection method that is used.

According to a particular embodiment, the level of HTRA3 protein, in particular the long isoform of HTRA3 protein, and/or HTRA3 RNA determined in step b) is increased with respect to the normal threshold value introduced in step c) by at least 5 folds, or at least 10 folds, in particular when the detection method that is used for detecting the level of HTRA3 protein is immunofluorescence staining. In a specific embodiment, said level of HTRA3 is increased by at least 50 or at least 60 or at least 70 folds when the detection method that is used is immunofluorescence staining. In a particular embodiment, the inventors found huge increase of HTRA3 RNA (2 to 160-fold) and HTRA3 protein by IF (60 to 3000-fold). However, when RT-qPCR is used for detecting RNA, obtained values may be lower, which is consistent with the fact that as one single RNA molecule can be used to produce multiple proteins. Therefore, according to a particular embodiment wherein the level of HTRA3 RNA is determined, if necessary in all combination(s) with other parameter(s) (in particular, species) as disclosed herein, said level of HTRA3 RNA determined in step b) is increased with respect to the normal threshold value introduced in step c) by at least 2 folds.

According to particular embodiments, all the levels indicated above can be used in combination, in particular when meeting the above-mentioned thresholds, for concluding according to the explanations provided herein and/or deducible by a person skilled in the art.

By "normal threshold value(s) determined for healthy subject(s) for POLG" it is meant level(s) of POLG protein found by assaying one biological sample from an healthy subject or alternatively found by assaying several biological samples from several distinct healthy subjects, the resulting normal threshold value being then determined as the mathematical mean of the levels of POLG protein values of all the assayed healthy subjects biological samples, or alternatively found by assaying a pool of biological samples from several distinct healthy subjects.

According to another embodiment, an in vitro method for investigating mtDNA replication dysfunction of the invention also encompasses determination of the level(s) of other markers (and consequently, species), which are: POLG2 protein, protease(s) which have POLG1 as a target in a sample provided in conditions enabling said marker to react with said protease(s), in particular serine protease(s) such as HTRA3 protein, HTRA2 protein, or a marker specific for HTRA3 RNA or HTRA2 RN A in a sample provided in conditions enabling said marker to react with their respective RNA target, as an additional parameter (species) to POLG1 level determination or as an alternative to a determination of the level of POLG1 protein.

Such markers may be an antibody specific for a protein selected amongst: POLG2 and/or HTRA3 and/or HTRA2 or a combination of several antibodies specific for POLG2 and/or HTRA3 and/or HTRA2, and, optionally, one or several of secondary antibody(ies) or reagent(s) to reveal a complex between specific antibody(ies) recited above and its (their) target.

In case of HTRA3 RNA determination, such a marker may be at least one pair of specific oligonucleotide primers specific for hybridization with HTRA3 cDNA or at least one pair of specific oligonucleotide primers specific for hybridization with HTRA3 RNA, and, optionally, at least one label or marker for detection of nucleic acids, in particular a dye detectable in a real-time PCR equipment, for revealing the HTRA3 RNA or cDNA marker.

According to a particular embodiment, the in vitro method for investigating mtDNA replication dysfunction of the invention encompasses a determination of any combination of the above-mentioned species, in particular a combination of POLG1 and POLG2 or a combination of determination of POLG1 and HTRA3 or a combination of determination of determination of POLG1, POLG2 and HTRA3.

According to a particular embodiment, the in vitro method for investigating mtDNA replication dysfunction of the invention encompasses a determination of any combination of the above-mentioned species, in particular a combination of determination of POLG1 and HTRA3 and optionally HTRA2 or a combination of determination of POLG1, POLG2 and HTRA3 and optionally HTRA2.

In a specific embodiment, the method of the invention comprises, in addition to a determination if the level(s) of POLG1 protein, the steps of:
a. further contacting the assayed biological sample with any one of the following markers: a marker specific for POLG2 protein in conditions enabling said marker to react with POLG2 protein, a marker specific for protease(s) which have POLG as a target in conditions enabling said marker to react with said protease(s), in particular serine protease(s) such as HTRA3 protein, HTRA2 protein, a marker specific for HTRA3 RNA in conditions enabling said marker to react with HTRA3 RNA, a marker specific for HTRA2 RNA in conditions enabling said marker to react with HTRA2 RNA, or any combination of these markers and/or species, and
b. further determining the level of the marker selected in step a) from the group of: POLG2 protein, protease(s) which have POLG as a target, in particular serine protease(s) such as HTRA3 protein, HTRA2 protein and HTRA3 RNA or THRA2 RNA or any combination of these markers and/or species through measurement of the marker(s) that has(have) reacted with its (their) respective species(s) in step a), or though measurement of the reaction product(s) obtained after reacting the marker(s) with its (their) respective species(s) in step a), and
c. comparing the levels determined in step b) with respective normal threshold value(s) determined for healthy subject(s) for each species set forth in step b), and
d. from the comparison made in step c), concluding about the existence of a dysfunction in mtDNA replication.

POLG2 protein or HTRA3, or HTRA2 protein level(s) may be determined by immunofluorescence, by Western Blotting or by ELISA testing. The level(s) of HTRA3 or HTRA2 RNA or POLG transcripts may be determined by reverse transcription polymerase chain reaction (RT-qPCR).

According to another particular embodiment, the conclusion of steps d) above of the existence of a mtDNA replication dysfunction is made if the level of each species selected to carry out the above disclosed steps is as follows:
the level of POLG1 protein determined in step b) is decreased with respect to the normal threshold value introduced in step c) by at least 20% to up to 90% when the level of POLG1 protein is determined by immunofluorescence, and/or
the level of POLG2 protein determined in step b) is increased with respect to the normal threshold value introduced in step c) by at least 25% when the level of POLG2 protein is determined by immunofluorescence, and/or
the level of HTRA3 protein, in particular the long isoform of HTRA3 protein, and/or HTRA3 RNA determined in step b) is increased with respect to the normal threshold value introduced in step c) by by at least 10 folds for HTRA3 protein and at least 2 folds for HTRA3 RNA when the levels are determined by immunofluorescence or a dye detectable in a real-time PCR equipment, or
at least two of the above measurements meet the above thresholds.

In another aspect of the method of the invention, the level of POLG1 transcripts (synonym for POLG1 RNAs) is also determined and compared with a normal threshold value determined for healthy subject(s), conclusion being made of the existence of a mtDNA replication dysfunction if the level of POLG1 protein is decreased with respect to the normal threshold value by at least 10%, in particular at least 20%, especially when immunofluorescence is used for detection, and the level of POLG1 transcripts is within the range of normal threshold value determined for this species on normal (in particular non CS) cells, in combination with another species or not.

Indeed, the inventors particularly found out that, in cells of CS patients, the levels of POLG1 RNA do not change compared to controls, in contrast to POLG1 protein levels. This indicates that variation in POLG1 protein level results from degradation of the protein (likely due to the action of proteases, in particular HTRA3) rather than its insufficient expression.

Moreover, it is surprising that in CS cells, where POLG1 protein levels are low, the corresponding RNAs level is normal. Therefore, a double check with these two species enables to be quite confident that variation in POLG1 protein level does not result from mutation(s) affecting PolG1 gene but rather POLG1 protein degradation after it is expressed.

As a consequence, the invention also relates to an in vitro method for investigating mtDNA replication dysfunction in a biological sample removed from a subject susceptible of suffering or suffering from Cockayne syndrome (CS), or symptoms thereof, said method comprising the steps of:
a. contacting said biological sample with a marker specific for POLG1 RNA, in conditions enabling said marker(s) to recognize and optionally react with its target, and
b. determining the level of POLG1 RNA in said biological sample, and
c. comparing the level(s) determined in step b) with a normal threshold value determined for healthy subject(s) for POLG1 RNA, and
d. from the comparison made in step c), concluding about the existence of a dysfunction in mtDNA replication if the level of POLG1 RNA is within the range of the normal threshold value determined for this species on normal cells in step c).

According to an aspect of the invention, a marker for revealing the level of POLG1 transcripts (synonym for POLG1 RNAs) may be at least one pair of specific oligonucleotide primers specific for hybridization with POLG1 cDNA, or at least one pair of specific oligonucleotide primers specific for hybridization with POLG1 RNA, and, optionally, at least one label or marker for detection of nucleic acids, in particular a dye detectable in a real-time PCR equipment. In this respect, the Material and Methods section provides examples of such markers or dyes that may suitably be used.

Performing the above method involving a marker specific for POLG1 RNA also enables performing a cross check that can be used, if necessary, in combination with other parameters (in particular, species) enabling to partially investigate mtDNA replication dysfunction, in particular in a biological sample removed from a subject susceptible of suffering or suffering from Cockayne syndrome (CS), or symptoms thereof, and ultimately investigate the occurrence of CS in a subject. Other parameters may be the protein level(s)) disclosed herein. The above method involving a marker specific for POLG1 RNA may be performed according to all the features disclosed herein.

The invention also encompasses a method, for monitoring or diagnosing the health status of a subject susceptible of suffering from physiological ageing, or physiopathological or accelerated ageing or a progeroid syndrome, such as Cockayne syndrome (CS), or neurodegenerative disorders or symptoms thereof, said method comprising performing the method of determination of defective mtDNA replication as disclosed above encompassing the determination of POLG1 and alternatively or optionally one or several other species as disclosed herein and further comprising the following step:
e. concluding about the health status of a subject from which the tested biological sample has been removed on the basis of the existence of a mtDNA replication dysfunction.

According to a particular embodiment, the conclusion is the presence or a risk of occurrence or of a presence of physiological or accelerated ageing or a progeroid syndrome, such as Cockayne syndrome (CS), or neurodegenerative disorders or symptoms thereof if conclusion is made of the existence of a mtDNA replication dysfunction.

In particular embodiments of the invention, the assayed biological sample is from a subject in need of being and/or diagnosed with physiological or accelerated ageing or a progeroid syndrome, such as Cockayne syndrome (CS), or neurodegenerative disorders or symptoms thereof, and/or a subject having a family history of physiological or accelerated ageing or progeroid syndrome(s), such as Cockayne syndrome (CS), or neurodegenerative disorders or symptoms thereof.

Progeroid syndromes referred to above may be selected amongst: Hutchinson-Guilford progeria syndrome (HGPS), Werner syndrome (WS), Bloom syndrome (BS), Rothmund-Thomson syndrome (RTS), Fanconi anemia (FA), Ataxia telangiectasia (A-T), Cockayne syndrome (CS), Xeroderma pigmentosum (XP) and trichothiodystropy (TTD), and the neurodegenerative disorder is selected amongst Alzheimer and Parkinson diseases.

According to another embodiment, the assayed biological sample is from a subject known to bear a mutation in the CSB or CSA gene associated with a risk of Cockayne syndrome (CS), in particular is known to be homozygous for a mutation in the CSB or CSA gene associated with a risk of Cockayne syndrome (CS). Accordingly, the present invention may reveal the extent of mitochondrial impairment on the basis of the assayed sample.

The invention also relates to a protease inhibitor which interacts with protease(s) degrading POLG (i.e., the POLG entity as defined herein) for use in restoring POLG levels (i.e., the POLG entity as defined herein) in a patient in need thereof to treat or delay physiological or physiopathological ageing, in particular premature ageing, or accelerated ageing or a progeroid syndrome, such as Cockayne syndrome (CS), or neurodegenerative disorders or symptoms thereof, as defined above.

According to a particular embodiment, the invention also relates to a protease inhibitor which interacts with protease(s) degrading POLG1 for use in a patient in need thereof to treat or delay physiological or physiopathological ageing, in particular premature ageing, or accelerated ageing or a progeroid syndrome, such as Cockayne syndrome (CS), or neurodegenerative disorders or symptoms thereof, as defined above.

By "protease inhibitor which interacts with protease(s) degrading POLG1" it is meant a protease inhibitor having as target protease(s) degrading POLG1 (global proteasome inhibitors which target cysteine and serine proteases, or more specific serine protease inhibitors). Such a protease inhibitor may be specific of a particular protease degrading POLG1 or having a broad range of specificity, i.e., specificity for several proteases degrading POLG1. Such a protease inhibitor may also target cysteine and serine protease(s).

According to a particular embodiment, the protease inhibitor which interacts with protease(s) degrading POLG1 of the invention is a protease inhibitor targeting the HTRA3 protein as defined herein.

The experiments carried out by the inventors have indeed demonstrated that the HTRA3 protein has a key role when it comes to the levels of the POLG1 protein in cells, including in cells representative of the conditions disclosed herein.

Since the inventors also found that the level(s) of HTRA2 protein increase(s) in CS patients, and according to a particular embodiment, the invention also relates to a protease inhibitor targeting HTRA2 and/or HTRA3 for use in restoring POLG1 levels in a patient in need thereof to treat or delay physiological or physiopathological ageing, in particular premature ageing, or accelerated ageing or a progeroid syndrome, such as Cockayne syndrome (CS), or neurodegenerative disorders or symptoms thereof, as defined above.

The sequence of human HTRA2 protein (HTRA2 protein NCBI Reference Sequence: NP_037379.1 http://www.ncbi.nlm.nih.gov/protein/NP_037379.1), is provided herein under SEQ ID NO:7. The DNA sequence of human HTRA2 is provided under SEQ ID NO:8. As shown on page http://www.ensembl.org/Homo_sapiens/Transcript/Summary?db=core;g=ENSG00000115317; r=2:74757117-74760459;t=ENST00000352222, there are several protein transcripts (splicing variants) corresponding to human HTRA2. Accordingly, by HTRA2 protein as referred to herein, it is meant the native form of the protein having a sequence as disclosed in databases and/or literature and/or herein, but also isoforms or variants thereof having a polypeptidic sequence showing 60% or 70% or 80% or 90% or 95% and up to 99% identity with the polypeptidic sequence of the native HTRA2 protein.

According to another particular embodiment, the protease inhibitor which interacts with protease(s) degrading POLG1 of the invention is a protease inhibitor targeting the HTRA2 protein as defined herein.

According to a further particular embodiment, the protease inhibitor which interacts with protease(s) degrading POLG1 of the invention is a protease inhibitor targeting both the HTRA3 and the HTRA2 proteins as defined herein.

HTRA proteins including HTRA2 and HTRA3 are Trypsin-like serine proteases, by contrast to other proteases classified as Elastase-like or Chymotrypsin-like proteases.

Therefore, according to a particular embodiment, the protease inhibitor(s) suitable for use within the present invention are inhibitors of Trypsin-like serine proteases, which encompass the family of Kunitz-type trypsin inhibitors. According to a particular embodiment, the protease inhibitor which interacts with protease(s) degrading POLG1 of the invention is a protease inhibitor pertaining to the family of Kunitz-type trypsin inhibitors.

Natural trypsin inhibitors, also known as serine protease inhibitors (serpins), control the activation and catabolism of proteins by the inhibition of serine proteases in vivo. There are four natural sources of trypsin inhibitors: bovine pancreas, ovomucoid, soybean, and lima bean. All these sources are suitable sources for the natural trypsin inhibitors encompassed herein.

Molecules part of the family of Kunitz-type trypsin inhibitors include: BPTI (Basic Pancreatic Trypsin Inhibitor), Ovomucoid (also named Trypsin Inhibitor from chicken egg white (Type 11-0 or Type 111-0)), Kunitz Soybean Protease Inhibitor, BBI (Bowman-Birk (BBI) Soybean Protease Inhibitor), LBTI, STI, Tial, Trypsin inhibitor Type I-S/Type II-S, which are, according to particular embodiments, suitable for use as protease inhibitor(s) within the present invention, taken alone or in all combinations thereof.

In specific embodiments of the invention, the protease inhibitor to be administered to a patient in need thereof is a serine protease inhibitor, for example Soybean trypsin inhibitor (KSTI).

By "restoring POLG1 levels in a patient in need thereof" it is meant obtaining POLG1 levels values equal to or close to the normal threshold value(s) determined for healthy subject(s) for POLG1, as defined above.

According to a particular embodiment, the physiopathological ageing, in particular premature ageing, or accelerated ageing or a progeroid syndrome, such as Cockayne syndrome (CS), or neurodegenerative disorders or symptoms thereof recited above are associated with mtDNA replication dysfunction, and mtDNA replication dysfunction is in particular determined according to the method for investigating mtDNA replication dysfunction of the invention as defined herein.

In a particular embodiment, the physiopathological ageing, in particular premature ageing, or accelerated ageing or a progeroid syndrome, such as Cockayne syndrome (CS), or neurodegenerative disorders or symptoms thereof are associated with an abnormal expression of a functional protease, in particular an abnormal expression of functional POLG, more particularly functional POLG1, an abnormal expression being defined by reference to a normal expression value determined for healthy subject(s), as introduced above, said activity value(s) corresponding to level(s) of expressed functional protease(s), for example determined by immunofluorescence or Western Blotting or ELISA testing.

By "functional protease", it is meant a protease that has the capability to perform its function with the same performances than in a healthy cell. The capability to function with the same performances than in a healthy cell may be tested in living cells with mutants or knock down/silenced or knock out gene(s) coding for the protease of interest, and assessing the levels of POLG1 or any other protein of interest by Western Blot (WB) or Immunofluorescence (IF). Functional POLG1 may also be detected by sequencing the corresponding gene or checking that there is no large mtDNA depletion (as it is the case for pathological POLG1 mutations). For such a testing in protein extract(s), the protease of interest should be biochemically isolated and tested in vitro with a labeled substrate, the activity of which may be monitored to check its disappearance after contact with the protease of interest. Isolation of the protease of interest may encompass the use of sample containing several proteins, or the isolated protein of interest alone.

In a particular embodiment, an abnormal expression of a functional protease is an expression that is increased by reference to a predetermined normal expression value (e.g. at least a 2-fold increase for HTRA3 RNA; and/or at least a 10-fold of immunofluorescence signal for HTRA3 protein). Similarly to the determination of levels of proteins in healthy subjects referred to above, one skilled in the art can use common methods to determine said predetermined normal expression value by retrieving data from experiments carried on sample(s) containing healthy cells, or pools of such samples.

In a specific embodiment of the invention, a protease inhibitor to be administered to a patient in need thereof is a proteasome inhibitor, for example MG132 or is a serine protease inhibitor, for example Soybean trypsin inhibitor (KSTI).

According to a particular embodiment of the invention, use is made of a proteasome inhibitor as a protease inhibitor, which pertains to the family of benzyloxycarbonyl analogues or carbobenzoxy analogues.

MG132 is a molecule also known under its IUPAC name: benzyl N-[(2S)-4-methyl-1-[[(2S)-4-methyl-1-[[(2S)-4-methyl-1-oxopentan-2-yl]amino]-1-oxopentan-2-yl]amino]-1-oxopentan-2-yl]carbamate. Other names for MG132 are N-(benzyloxycarbonyl)leucinylleucinylleucinal or Z-Leu-Leu-Leu-al or carbobenzoxy-Leu-Leu-leucinal.

According to another particular embodiment, use is made of a protease inhibitor, which is not a proteasome inhibitor as defined herein, or more particularly of a protease inhibitor to the exclusion of the MG132 described above.

According to a more specific embodiment, use is made of a protease inhibitor as defined herein, to the exclusion of the proteasome inhibitors or of the MG132 when the physiopathological ageing condition to be treated is a neurodegenerative disorder.

It has been indeed observed that proteasome inhibitors such as MG132 have toxic effects on their cellular targets that may be regarded as counterproductive in the context of use according to the invention.

KSTI, as discussed above, is one of the two major trypsin inhibitors in soybeans, as disclosed in Reza Roosta et al, 2011 Advances in Environmental Biology, 5(1): 145-153, which describes its isolation and characterization. KSTI is in particular known to target, at least, both HTRA2 and HTRA3 proteases amongst the family of serine proteases.

In a particular embodiment of the invention, the protease inhibitor used for increasing POLG levels in a patient in need thereof is administered to a patient diagnosed with Cockayne syndrome (CS).

Since management of oxidative stress is altered in CS defective cells and involved in the new mechanism described herein explaining defects in CS cells, the invention also relates to a nitroso-redox stress scavenger compound or a composition comprising or consisting essentially of such a compound for use in a patient in need thereof:
  a. to treat or delay Cockayne syndrome (CS) or symptoms thereof, and/or
  b. to restore the level(s) of protein(s) selected in the group of: HTRA2, HTRA3 and POLG1, or combinations thereof, in particular to treat or delay Cockayne syndrome (CS) or symptoms thereof.

By "nitroso-redox stress scavenger compound(s)", it is meant a compound having for functional achievement(s) to act on the nitroso-redox balance by scavenging one or, preferably both, amongst reactive oxygen species (ROS) and reactive nitrogen species (RNS). Such compounds may be antioxidant(s), in particular antioxidant(s) with a porphyrine core or moiety.

According to a particular embodiment, said "nitroso-redox stress scavenger compound(s)" pertain to the category of SOD Mimetic and Peroxynitrite Scavenger(s).

According to another particular embodiment, said "nitroso-redox stress scavenger compound(s)" is/are a cell permeable superoxide dismutase mimetic(s) (against ROS) and peroxynitrite scavenger(s) (against RNS).

According to another particular embodiment, said "nitroso-redox stress scavenger compound(s)" pertain to the family of porphyrin chloride analogs.

According to another particular embodiment, said "nitroso-redox stress scavenger compound(s)" is/are metalloporphyrin(s), in particular manganese porphyrin(s).

According to a particular embodiment, the nitroso-redox stress scavenger compound is selected amongst:

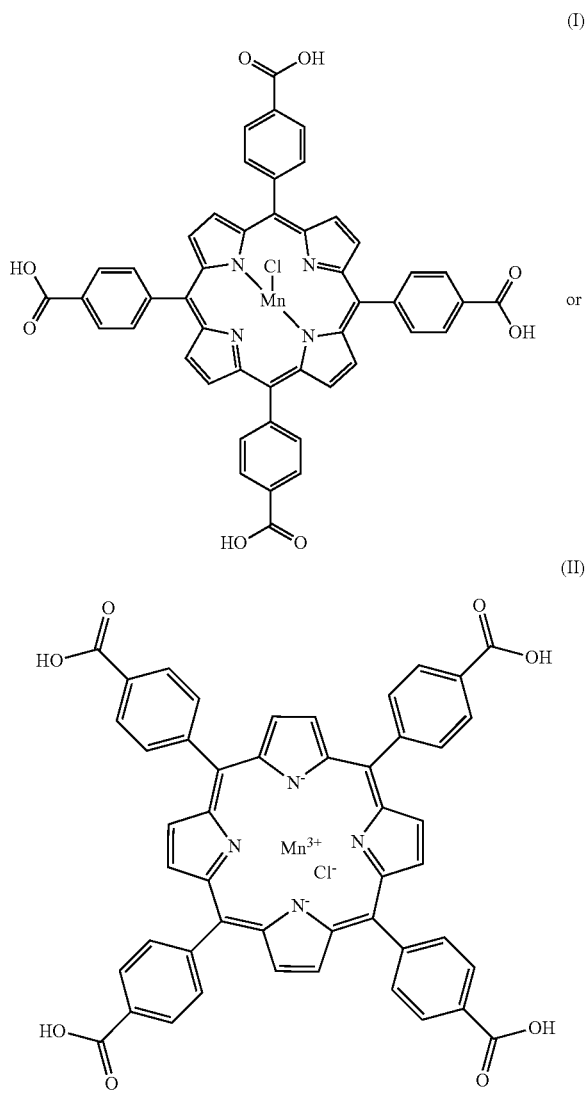

and a mixture of (I) and (II), or analogs thereof.

By "restoring the level(s) of protein(s) selected in the group of: HTRA2, HTRA3 and POLG, or combinations thereof" it is meant obtaining HTRA2 and/or HTRA3 and/or POLG (i.e., the POLG entity as defined herein) levels values, taken alone or in all combinations of these species, equal to or close to the normal threshold value(s) determined for healthy subject(s) for HTRA2 and/or HTRA3 and/or POLG (i.e., the POLG entity as defined herein), respectively or in combination, as defined above and also illustrated in the Examples.

A nitroso-redox stress scavenger compound according to a particular embodiment of the present invention, as illustrated by formulas (I) and (II) above, is known in the literature under the common name MnTBAP.

According to this embodiment of the invention, and as disclosed herein, MnTBAP has the molecular formula $C_{48}H_{28}ClMnN_4O_8$ and encompasses compounds corresponding to the IUPAC name Chloro[4,4',4'',4'''-(5,10,15,20-porphyrintetrayl-$\kappa^2$, $N^{23}$)tetrabenzoato(2-)]manganese or systematic names Chloro [4,4',4'',4'''-(5,10,15,20-porphyrintetrayl-$\kappa^2 N^{21}, N^{23}$) tetrabenzoato(2-)] Manganese or Manganese (3+) chloride 5,10,15,20-tetrakis(4-carboxyphenyl)porphine-21,23-diide (1:1:1) or any one of the names Mn(III) meso-Tetra (4-carboxyphenyl) porphine chloride or Manganese(III)-tetrakis(4-benzoic acid)porphyrin or Mn(III) tetrakis(4-benzoic acid)porphyrin, or manganese [III] tetrakis (5, 10, 15, 20 benzoic acid) porphyrin, or Manganese (III) tetrakis (4-benzoic acid) porphyrin chloride or their equivalents depending on the nomenclature referred to for the name used.

MnTBAP can be found under its salt form (II) or as a complex (I) or mixtures thereof. Commercial preparations of MnTBAP exist that may contain MnTBAP with amounts of Mn-free ligand. Such preparations are also suitable for carrying out the present invention.

Analogs of (I) or (II) may include a manganese porphyrin related to MnTBAP, for example, Mn [III] tetra(4-pyridyl) porphyrin (MnTyP). Analogs may further include copper containing porphyrins, such as copper(II) (3,5-diisopropyl salicylate)2 (CuDIPS) and its derivatives.

According to another particular embodiment, suitable "nitroso-redox stress scavenger compound(s)" are MNTEPyP and its analogs, or MNTMPyP and its analogs.

By "nitroso-redox stress", it is meant the alteration of the nitroso-redox balance. The nitroso-redox balance consists in the interaction between nitric oxide (NO) and reactive oxygen species (ROS) production. The nitroso-redox balance has relevant signaling function in the organism and its impairment may result in dysfunctions.

According to a particular embodiment, a nitroso-redox stress scavenger compound according to the present disclosure is used for treating or delaying Cockayne syndrome (CS) or symptoms thereof, and/or restoring the level(s) of protein(s) selected in the group of: HTRA2, HTRA3 and POLG, or combinations thereof, in particular to treat or delay Cockayne syndrome (CS) or symptoms thereof, wherein the Cockayne syndrome (CS) or symptoms thereof are associated with mtDNA replication dysfunction, in particular mtDNA replication dysfunction that is determined according to the method for investigating mtDNA replication dysfunction of the invention as defined herein.

According to a particular embodiment, a nitroso-redox stress scavenger compound according to the present disclosure is used for restoring the level(s) of protein(s) selected in the group of: HTRA2, HTRA3 and POLG, or combinations thereof, in order to treat or delay Cockayne syndrome (CS) or symptoms thereof.

In a particular embodiment, the Cockayne syndrome (CS), or symptoms thereof, are associated with an abnormal expression of a functional protease, in particular an abnormal expression of functional POLG, more particularly functional POLG1, an abnormal expression being defined by reference to a normal expression value determined for healthy subject(s), as introduced above, said activity value(s) corresponding to level(s) of expressed functional protease(s), for example determined by immunofluorescence or Western Blotting or ELISA testing. Definitions of "functional protease" and "abnormal expression of a functional protease" are the same than provided above.

According to a particular embodiment of the invention, the use of a protease inhibitor interacting with protease(s) degrading POLG1, for increasing POLG1 levels in a patient in need thereof and/or treating or delaying physiological or physiopathological ageing, or neurodegenerative disorders or symptoms thereof, as defined above, is performed on individuals previously subjected to the method for investigating mtDNA replication dysfunction according to any one of the embodiments described herein.

According to a particular embodiment, the use of a nitroso-redox stress scavenger compound according to the present disclosure for treating or delaying Cockayne syndrome (CS) or symptoms thereof, and/or restoring the level(s) of protein(s) selected in the group of: HTRA2, HTRA3 and POLG, or combinations thereof, is performed on individuals previously subjected to the method for investigating mtDNA replication dysfunction according to any one of the embodiments described herein.

It is another object of the present invention to use a protease inhibitor which interacts with protease(s) degrading POLG1 as defined herein in combination with a nitroso-redox stress scavenger compound as defined herein, or to use a nitroso-redox stress scavenger compound as defined herein in combination with a protease inhibitor which interacts with protease(s) degrading POLG1 as defined herein, in a patient in need thereof:
  a. to treat or delay physiological ageing or physiopathological ageing, in particular premature ageing, or accelerated ageing or a progeroid syndrome, such as Cockayne syndrome (CS), or neurodegenerative disorders or symptoms thereof, and/or
  b. to restore the level(s) of protein(s) selected in the group of: HTRA2, HTRA3 and POLG, or combinations thereof, in particular to treat or delay Cockayne syndrome (CS) or symptoms thereof.

According to particular embodiments, the administration in combination of said protease inhibitor and nitroso-redox stress scavenger compound can be made concomitantly, separately or in a sequential regime, with the protease inhibitor being administered before or after the nitroso-redox stress scavenger to the patient in need thereof.

When active compounds are administered, to either cells or patients, the appropriate dosage regimen may be determined by the person skilled in the art. In particular, it is not unusual to severely decrease the dose administered to patients with respect to the dose administered to cells, without loss of effect.

The invention also relates to a kit suitable for carrying out a method of the invention, comprising:
  at least one pair of specific oligonucleotide primers specific for hybridization with HTRA3 and/or POLG cDNA, and/or at least one pair of specific oligonucleotide primers specific for hybridization with HTRA3 RNA and/or POLG RNA, and, optionally, one or several of the following reagents,
  nucleotides (e.g. dATP, dCTP, dGTP, dUTP),
  a reverse transcriptase enzyme,
  a DNA polymerase, in particular a thermostable DNA polymerase, such as a Taq DNA Polymerase,
  at least one label or marker for detection of nucleic acids, in particular a dye detectable in a real-time PCR equipment,
  optionally, a buffer solution,
  optionally, reagents necessary for the hybridization of the primers to their targets, optionally, a reference label or marker and,
a notice providing instructions for use and expected values for interpretation of results.

In another aspect, a kit of the invention a kit suitable for carrying out a method of the invention, comprises:

At least one antibody specific for a protein selected amongst: POLG1, POLG2, HTRA3, HTRA2 or a combination of several antibodies specific for POLG1, POLG2, HTRA3, HTRA2 and, optionally, at least one pair of specific oligonucleotide primers specific for hybridization with HTRA3 and/or POLG1 cDNA, and/or at least one pair of specific oligonucleotide primers specific for hybridization with HTRA3 RNA and/or POLG1 RNA and, optionally one or several of the following reagents, a secondary antibody or reagent to reveal a complex between specific antibody(ies) recited above and its (their) target, optionally, a buffer solution, optionally, an assay plate, and a notice providing instructions for use and expected values for interpretation of results.

The invention also relates to the use of a kit as defined above for investigating mtDNA replication dysfunction, and/or monitoring or diagnosing the health status of a subject susceptible of suffering from physiological or accelerated ageing or a progeroid syndrome, such as Cockayne syndrome (CS), or neurodegenerative disorders or symptoms thereof.

Examples of reagents suitable for being used within kits according to the present invention are also described in the Material and Methods section herein.

Another aspect of the invention is an in vitro process for screening protease inhibitor(s) for identifying protease inhibitor(s) capable of restoring POLG1 level in a cell, and/or for screening nitroso-redox stress scavenger compound(s) for identifying nitroso-redox stress scavenger compound(s) capable of restoring POLG1 level in a cell, comprising the steps of:

i. contacting a cell or a cell culture, in particular a fibroblast or a culture thereof, having a decreased level of POLG1 by at least 10%, in particular at least 20% with respect to a normal threshold value determined for cells characteristic of healthy subject(s) with a marker specifically recognizing POLG1, ii. contacting said cell(s) with protease inhibitor(s) and/or nitroso-redox stress scavenger compound(s) to assay, wherein steps i. and ii. can be inverted, iii. measuring and/or visualizing the change(s) in properties, in particular the level of POLG1 of the cell(s) contacted in steps i. and ii., and, iv. optionally, recording or quantifying the change(s) in properties, in particular the level of POLG1, of the cell(s) contacted in steps i) and ii).

A definition of "nitroso-redox stress scavenger compound(s)" is provided above. The functional achievement(s) of such compound(s) is also disclosed herein. Nitroso-redox stress scavenger compound(s) may be ROS and/or peroxynitrite (or nitro-oxidative molecules) scavengers, as disclosed herein. Administration of such nitroso-redox stress scavenger compound(s) to a cell may ultimately lead to reduce ROS levels in said cell.

The change(s) in properties referred to in step iii) above are also mentioned in the present disclosure.

The invention will be further described herein, referring to the following figures, material and methods section, and experimental section.

LEGENDS OF FIGURES

FIGS. 1A to 1D. Decreased POLG1 levels in cells from CS patients. (A) RT-qPCR of POLG1 in fibroblasts from patients with mutated CSB and associated with type I or Type II CS or with $UV^SS$ syndromes, compared to a control healthy individual 194; values of 194 were confirmed in other healthy individuals, not shown. Each number corresponds to a patient, and the disease as well as the mutated gene is indicated below. Value of control=1; mean±standard deviation. No relevant differences in POLG transcripts are detected among the different samples. (B) 3D-reconstruction of human fibroblasts immunolabelled for POLG1 (light grey spots), and stained with Hoechst (nuclei, dark grey), and measured in panel B. (C) Fluorescence intensity quantification of POLG1 by immunofluorescence. n=30 cells from 3 independent experiments; mean±SEM. All CS samples are significantly different compared to healthy samples ($p<0.001$) (D) Western blot of POLG1 and of the housekeeping gene GAPDH in cells from control, $UV^SS$, and CS patients.

Figure 2:
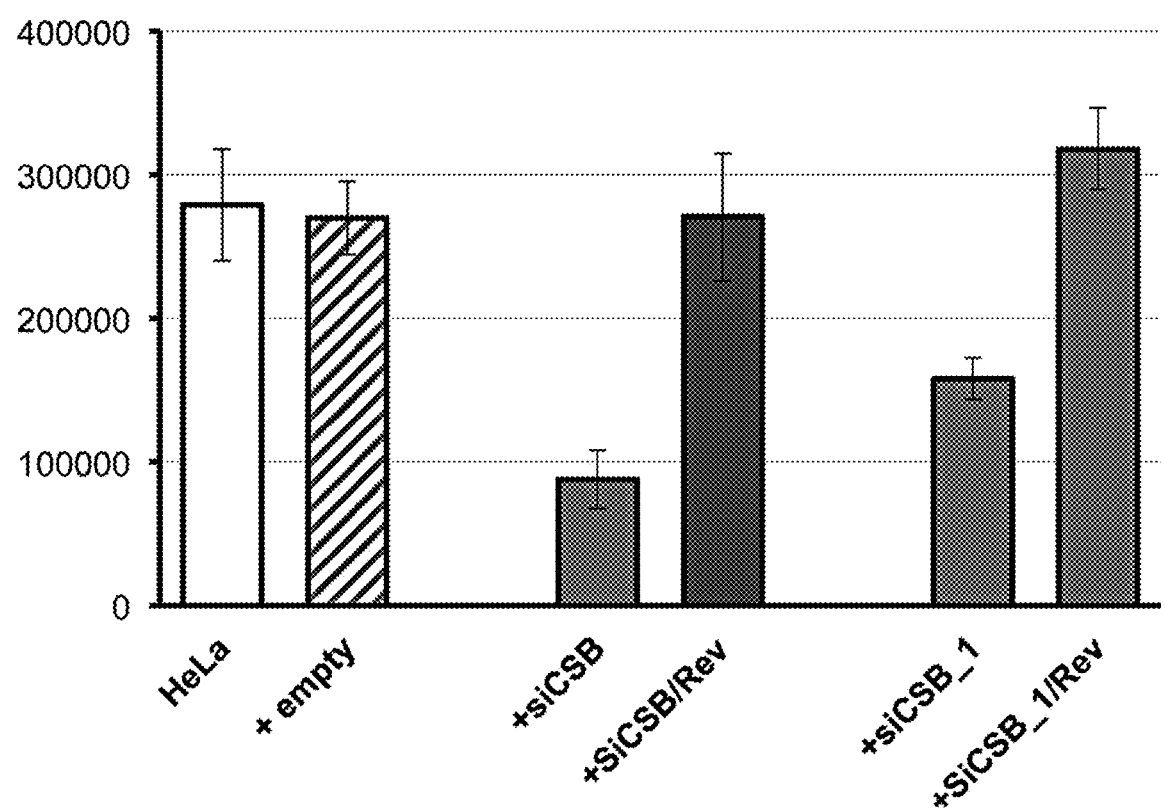

FIG. 2. Silencing of CSB gene results in stable decreased POLG1 levels in HeLa cells. Fluorescence intensity quantification of POLG1 by immunofluorescence. Two independent HeLa cell lines silenced for CSB were used ("+siCSB" and "+siCSB_1"); the cell line transfected with empty plasmid (no siRNA sequence) is indicated with a hatched column; reversion of the silencing by loss of the siRNA plasmid (clones "+siCSB/Rev" and "+siCSB_1/Rev") was obtained by growing cells for 21 days in the absence of the selection antibiotic. n=30 cells from 3 independent experiments; mean±SEM. CSB levels were tested in all samples by RT-qPCR and by Western blot. siCSB and siCSB_1 resulted in silencing by 68% and 43%, respectively)

Figure 3A:
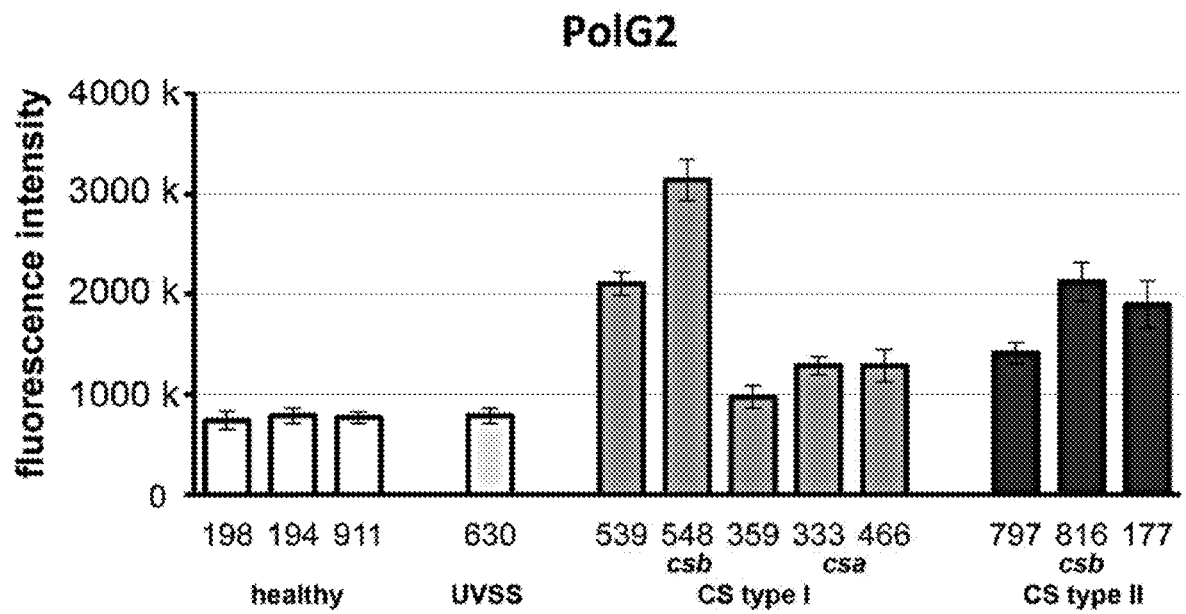
Figure 3B:
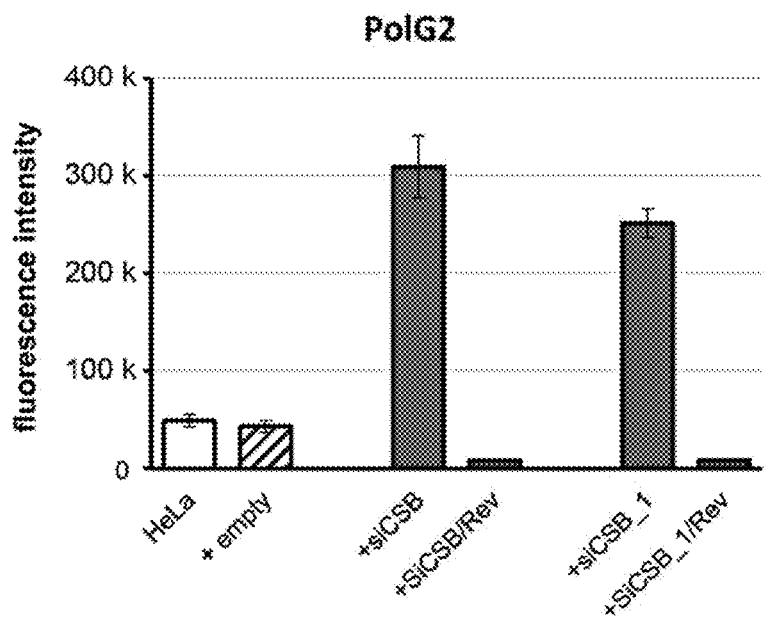

FIGS. 3A to 3B. Increased levels of POLG2 in fibroblasts from CS patients compared to controls. (A) Quantification of POLG2 immunofluorescence in fibroblasts from different individuals. CS samples but 359 are significantly different compared to healthy samples ($p<0.001$). (B) Quantification of POLG2 immunofluorescence in HeLa cells, either silenced for CSB or after reversion of silencing, as indicated in FIG. 2. Control untreated cells, and in the presence of empty plasmid are also measured. n=30 cells from 3 independent experiments; mean±SEM. CS samples but 359 are significantly different compared to healthy samples ($p<0.001$).

Figure 4A:
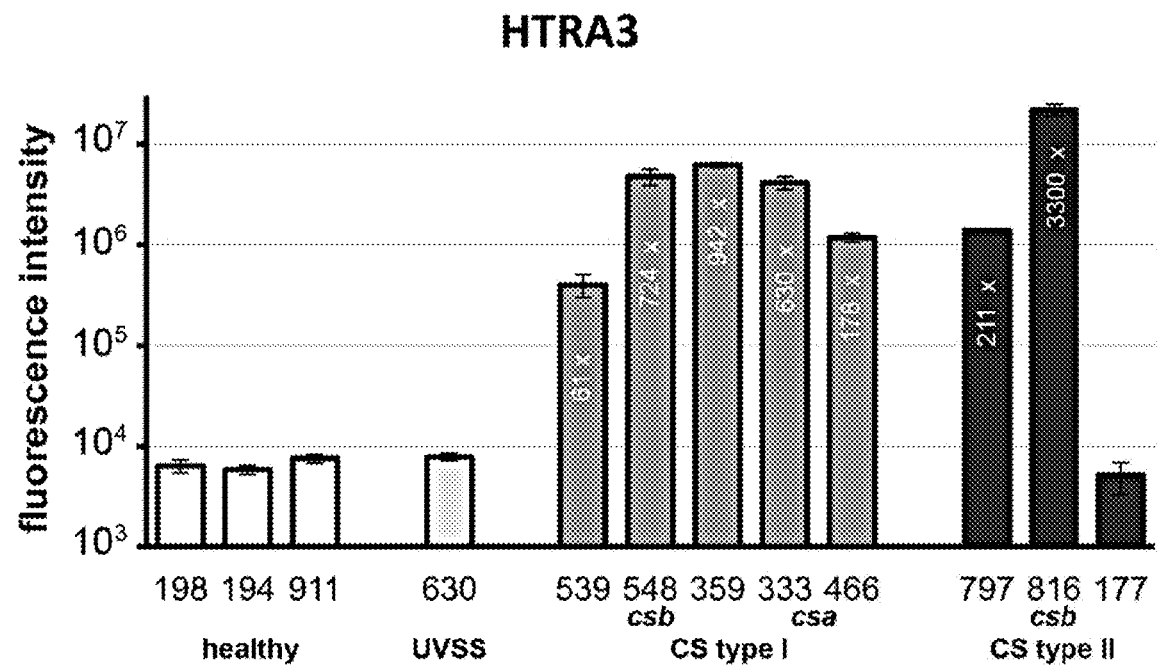
Figure 4B:
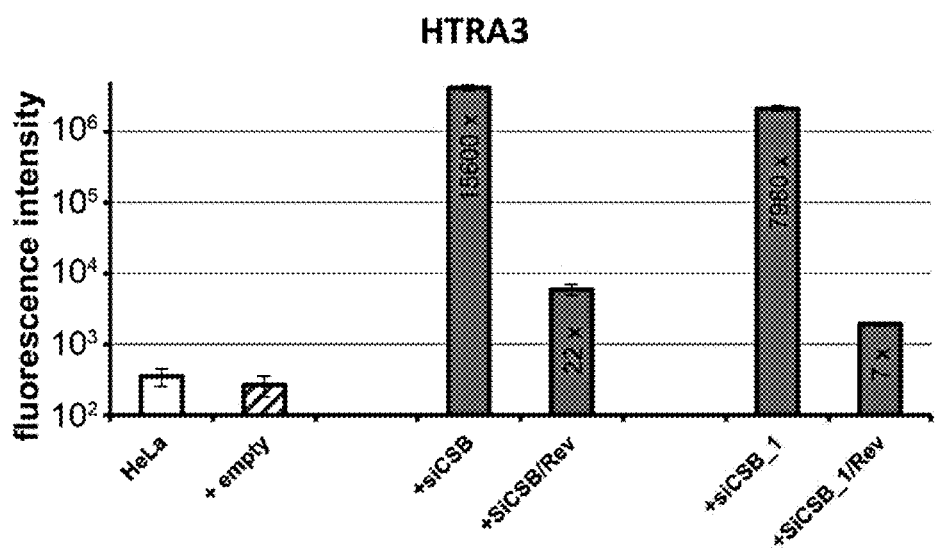

FIGS. 4A to 4B. CSB impairment results in increased HTRA3 levels. (A) Quantification of HTRA3 immunofluorescence in fibroblasts from different individuals. Results expressed in logarithmic scale; fold increase compared to the mean of three controls is indicated within each column. CS samples but 177 are significantly different compared to healthy samples ($p<0.001$). (B) Quantification of HTRA3 immunofluorescence in HeLa cells, either silenced for CSB or after reversion of gene silencing, as indicated in FIG. 2. Control untreated cells and in the presence of empty plasmid are also measured. n=30 cells from 3 independent experiments; mean±SEM.

Figure 5B:
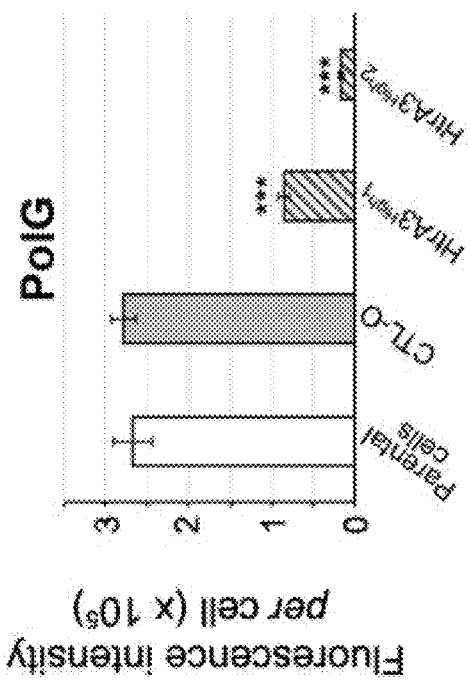
Figure 5A:
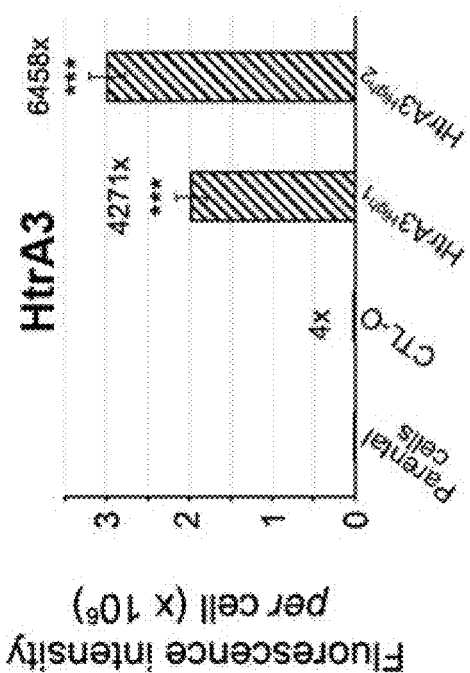

FIGS. 5A to 5B. PolG depletion is dependent on HtrA3 overexpression. Quantification of (A) HtrA3 and (B) PolG1 immunofluorescence in HeLa parental cells, or cells transfected with an empty vector (CTL-0) or a vector coding for HtrA3 ($HtrA3^{High}_1$ for pBD3188, and $HtrA3^{High}_2$ for pBD3189). In panel A, HtrA3 fold increase compared to HeLa is shown on top of each column. Immunofluorescence quantification, per condition n=30 cells from three independent experiments.

Figure 6:
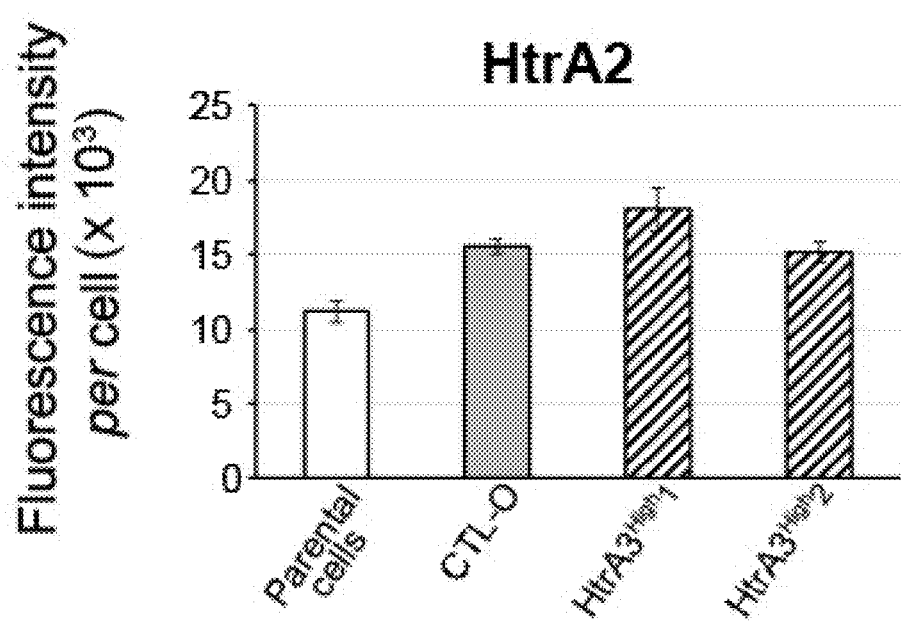

FIG. 6. HtrA2 levels do not depend on HtrA3 expression. Quantification of HtrA2 immunofluorescence in HeLa parental cells, or cells transfected with an empty vector (CTL-0) or a vector coding for HtrA3 (HtrA3$^{High}_1$ for pBD3188, and HtrA3$^{High}_2$ for pBD3189). Immunofluorescence quantification, per condition n=30 cells from three independent experiments.

Figure 7:
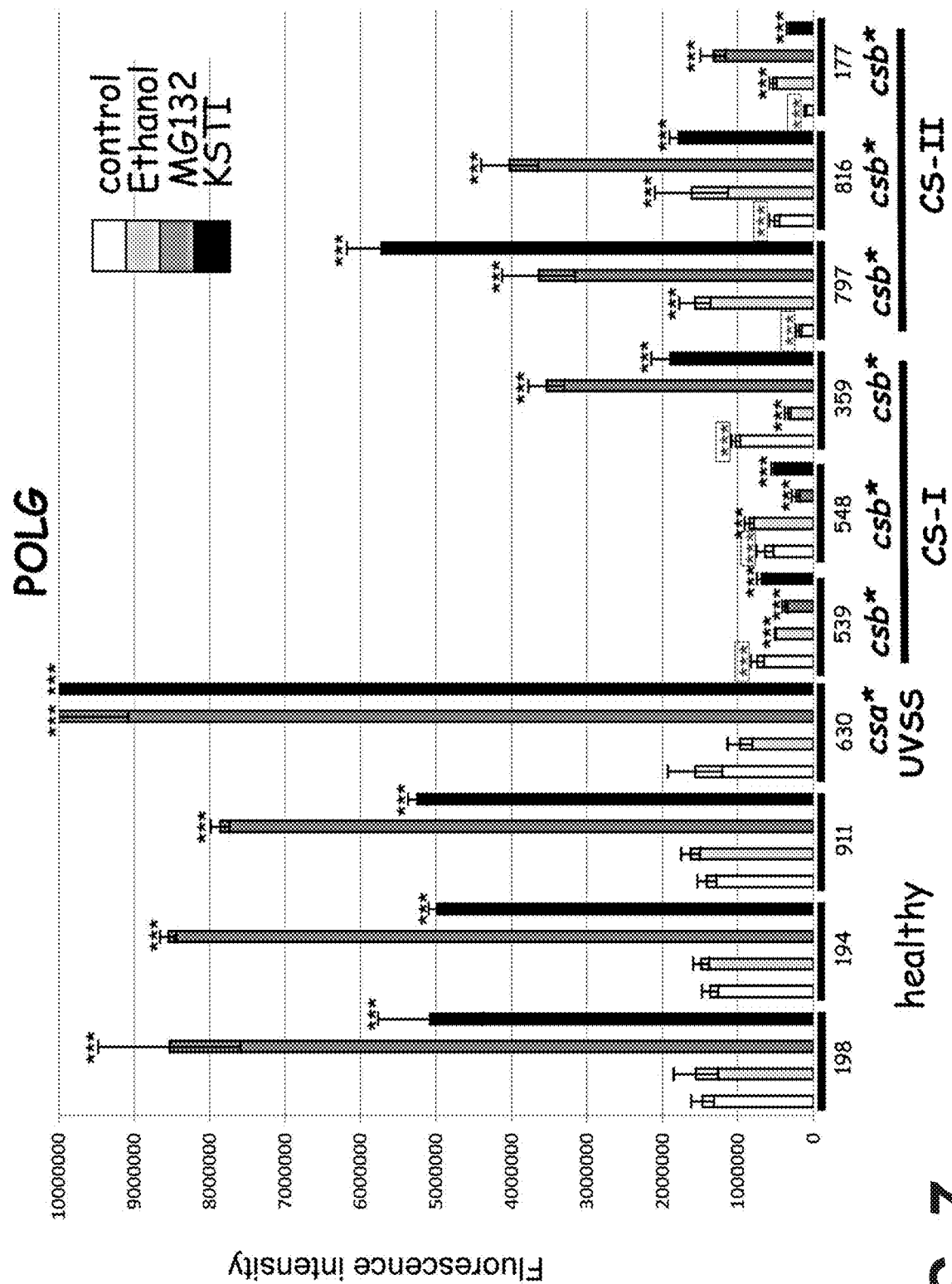

FIG. 7. Increasing POLG1 levels in CS cells after treatment with protease inhibitors. Columns indicate POLG1 immunofluorescence in skin fibroblasts from healthy patients (198, 194, and 911), from UV$^S$S, and from CS type I (539, 548, and 359) and type 11 (797, 816, and 177). The gene mutated is indicated with an asterisk. For each sample cells were untreated (white) or treated with ethanol (at the same concentration as for dissolving the protease inhibitor), or with MG132 or with KSTI. n=30 cells from 3 independent experiments, mean±SEM. P<0.001 (***) compared to untreated cells (black stars) or to healthy individuals (grey stars, squared) corresponding to healthy samples 539, 548, 359, 797, 816, 177, only for untreated cells).

FIGS. 8A to 8D. Increased nitroso-redox stress in CS cells. (a and c) 3D-reconstructions of DCF-treated cells (light gray staining) for detecting ROS levels, and counterstained with Hoechst (nuclei, dark grey), upper panel. Fluorescence intensity quantification of DCF per cell, lower panel. (b and d) 3D-reconstructions of DHR123-treated cells (light gray staining) for detecting peroxynitrite levels, and counterstained with Hoechst (nuclei, dark grey), upper panel. Fluorescence intensity quantification of DHR123 per cell, lower panel. (a) and (b), human primary fibroblasts; (c) and (d), immortalized fibroblasts and HeLa cells silenced for CSB and their revertants (see Table 1). Scale bar=10 μm. Immunofluorescence, n=30 cells from three independent experiments; t-test, ***p≤0.001 versus 198VI (primary fibroblasts), or MRC-5 (immortalized fibroblasts) or HeLa (silenced cell lines).

FIGS. 9A to 9H. Scavenger of nitroso-redox stress restores original mitochondrial parameters in patient cells. (a) Fluorescence intensity quantification of DCF per cell. (b) Fluorescence intensity quantification of DHR123 per cell. Fluorescence intensity quantification of (c) HTRA2, and (d) HTRA3, and (e) POLG1 per cell with below POLG1 immunoblots and band intensity quantitation normalized to GAPDH and to untreated control 198. (f) qPCR of mtDNA content. (g) Fraction of glycolysis and OXPHOS (±oligomycin) in ATP synthesis. (h) Total ATP level per cell. Immunofluorescence, n=30 cells from three independent experiments; n=3 independent experiments for immunoblot, ATP tests, and qPCR. t-test, ***p≤0.001 versus 198VI. Untreated controls (healthy individuals) 198, 194, and 911: white columns; UVSS, CS-I, and CS-II patients: light, medium, and dark grey columns, respectively. For each sample, untreated cells are shown on the left, and cells treated with MnTBAP on the right (pached columns).

TABLE 1

Characteristics of (a) primary skin fibroblasts from healthy individuals (wildtype), UV$^S$S, and CS patients, and (b) cellular models including CSB levels, used in the present study.

(a)

| Patient's number | Diagnosis | Mutation | CSA/CSB |
|---|---|---|---|
| 198VI | Wildtype | — | |
| 194VI | Wildtype | — | |
| 911VI | Wildtype | — | |
| UVSS1VI | UV$^S$S | csa | |
| CS539VI | CS type I | csb | Absence of CSB |
| CS548VI | CS type I | csb | Absence of CSB |
| CS359VI | CS type I | csb | Absence of CSB |
| CS333VI | CS type I | csa | Absence of CSA |
| CS466VI | CS type I | csa | Absence of CSA |
| CS797VI | CS type II - COFS | csb | 50% CSB loss |
| CS816VI | CS type II - COFS | csb | Truncated forms |
| CS177VI | CS type II - COFS | csb | Absence of CSB |

(b)

| Model | Characteristics | CSB RNA | CSB protein |
|---|---|---|---|
| MRC-5 | SV-40 transformed human fibroblasts | Wildtype | Wildtype |
| CSIAN | SV-40 transformed CSB-deficient human fibroblasts | Absence of CSB | Absence of CSB |
| HeLa | Human cell line | Wildtype | Wildtype |
| mock | mock | Wildtype | Wildtype |
| siCSBa | siCSB cell line | Extinction 89% | Absence of CSB |
| siCSBa-RV | Reverted siCSB | Overexpression 282X | High CSB level |
| siCSBb | siCSB cell line | Extinction 82% | Absence of CSB |
| siCSBb-RV | Reverted siCSB | Overexpression 82X | High CSB level |

1. MATERIALS AND METHODS

Immunofluorescence Staining.

Cells plated on slides were fixed with 2% PFA and permeabilized with 0.5% Triton X-100. The slides were incubated in blocking buffer (BSA 5% in PBS) for 1 h then with the primary antibody (POL$_\gamma$ and HTRA3 purchased from SantaCruz Biotechnology, or as available from any other provider) for 1 h at room temperature. A second, fluorescent antibody (goat anti-mouse and goat anti-rabbit Alexa® Fluor 488, Alexa® Fluor 555, conjugated secondary antibodies from Invitrogen or by any other provider), was incubated for 1-2 h at room temperature, and DNA was stained with 10 μg/ml Hoechst.

Fluorescence Quantification and Image Analysis.

Image analysis was carried out using Perkin-Elmer Ultraview RS Nipkow-spinning disk confocal microscope. Three-dimensional reconstruction of all the z-stacks was achieved using the 3D-volume rendering of IMARIS software (Bitplane). A regular fluorescence microscope can also be used, including for fluorescence quantification, although in this last case it will quantify one section of the cell only and not the entire volume; this quantification may be sufficient for comparative studies (normal versus patient cells). Confocal acquisition (even in the absence of spinning disk) in 3D allows quantification of the entire volume, and differences among samples are therefore more robust.

RT-qPCR.

Total RNA was isolated from HeLa cells using the RNAeasy Mini kit (Qiagen), treated with DNaseI (Qiagen), then reverse-transcribed using Superscript® III Reverse transcriptase (Invitrogen). Real-time quantitative PCR was performed using Power Sybr Green PCR Master Mix (Applied Biosystems) and the rate of dye incorporation was monitored using the StepOne™ Plus RealTime PCR system (Applied Biosystems). Three biological replicates were used for each condition. Data were analyzed by StepOne Plus RT PCR software v2.1 and Microsoft excel. TBP transcript levels were used for normalisation of each target (=ΔCT). Real-time PCR $C_T$ values were analyzed using the $2^{-\Delta\Delta C_t}$ method to calculate the fold expression (Schmittgen and Livak, 2008). Custom primers were designed using the Primer3Plus online software (http://www.bioinformatics.nl/cgi-bin/primer3plus.cgi). Customs primers used by the inventors (SEQ ID NO: 9 to 18) are listed in the table below.

| | Primer's sequence | Literature/Reference |
|---|---|---|
| POLG1 forward | 5'GAGAAGGCCCAGCAGATGTA | Setzer et al, 2008. |
| POLG1 reverse | 5' ATCCGACAGCCGATACCA | American J. Pathology 172: 681-90 |
| POLG2 forward | 5' GAGCTGTTGACGGAAAGGAG | Armstrong et al, 2010. |
| POLG2 reverse | 5' GTTCTTCCGCAACTCTACGC | Stem Cells 28: 661-673 |
| Long HTRA3 forward | 5' ATGCGGACGATCACACCAAG | Nie et al, 2006 Biology of reproduction 74: 366-374 |
| Long HTRA3 reverse | 5' CGCTGCCCTCCGTTGTCTG | |
| Short HTRA3 forward | 5'GAGGGCTGGTCACATGAAGA | |
| Short HTRA3 reverse | 5' GCTCCGCTAATTTCCAGT | |
| HTRA2_forward | 5' TTTGCCATCCCTTCTGATCG | Sequence NM_013247, 1590-1777 |
| HTRA2_reverse | 5' ACACCATGCTGAACATCGGG | |

Protein Extraction and Western Blot.

Cells were lysed by lysis solution (20 mM Tris, 18 mM NaCl, 0.5% Lauryl β Maltoside, 1 mM $MgCl_2$, 200 mM $Na_4P_2O_7$, 1 mM EGTA, 20 mM NaF, 2 mM $NaVO_4$, 1 mM Pefabloc (Sigma), 1 mM Aprotinin (Sigma), 1 mM Leupeptin (Sigma). Protein content was determined with the Bradford reagent (Sigma) and 30 μg of protein were loaded for SDS-PAGE. After blotting, Hybond ECL nitrocellulose filters were probed with anti-$POL_\gamma$ or anti-HTRA3 antibodies. Detection was performed using Odyssey Infrared Imaging system scanner and Odyssey application software v 3.0 (LI-COR Biosciences).

ELISA methods have been performed according to standard methods as known by the person skilled in the field and according to the recommendations of the fabricant(s) when standard kits were used.

2. EXPERIMENTAL SECTION

A. Diagnosis

Experiment 1 (FIG. 1

The inventors found that POLG1 protein levels, measured by immunofluorescence and Western blot, are reduced in fibroblasts from CS patients (either from type I or type II, the latter displaying the most severe phenotype) compared to fibroblasts from healthy individual and from $UV^SS$ patients (FIG. 1). mRNA levels are not remarkably different in these individuals.

Experiment 2 (FIG. 2

Silencing of CSB in HeLa cells using replicative pEBV-siRNA plasmids[19] resulted in decreased polG levels (tested by RT-qPCR and immunofluorescence) at levels compatible with those observed in CS patients (FIG. 2). Moreover, reversing the silencing by loss of the siRNA coding plasmid resulted in restoring original POLG1 levels. These experiments show that alteration of POLG1 levels are directly due to CSB inactivation.

Experiment 3 (FIG. 3

POLG2 is an accessory protein that increases the processivity of the catalytic subunit of POLG1[20]. The inventors observed that POLG2 levels essentially increased in cells from CS patients compared to healthy individuals and to $UV^SS$, although the effect was particularly strong for CSB mutations than for CSA mutations (FIG. 3A). In one CS case (patient 539) there was no significant increase of POLG2. It is hypothesized that increased levels of the accessory protein may result as compensation of the decreased levels of POLG1 to reinforce the DNA polymerase complex. Moreover, silencing of CSB in HeLa cells results in increased levels of POLG2 (FIG. 3B), and reversion of the silencing for the loss of plasmid results in dropping the levels of POLG2, showing that increased levels of POLG2 are dependent on impaired CSB.

Experiment 4 (FIG. 4

Reduced levels of POLG1 in CSB altered cells (in patients and by gene silencing) in the presence of regular levels of POLG1 transcripts indicate that either translation is impaired or protein degradation is enhanced. HTRA3 (high-temperature requirement factor A3) is a nuclear-encoded mitochondrial serine protease that degrades damaged proteins, and has a function during development, and possibly as tumor suppressor[21]. The inventors observed dramatically high levels of HTRA3 protein, assessed by immunofluorescence, in fibroblasts from CS patients, compared to controls and $UV^SS$ fibroblasts (FIG. 4A). Moreover, CBS-silenced HeLa cells result in highly increased levels of HTRA3, and reversion of the silencing greatly decreases HTRA3 levels (FIG. 4B). These data indicate that HTRA3 levels are dependent on CSB.

Experiment 5 (FIG. 5): Demonstration that PolG Levels Depend on Htra3 Overexpression In Experiment 4, it has been shown association between increase of HtrA3 and depletion of PolG1, but not directly shown that increase of HtrA3 induced depletion of PolG1. This experiment provides direct evidence that this is the case. It is shown that overexpression of HtrA3 protein in HeLa cells decreases PolG1 levels. Both overexpression of HtrA3 (on a logarithmic scale) and PolG1 depletion appear comparable to levels detected in CS patient cells (FIG. 5). These data also show that HtrA3 levels must be particularly high to deplete PolG1, since a 4-fold increase, as in transfection with empty vector (CTL-O), does reduce PolG1 levels.

Experiment 6 (FIG. 6): Demonstration that HtrA3 does not Affect HtrA2 Levels

HtrA3 is a serine protease, which could target and degrade HtrA2 or a protein involved in the regulation of HtrA2. The inventors assessed HtrA2 levels in HtrA3 overexpressing HeLa cells, and observed that HtrA2 protein immunofluorescence was not altered by a few thousand-fold increase in HtrA3 (FIG. 6). Thus HtrA2 is not directly or indirectly affected by HtrA3 levels. This finding is relevant to the use of specific serine protease inhibitors to reduce the levels of HtrA3 alone and/or HtrA2.

B. Therapy Strategy

For the reasons developed above, the precocious ageing phenotype can be ascribed to the mismanagement of oxidative stress in CS and cells affected by ageing, let it be physiological or physiopathological, as described herein.

Through the preceding experiments, the inventors showed that cells from CS patients, compared to cells from healthy individuals and from $UV^SS$, are characterized by lower levels (e.g. at least a 20% decrease, in particular when tested by immunofluorescence) of the nuclear encoded mitochondrial DNA polymerase gamma (POLG1), by higher levels of the accessory factor POLG2 (e.g. at least a 25% increase, in particular when tested by immunofluorescence), and by dramatically higher levels of the serine protease HTRA3 (e.g. at least a 10-folds increase, when tested by immunofluorescence). They also showed that alterations in the levels of these proteins are linked to impairment of CSB.

Thus, CSB impairment directly or indirectly increases Htra3 levels, and this serine protease in turn degrades its targets, which include POLG1. In spite of increased levels of the accessory protein POLG2, likely to compensate for the impaired mitochondrial DNA replication complex, replication of mitochondrial DNA is affected when CSB is not operating, leading to a decline in the mitochondrial function and thereby to enhanced production of oxidative stress. Increased oxidative stress and affected mitochondrial function, which cumulate with time, contribute to leading to precocious ageing phenotype.

HTRA3 is a serine protease. The inventors hypothesized that inhibition of proteases should decrease HTRA3 levels and help restoring correct POLG1 levels. They thus tested two protease inhibitors, MG132 that is a specific proteasome inhibitor, and Soybean trypsin inhibitor (KSTI), a natural serine protease inhibitor.

Experiment 7 (FIG. 7

MG132 is a potent, reversible, and cell-permeable proteasome inhibitor that reduces the degradation of ubiquitin-conjugated proteins in mammalian cells. MG132 is known for its induction of apoptosis and to specifically target cancer cells versus normal cells, although the reasons for this specificity have not been elucidated[23, 24]. Soybean trypsin inhibitor is a natural serine protease inhibitor[25, 26]. It is mentioned as Kunitz soybean trypsin inhibitor (KSTI).

The inventors treated fibroblasts from healthy individuals, from $UV^SS$ and from Cockayne syndrome of type I and II (the last being the more severe), with protease inhibitors MG132 (5 µM) and KSTI (100 µg/ml) for 5 hours and then tested for POLG1 levels. The inventors found that treatment with either MG132 or KSTI resulted in increased levels of POLG1 immunofluorescence in fibroblasts of healthy individuals and of $UV^SS$ (FIG. 7). Significant modifications in two CS type I fibroblasts (539 and 548) were not observed whereas increased levels of POLG1 in the presence of either inhibitors in other CS type I and type II fibroblasts (359, 797, and 816) where POLG1 levels exceeded those of untreated healthy individuals, were found. Moreover, in one case, (177, CS type II), POLG increased to levels of healthy individual after treatment with MG132. The limited increase of POLG1 levels in cells from patient 177 is considered to be interesting, given that these cells do not display an increase in HTRA3 levels either (not shown). Data from cells 177 suggest that their defect may be due to another protease, which is also targeted by protease inhibitors tested here.

Thus, by treatment with protease inhibitors in CS cells it is possible to restore POLG1 levels at least as high as in normal cells. The fact that in two cases the inventors did not observe increase in POLG1 levels suggests that other proteases could be targeted using additional protease inhibitors. HTRA3 may therefore not be the only protease interacting with POLG1, suggesting that treatment aimed at increasing POLG1 levels can be effective through protease inhibitors having a different specificity than only specificity for HTRA3 as a target, in particular protease inhibitors having a large-range specificity. Alternatively, the POLG1 substrate could be improperly modified by other enzymatic activities, or be poorly modified by these activities, so that the protein becomes a poor target for being degraded by HTRA3 or other proteases.

In addition, the inventors also carried out experiments aimed at assessing the relative levels of oxidative stress in Cockayne syndrome (CS) fibroblasts, thereby revealing a preeminent nitroso-redox imbalance in said fibroblasts.

Experiment 8 (FIG. 8

The inventors assessed the relative levels of oxidative stress using the fluorescent probe dichlorofluorescein diacetate (DCFHDA), which prevalently detects reactive oxygen species (ROS)[29]. They reported that whereas $UV^SS$ cells display moderate (25%) increase of signal compared to controls, all CS cells are characterized by higher levels (1.6 to 2-fold) of oxidative stress (FIG. 8a), in agreement with a previous finding[30].

Figure 8A:
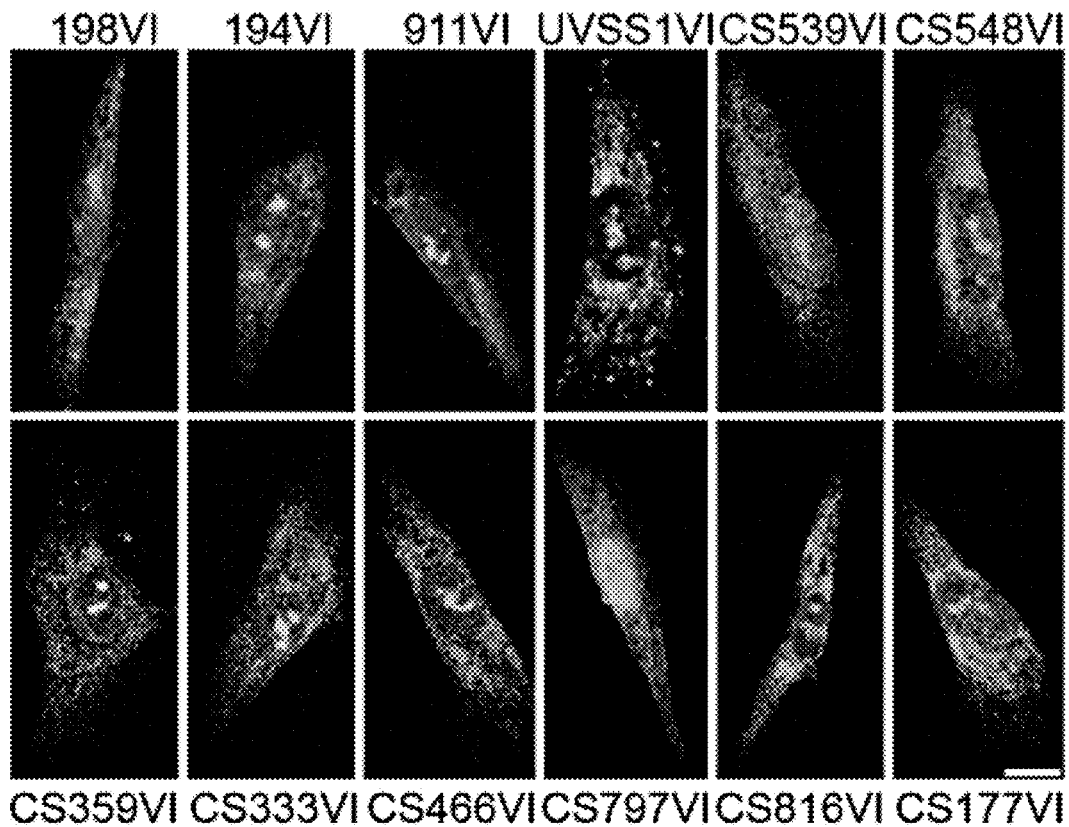
Figure 8A:
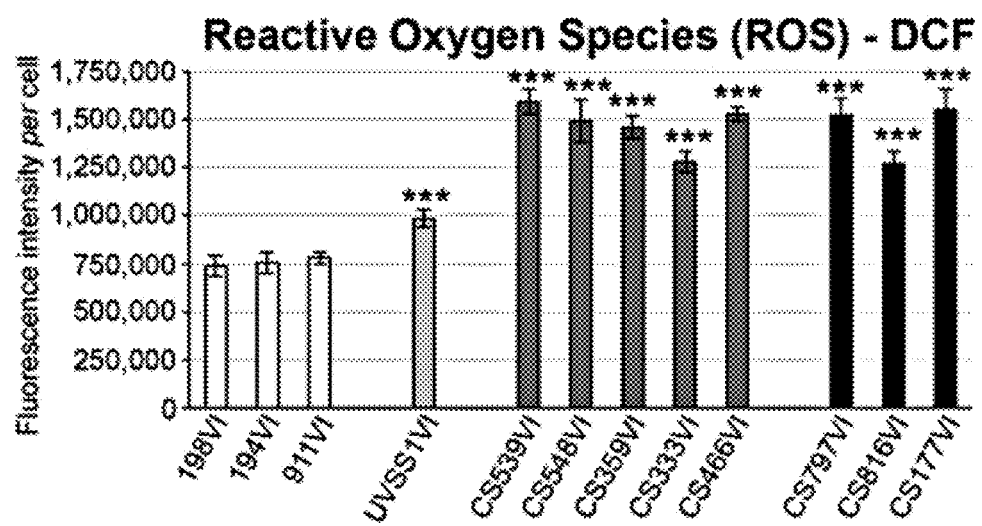
Figure 8B:
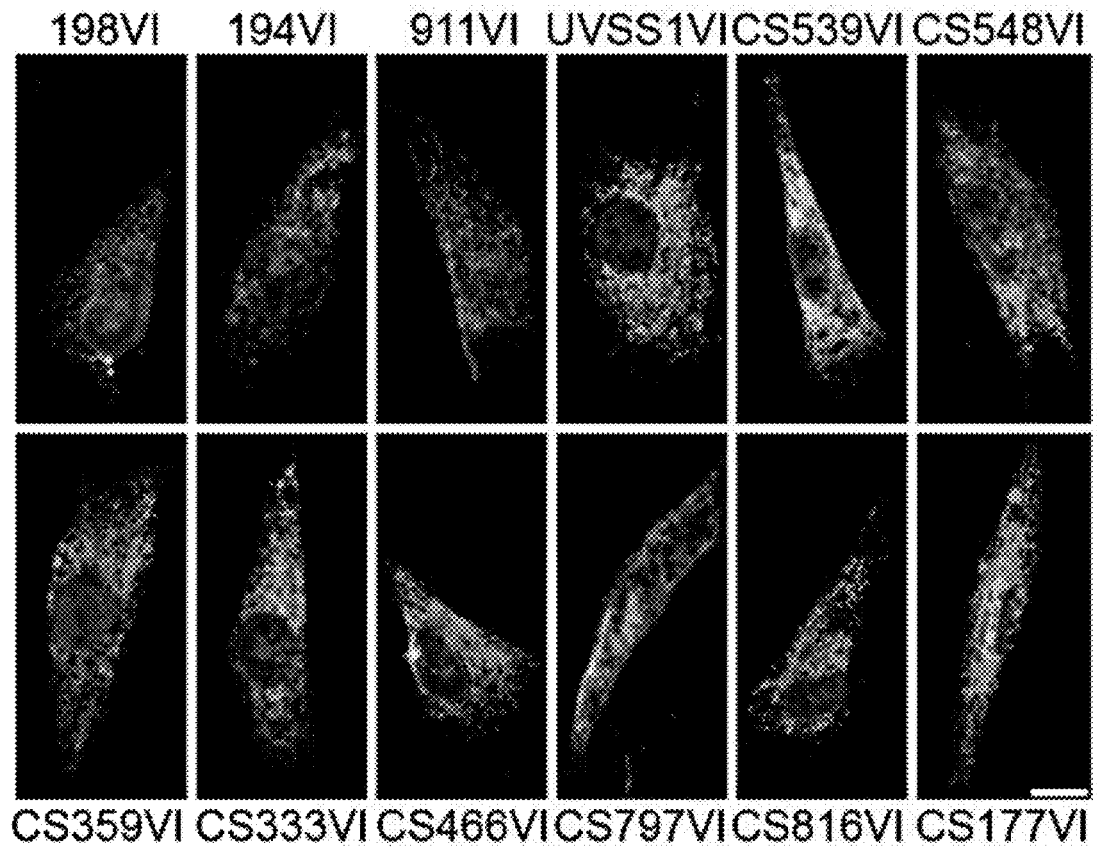
Figure 8B:
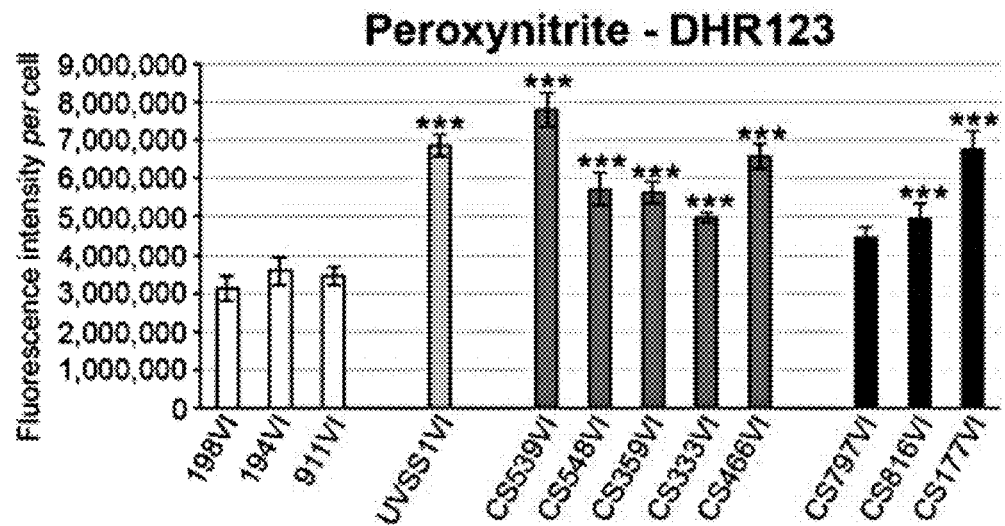

High levels of ROS react with nitric oxide (NO), thereby quenching NO and promoting the formation of peroxynitrite (ONOO$^-$), which is a powerful oxidant and nitration agent[31]. Using the fluorescent probe dihydrorhodamine 123 (DHR123), which selectively detects peroxynitrite[29], the inventors observed that $UV^SS$ and CS cells significantly accumulate peroxynitrite compared to normal fibroblasts (FIG. 8b).

Figure 8C:
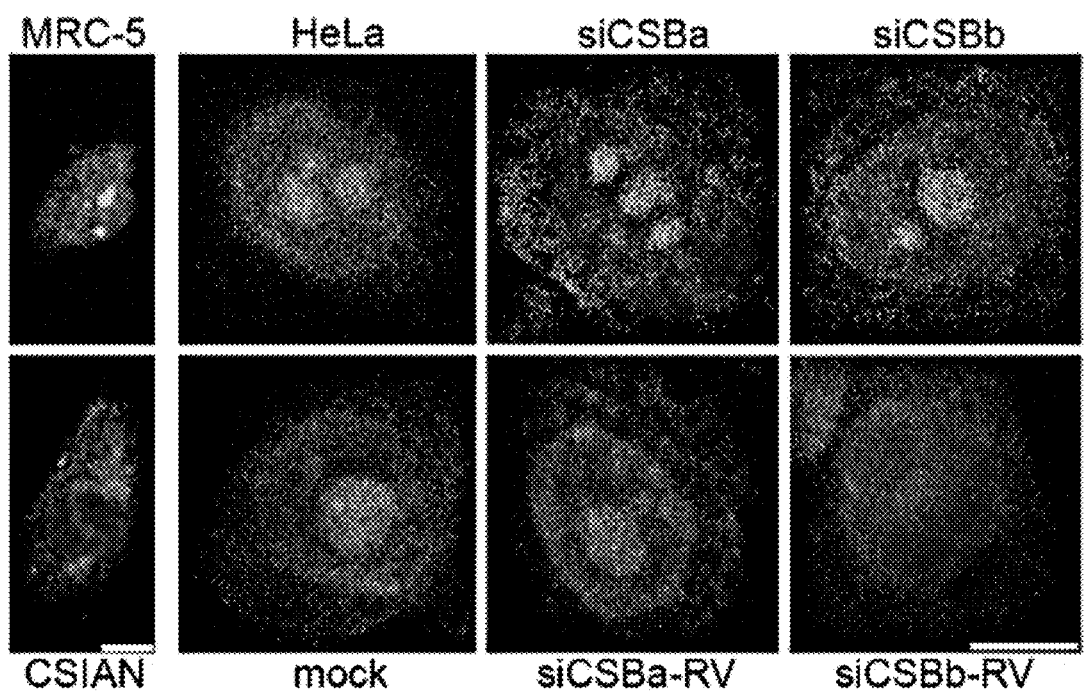
Figure 8C:
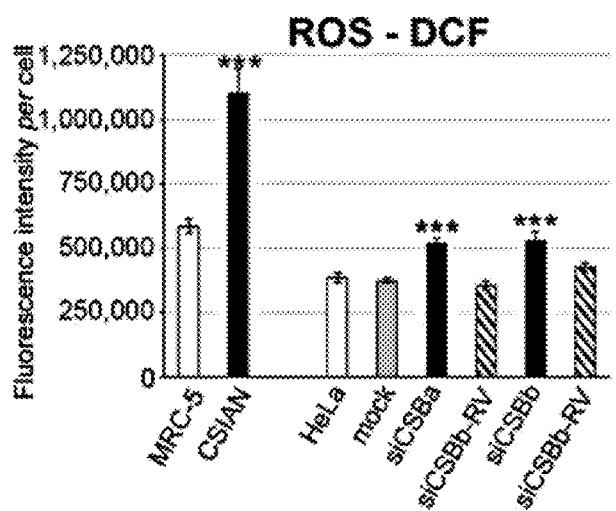
Figure 8D:
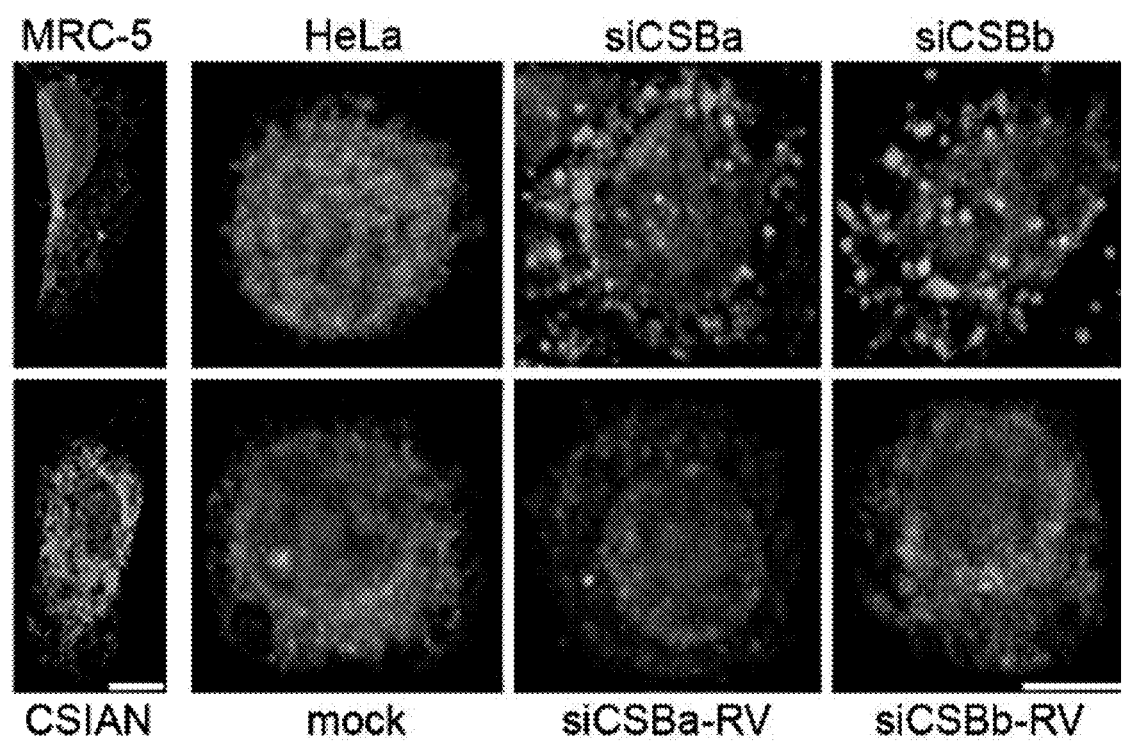
Figure 8D:
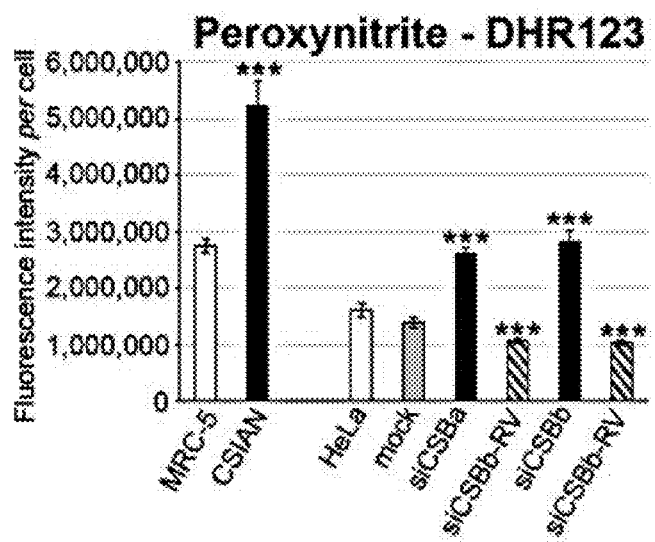

CSB-dependent accumulation of ROS and peroxynitrite was confirmed in CSB-silenced and CSB deficient cells, as well as restoration of CSB-proficient values in cells CSB overexpressing revertants (FIG. 8c,d).

In another experiment, the inventors also showed that ROS and peroxynitrite scavenging rescues altered mitochondrial parameters in fibroblasts from Cockayne Syndrome (CS) patients. By altered mitochondrial parameters, it is in particular meant HTRA2 and/or HTRA3 and/or POLG protein(s) level(s), as illustrated below and in FIG. 9.

Experiment 9 (FIG. 9

Figure 9A:
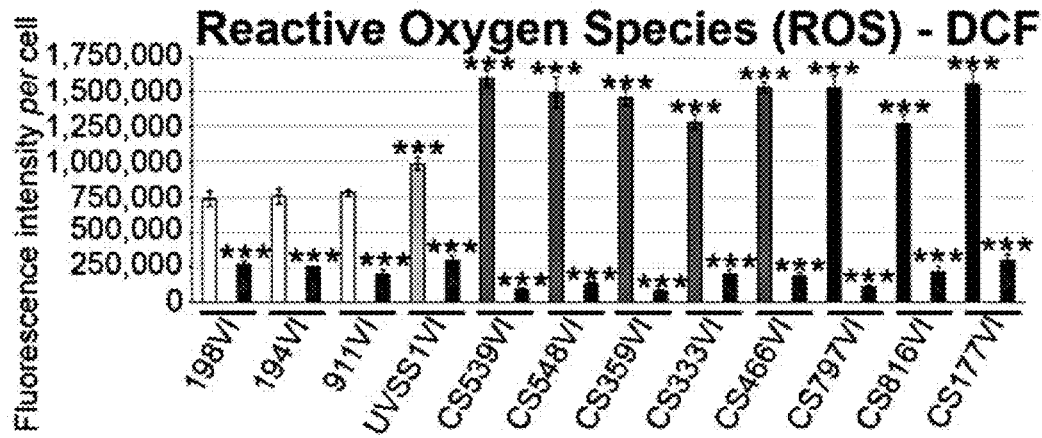
Figure 9B:
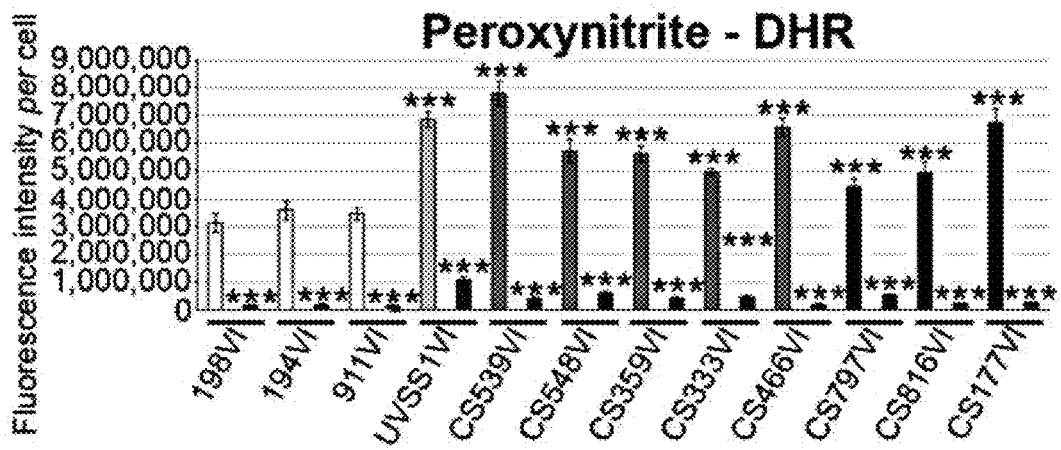
Figure 9C:
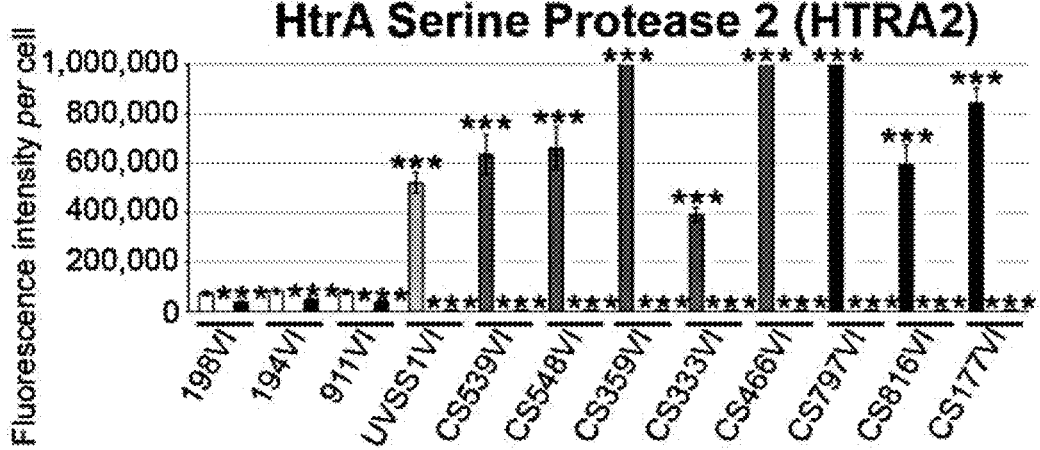
Figure 9D:
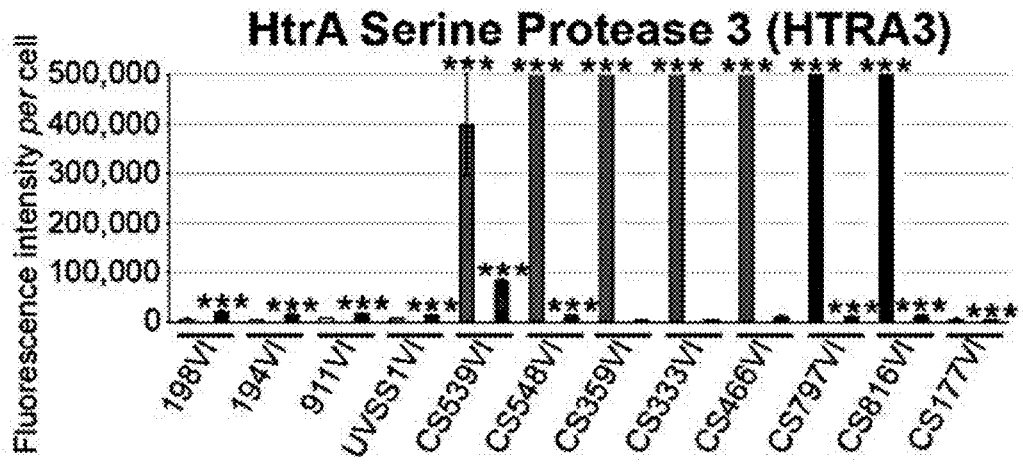
Figure 9E:
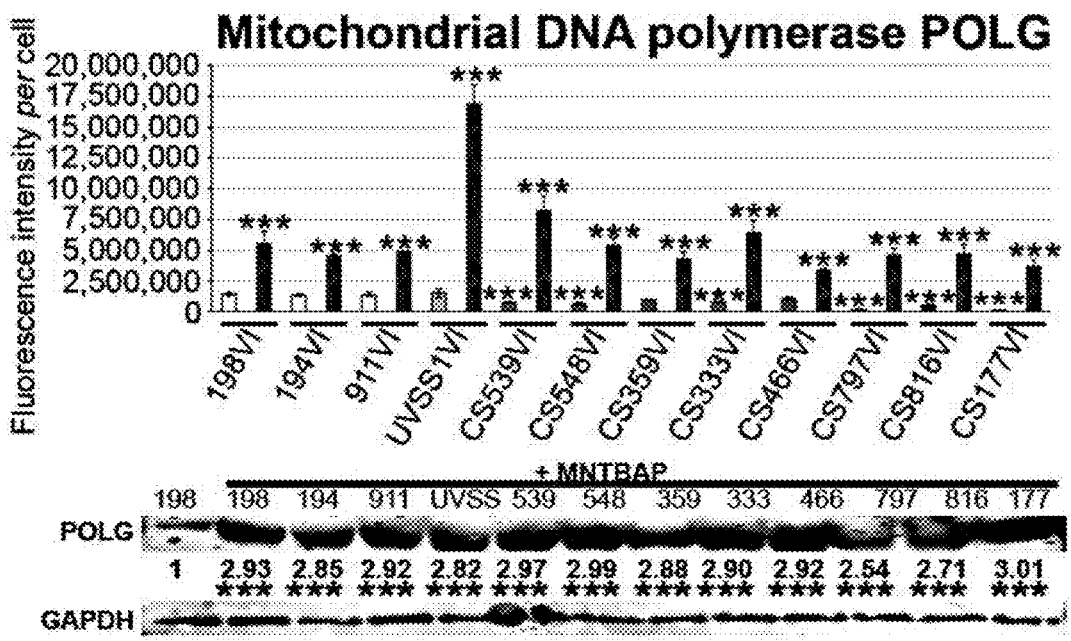
Figure 9F:
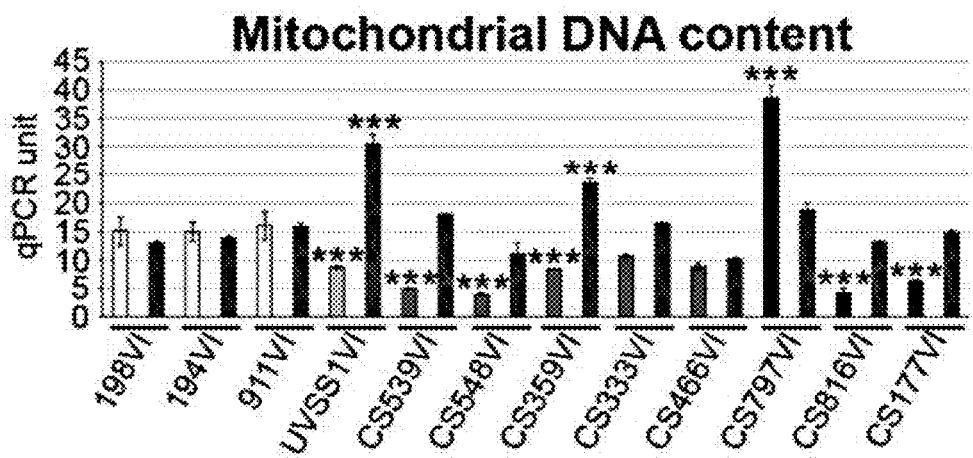

The inventors quantified fluorescence intensities on cells as summarized in Table 1 before and after treatment with MnTBAP (purchased from Millipore) of DCF and of DHR123 per cell (FIGS. 9(a) and (b)), as well as fluorescence intensities of HTRA2 (FIG. 9(c)), HTRA3 (FIG. 9(d)), POLG1 (FIG. 9(e)) per cell. They also evaluated the mtDNA content and ATP levels in cells as summarized in Table 1.

Experiment 10: Resistance to Protease Inhibitor KSTI and MnTBAP of Primary Cells in Culture As KSTI (serine protease inhibitor) and MnTBAP (ROS/RNS scavenger) rescue the CS phenotype by 24 h treatment, the inventors assessed cell survival in culture at longer incubation times with either drug. They used doses of the drugs as those affecting CS cells: 100 µg/ml of KSTI and 100 µM MnTBAP on adult primary fibroblasts IMR-90 and BJ (from ATCC repository). KSTI did not show effect on cell survival (cell number and cell shape) after continuous treatment by 6 days, and MnTBAP by 3 days. Additional experiments are ongoing to test the survival at longer incubation times and lower doses of the drug.

3. CONCLUSIONS AND DISCUSSION: ORIGINALITY OF THE TESTED APPROACH AND EXTENT OF THE INVESTIGATIONS CARRIED OUT

Inventors' data point to a completely new mechanism to explain defects in CS cells, which are also relevant for the process of precocious ageing in other diseases, and also for the process of physiological ageing. Inventors' data do not exclude that DNA repairs alterations take place in these cells, and that these alterations may lead to the symptoms of precocious ageing and tumours. Inventors' data show that cells from patients with CS display dramatically reduced POLG1, the nuclear-coded DNA polymerase that replicates mitochondrial DNA, compared to cells from normal individuals and $UV^SS$ patients (these patients carry a mutation in CSA, as it is the case for several CS patients, the other being mutated in CSB). The inventors thus assume that as a consequence the mtDNA is not properly replicated and thereby mitochondria are dysfunctional, in spite of no apparent modifications in shape and network, compared to cells from normal individuals. Such dysfunction will lead to an increase of oxidative stress, which is essentially produced by mitochondria, likely leading to dysfunctions observed in CS cells. The inventors showed that POLG1 decrease is associated with the CSB mutation as silenced CSB in HeLa cells behave as CS cells in this aspect, and restoration of the regular levels of CSB results in returning (at least) to POLG1 values as in non-silenced cells.

The decrease in POLG1 levels in CS cells is associated with the increase in POLG2, a co-factor of POLG1 that does not contain the catalytic subunit.

The inventors also showed that reduced levels of POLG1 protein, in particular by at least 20% (but not of POLG transcripts that are not affected) are due to increased levels (in particular by at least a 10-folds increase) of HTRA3 (transcript and protein), a serine protease that has POLG1 and other proteins as potential target. Furthermore, by inhibiting HTRA3 with specific (e.g. Soybean trypsin inhibitor (KSTI)), or large-range (e.g. MG-132) inhibitors of proteases the inventors restored normal POLG1 levels in CS cells (from patients) as well as in CSB-silenced HeLa cells.

A. Diagnosis

Inventors' data show that CSA and CSB mutations in cells from Cockayne syndrome patients, and CSB-silencing are associated with decrease of the mitochondrial DNA polymerase POLG1 and with the increase in the accessory factor POLG2. In turn, decrease of POLG1 is associated with dramatic increase in the serine protease HTRA3. POLG1, POLG2 and HTRA3 levels should be considered as markers of Cockayne syndrome and possibly of events of precocious ageing or physiological ageing in general, the symptoms of which are described here above. Indeed, increased levels of HTRA3 or another protease that targets POLG1, generated from misregulation of this protease, which could be also age-driven (in normal subjects), results in decreased levels of POLG1, which in turn induce increased levels of POLG2 to compensate the impairment of the mtDNA replication complex. MtDNA replication is thereby impaired and mitochondria cannot fully ensure their function, leading to progressive dysfunction of the organelle, with reduced ATP production by mitochondria, decreased antioxidative response, and thereby increased oxidative stress, and finally altering global cellular activity, which together leads to the aged cellular and organism phenotype. Moreover, POLG1 mutations that affect the exonuclease activity of the polymerase, which corrects errors produced during DNA synthesis, have also been correlated to ageing phenotype in the literature. Reduced efficiency of mtDNA replication, as in the presence of altered levels of POLG1 and POLG2 could also lead to inefficient accuracy of the mtDNA copy, and therefore contribute to the ageing phenotype.

Mitochondrial dysfunction has been also associated with neurodegenerative diseases as overproduction of oxidative stress is a central feature of all neurodegenerative disorders (Lin et al, 2006, Nature 443: 787-95). Due to their high energy demand, muscle and nerve are the most affected tissue when mitochondrial function is impaired.

The inventors found that cells from CS patients are associated with very low levels of mitochondrial DNA polymerase gamma (POLG), which is responsible for replication of the mitochondrial genome. Levels of POLG1 are not altered in cells of healthy individuals and $UV^SS$ patients. Low levels concern the protein POLG1 and not its transcript, which is produced at regular levels in CS cells. The inventors demonstrated that silencing CSB resulted in low levels of POLG1, thereby linking the levels of this polymerase to CSA and CSB impairment.

They also found that in CS patients lower levels of POLG1 are associated with higher levels of the associated protein POLG2, compared to healthy individuals.

Moreover, they found that decreased levels of POLG1 in CS cells (from patients and after silencing) are associated with higher levels of HTRA3, a serine-protease that has POLG1 as potential target.

Therefore, POLG1, POLG2 protein and HTRA3 protein and transcript levels can be used as distinct markers for the diagnosis of Cockayne syndrome, as well as markers of mitochondrial dysfunctions associated with ageing in general, as described herein, and in neurodegenerative disorders.

B. Therapy Strategy

In the experiments provided herein, the inventors showed that anti-proteases rescue low POLG1 levels. Administration of anti-proteases is therefore a possible therapy for CS patients. It is important to recall here that absolutely no treatment is proposed to these patients, whom maximum life expectancy is around 20 years.

Although functional POLG1 can be detected by sequencing the gene or checking that there is no large mtDNA depletion (as it is the case for pathological POLG1 mutations), POLG1 mutations are associated with severe pathological phenotypes in the child, characterized by various levels of muscle and nerve impairment, but not with precocious ageing. In addition, it is not necessary to be sure that POLG1 is functional for providing a treatment within the context of the invention. Indeed the treatment of the invention can only improve mitochondrial function if POLG1 is functional. Would POLG1 not be functional, a treatment according to the invention would not be efficient.

The inventors found that treating primary fibroblasts with either inhibitor increases the levels of POLG1 in healthy individuals, demonstrating that POLG1 is indeed degraded by a protease that is targeted by MG132 or KSTI.

Importantly, the inventors found that POLG1 levels increase in most of CS cells in the presence of at least one protease inhibitor resulting in POLG1 levels at least as high as in untreated healthy cells.

It is therefore proposed to use protease inhibitors to increase POLG1 levels, whose reduction is a major indication of the CS phenotype, for treating Cockayne syndrome patients, and in particular for targeting the precocious ageing phenotype.

Regarding the ROS imbalance in Cockayne syndrome (CS) fibroblasts, the inventors showed that cells from Cockayne syndrome patients, mutated in CSA or CSB, and CSB-deficient immortalized fibroblasts (CsiAN), as well as CSB-silenced HeLa cells (siCSBA and si CSBb) display high levels of the serine proteases HTRA2 and HTRA3, and in turn low levels of the mitochondrial DNA polymerase POLG. These alterations seem at the base of the mitochondrial impairment observed in CS cells. HTRA3 and POLG levels are not altered in cells from a $UV^SS$ patient (no precocious ageing), which are mutated in CSA. Although it is not clearly elucidated what modulates HTRA3 levels, the inventors postulate, by analogy with HTRA2, whose expression increases in tissues undergoing oxidative stress[27], that HTRA3 expression is also promoted in the presence of stress. CS cells have been reported to accumulate oxidative stress[28]. Alteration of ROS levels may also affect the nitroso-redox balance, as ROS and NO are linked. Nitroso-redox imbalance plays a key role in cell and organ failure, and this could also be the case for the aetiology of CS (Nediani et al, 2011 Antioxidants & Redox signaling 14 (2) 289-331; Takahashi, 2012 J. of Reproduction and Development 58 (1): 1-9; Taverne et al, 2012 J. Appl. Physiol 112: 1644-1652)

Regarding the fact that ROS and peroxynitrite scavenging rescues altered mitochondrial parameters in fibroblasts from Cockayne Syndrome (CS) patients, the inventors reasoned that if Reactive Oxygen Species (ROS) and peroxynitrite induce serine proteases accumulation thereby resulting in POLG depletion, original parameters would be restored in CS fibroblasts treated with ROS and peroxynitrite scavengers.

Manganase(III)tetrakis(4-benzoic acid)porphyrin (MNT-BAP) is a synthetic metalloporphyrin which mimics superoxide dismutase and scavenges ROS and peroxynitrite[32]. Treatment with MNTBAP for 24 h decreased by two thirds the levels of ROS, measured by DCFHDA, in control and $UV^SS$ fibroblasts, confirming the ROS scavenger effect of this molecule (FIG. 9a). Importantly, treatment resulted in decrease of ROS by 80-95% in CS cells. Similarly, MNT-BAP greatly reduced the levels of and peroxynitrite, measured by DHR123, in all control and patient cells (FIG. 9b).

The inventors observed that the ROS and peroxynitrite scavenging action of MNTBAP was able to reduce by one half the levels of serine protease HTRA2 already in control cells. HTRA2 reduction was dramatically higher in $UV^SS$ and all CS cells, which originally displayed elevate levels of this protein (FIG. 9c).

Importantly, MNTBAP increased the levels of HTRA3 in control cells, but did reduce in $UV^SS$ and, to a largest extent in CS cells, where it restored control levels of HTRA3 (FIG. 9d). Thus, overexpression of HTRA3 in CSA/CSB impaired cells is promoted by high ROS and peroxynitrite levels, whereas nitro-oxidative stress represses HTRA3 expression in CSA and CSB proficient fibroblasts.

Scavenging of nitro-oxidative molecules by MNTBAP resulted in increased levels of POLG1 in normal fibroblasts and, to a larger extent $UV^SS$ and CS cells, indicating that patient cells are particularly sensitive to ROS and peroxynitrite levels in the context of POLG1 regulation (FIG. 9e). Moreover, in the presence of MNTBAP the mtDNA content of patient cells becomes close to the value of controls, independently of the original alteration (FIG. 9f): indeed the mtDNA content increases in CS cells with originally low content, and it decreases in CS cells with originally high content. Intriguingly, MNTABP treatment does not change the mtDNA content in control fibroblasts.

Figure 9G:
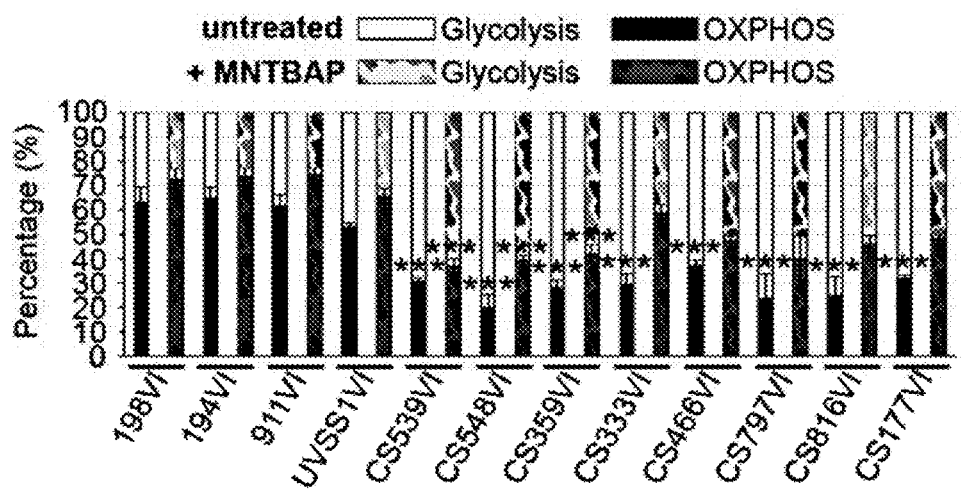
Figure 9H:
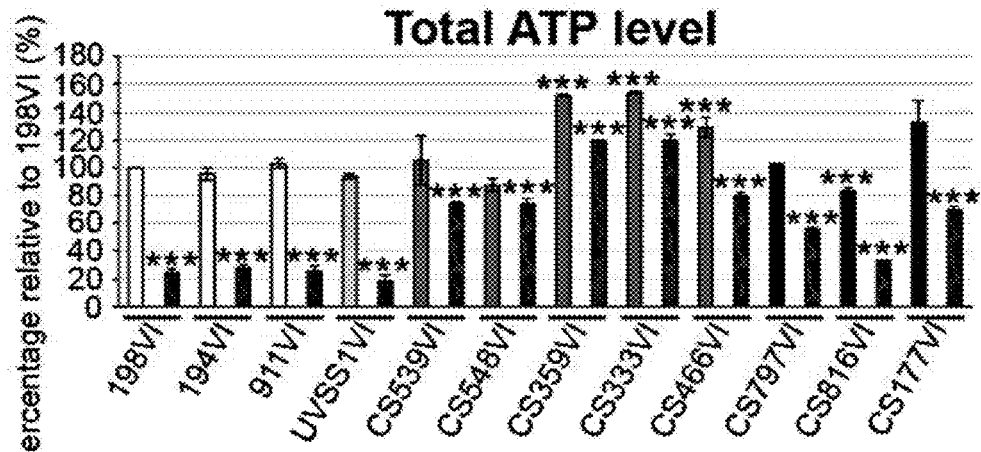

The inventors also observed that the glycolytic shift reported in CS cells is attenuated after 24 h treatment with MNTBAP, increasing the fraction of ATP produced by mitochondria (FIG. 9g). In $UV^SS$ and CS cells, total ATP levels remain relatively high in the presence of MNTABP, whereas control fibroblasts display about 75% reduction compared to untreated cells. These data indicate that scavenging nitro-oxidative molecules has a restoring effect in cells with altered nitroso-redox balance, but may severely alter key parameters in cells with a normal balance.

As a consequence, it is therefore proposed to use MnT-BAP to rescue altered mitochondrial parameters, in particular POLG levels, whose reduction is a major indication of the CS phenotype, and/or use MnTBAP for treating Cockayne syndrome patients.

As a short summary of the inventors' findings and conclusions disclosed herein, it is reminded that data in the literature[30] and inventors' data show that CS cells display increased oxidative stress, and thereby display alteration of the oxidative stress management. Increased oxidative stress results in altered ROS levels, which in turn affects the nitroso-redox balance since these two parameters are linked (Nediani et al, 2011 Antioxidants & Redox signaling 14 (2) 289-331; Takahashi, 2012 J. of Reproduction and Development 58 (1): 1-9; Taverne et al, 2012 J. Appl. Physiol 112: 1644-1652). Also, CSB mutation(s) result(s) in increased ROS levels and POLG1/POLG2/HTRA3 alterations. According to inventors' data, POLG1/POLG2 alterations induce mitochondrial impairment, revealed notably by altered mitochondrial DNA content and altered mitochondrial mass, reduced mitochondrial respiration, which in turn can generate more ROS. Moreover, the inventors consider that there is a relationship between CSB and the regulation of the levels of ROS. Ultimately, CSB mutation(s) increase (s) ROS levels by affecting the expression of ROS-regulating factors. ROS levels also increase because of dysfunctional mitochondria (due to POLG1/POLG2/HTRA3 alterations, as shown by the inventors), which is a fact also dependent of the CSB mutation(s). The combination of these two aspects results in unbalanced ROS levels (and thereby nitroso-redox levels), which act by promoting ageing. Promoting ageing by ROS is part of the largely accepted free radical and mitochondrial theories of ageing, well discussed in the literature[8] (Cui, H., Kong, Y. & Zhang, H. Oxidative stress, mitochondrial dysfunction, and aging. Journal of signal transduction 2012, 646354, doi: 10.1155/2012/646354 (2012)). Therefore, either blocking HTRA3 degradation or scavenging ROS by MnTBAP results in reducing ROS levels, thereby restoring «normal» conditions (restoring mitochondrial function).

Since it is possible that the defects observed and discussed herein with respect to the CS phenotype may appear, although at a minor extent, also during normal (physiological) ageing, the treatment(s) described herein may also be considered in the context of preventive or prophylactic therapies. According to a particular embodiment, all the methods described herein are used for preventive or prophylactic purpose.

Acronyms used within the present disclosure: Ataxia telangiectasia (A-T); Base excision repair (BER); Bloom syndrome (BS); Cockayne syndrome (CS); DNA polymerase gamma (POLG1); DNA polymerase subunit gamma-2 (POLG2); Double strand break repair (DSB); Global genome NER (GG-NER); Fanconi anemia (FA); High-temperature requirement factor A2 (HTRA2); High-temperature requirement factor A3 (HTRA3); Hutchinson-Guilford progeria syndrome (HGPS); Kunitz Soybean trypsin inhibitor (KSTI); Manganese (III) tetrakis (4-benzoic acid)porphyrin (MnaTBP); Mitochondrial transcription factor A (TFAM); Nucleotide excision repair (NER); Rothmund-Thomson syndrome (RTS); Reactive oxygen species (ROS); Spontaneous sister chromatid exchanges (SCE); Transcription-coupled NER (TC-NER also called TCR); Trichothiodystropy (TTD); Xeroderma Pigmentosum (XP); Werner syndrome (WS)

REFERENCES

1. Nance M A, Berry S A. Cockayne syndrome: review of 140 cases. *American journal of medical genetics* 1992, 42(1): 68-84.
2. Kleijer W J, Laugel V, Berneburg M, Nardo T, Fawcett H, Gratchev A, et al. Incidence of DNA repair deficiency disorders in western Europe: Xeroderma pigmentosum, Cockayne syndrome and trichothiodystrophy. *DNA repair* 2008, 7(5): 744-750.
3. Henning K A, Li L, Iyer N, McDaniel L D, Reagan M S, Legerski R, et al. The Cockayne syndrome group A gene encodes a WD repeat protein that interacts with CSB protein and a subunit of RNA polymerase II TFIIH. *Cell* 1995, 82(4): 555-564.
4. Troelstra C, van Gool A, de Wit J, Vermeulen W, Bootsma D, Hoeijmakers J H. ERCC6, a member of a subfamily of putative helicases, is involved in Cockayne's syndrome and preferential repair of active genes. *Cell* 1992, 71(6): 939-953.
5. Laugel V, Dalloz C, Durand M, Sauvanaud F, Kristensen U, Vincent M C, et al. Mutation update for the CSB/ERCC6 and CSA/ERCC8 genes involved in Cockayne syndrome. *Human mutation* 2010, 31(2): 113-126.
6. Ganesan A, Spivak G, Hanawalt P C. Transcription-coupled DNA repair in prokaryotes. *Progress in molecular biology and translational science* 2012, 110: 25-40.
7. Velez-Cruz R, Egly J M. Cockayne syndrome group B (CSB) protein: at the crossroads of transcriptional networks. *Mechanisms of ageing and development* 2013, 134 (5-6): 234-242.
8. Khobta A, Epe B. Repair of oxidatively generated DNA damage in Cockayne syndrome. *Mechanisms of ageing and development* 2013, 134 (5-6): 253-260.
9. Aamann M D, Sorensen M M, Hvitby C, Berquist B R, Muftuoglu M, Tian J, et al. Cockayne syndrome group B protein promotes mitochondrial DNA stability by supporting the DNA repair association with the mitochondrial membrane. *FASEB journal: official publication of the Federation of American Societies for Experimental Biology* 2010, 24(7): 2334-2346.
10. Kamenisch Y, Fousteri M, Knoch J, von Thaler A K, Fehrenbacher B, Kato H, et al. Proteins of nucleotide and base excision repair pathways interact in mitochondria to protect from loss of subcutaneous fat, a hallmark of aging. *The Journal of experimental medicine* 2010, 207(2): 379-390.
11. Nardo T, Oneda R, Spivak G, Vaz B, Mortier L, Thomas P, et al. A UV-sensitive syndrome patient with a specific CSA mutation reveals separable roles for CSA in response to UV and oxidative DNA damage. *Proceedings of the National Academy of Sciences of the U.S. Pat. No. 2,009*, 106(15): 6209-6214.
12. Lehmann A R. DNA repair-deficient diseases, xeroderma pigmentosum, Cockayne syndrome and trichothiodystrophy. *Biochimie* 2003, 85(11): 1101-1111.
13. Kamenisch Y, Berneburg M. Progeroid syndromes and UV-induced oxidative DNA damage. *The journal of investigative dermatology Symposium proceedings/the Society for Investigative Dermatology, Inc [and] European Society for Dermatological Research* 2009, 14(1): 8-14.
14. Hofer A C, Tran R T, Aziz O Z, Wright W, Novelli G, Shay J, et al. Shared phenotypes among segmental progeroid syndromes suggest underlying pathways of aging. *The journals of gerontology Series A, Biological sciences and medical sciences* 2005, 60(1): 10-20.
15. Coppede F. Premature aging syndrome. *Advances in experimental medicine and biology* 2012, 724: 317-331.
16. Killoran M P, Keck J L. Sit down, relax and unwind: structural insights into RecQ helicase mechanisms. *Nucleic acids research* 2006, 34(15): 4098-4105.
17. Stumpf J D, Copeland W C. Mitochondrial DNA replication and disease: insights from DNA polymerase gamma mutations. *Cellular and molecular life sciences: CMLS* 2011, 68(2): 219-233.
18. Cui, H., Kong, Y. & Zhang, H. Oxidative stress, mitochondrial dysfunction, and aging. Journal of signal transduction 2012, 646354, doi: 10.1155/2012/646354 (2012).
19. Biard, D. S. Untangling the relationships between DNA repair pathways by silencing more than 20 DNA repair genes in human stable clones. Nucleic acids research 35, 3535-3550, doi: 10.1093/nar/gkm 195 (2007).
20. Lim, S. E., Longley, M. J. & Copeland, W. C. The mitochondrial p55 accessory subunit of human DNA polymerase gamma enhances DNA binding, promotes processive DNA synthesis, and confers N-ethylmaleimide resistance. The Journal of biological chemistry 274, 38197-38203 (1999).
21. Bovvden, M. A. et al. High-temperature requirement factor A3 (Htra3): a novel serine protease and its potential role in ovarian function and ovarian cancers. Molecular and cellular endocrinology 327, 13-18, doi: 10.1016/j.mce.2010.06.001 (2010).
22. Dynon, K. et al. HTRA3 as an early marker for preeclampsia: specific monoclonal antibodies and sensitive high-throughput assays for serum screening. PloS one 7, e45956, doi: 10.1371/journal.pone.0045956 (2012).
23. Gartel, A. L. A new target for proteasome inhibitors: FoxM1. Expert opinion on investigational drugs 19, 235-242, doi: 10.1517/13543780903563364 (2010).

24. Shah, J. J. & Orlowski, R. Z. Proteasome inhibitors in the treatment of multiple myeloma. *Leukemia* 23, 1964-1979, doi: 10.1038/leu.2009.173 (2009).
25. Kunitz, M. Crystallization of a Trypsin Inhibitor from Soybean. *Science* 101, 668-669, doi: 10.1126/science.101.2635.668 (1945).
26. Papastoitsis, G. & Wilson, K. A. Initiation of the degradation of the soybean kunitz and bowman-birk trypsin inhibitors by a cysteine protease. *Plant physiology* 96, 1086-1092 (1991).
27. Ding, X. et al. Enhanced HtrA2/Omi expression in oxidative injury to retinal pigment epithelial cells and murine models of neurodegeneration. *Investigative ophthalmology &visual science* 50, 4957-4966, doi:10.1167/iovs.09-3381 (2009).
28. Pascucci, B. et al. An altered redox balance mediates the hypersensitivity of Cockayne syndrome primary fibroblasts to oxidative stress. *Aging Cell* 11, 520-529, doi: 10.1111/j.1474-9726.2012.00815.x (2012).
29. Deng, T., Xu, K., Zhang, L. & Zheng, X. Dynamic determination of Ox-LDL-induced oxidative/nitrosative stress in single macrophage by using fluorescent probes. *Cell biology international* 32, 1425-1432, doi:10.1016/j.cellbi.2008.08.013 (2008).
30. Nardo, T. et al. A UV-sensitive syndrome patient with a specific CSA mutation reveals separable roles for CSA in response to UV and oxidative DNA damage. *Proc Natl Acad Sci USA* 106, 6209-6214, doi:0902113106 [pii] 10.1073/pnas.0902113106 (2009).
31. Wink, D. A., & Mitchell J. B. Chemical biology of nitric oxide: Insights into regulatory, cytotoxic, and cytoprotective mechnaisms of nitric oxide. *Free Radic. Biol. Med.* 25, 436-56 (1998)
32. Batinic-Haberle, I. et al. Pure MnTBAP selectively scavenges peroxynitrite over superoxide: comparison of pure and commercial MnTBAP samples to MnTE-2-PyP in two models of oxidative stress injury, an SOD-specific *Escherichia coli* model and carrageenan-induced pleurisy. *Free Radic Biol Med* 46, 192-201, doi:10.1016/j.freeradbiomed.2008.09.042 (2009).

The invention claimed is:

1. A method to treat cockayne syndrome in a patient comprising, having determined that the patient has reduced levels of POLG1 compared to a healthy control and/or increased levels of HTRA2 compared to a healthy control and/or increased levels HTRA3 compared to a healthy control, administering to the patient at least one nitroso-redox stress scavenger compound and/or at least one protease inhibitor.

2. The method of claim 1, wherein the nitroso-redox stress scavenger compound scavenges both amongst reactive oxygen species (ROS) and reactive nitrogen species (RNS).

3. The method of claim 1, wherein the nitroso-redox stress scavenger compound is a manganese porphyrin.

4. The method according to claim 1, wherein the at least one nitroso-redox stress scavenger compound is selected from:

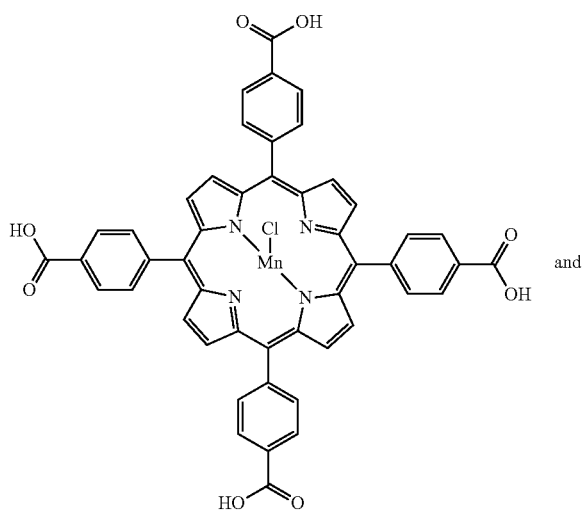

and

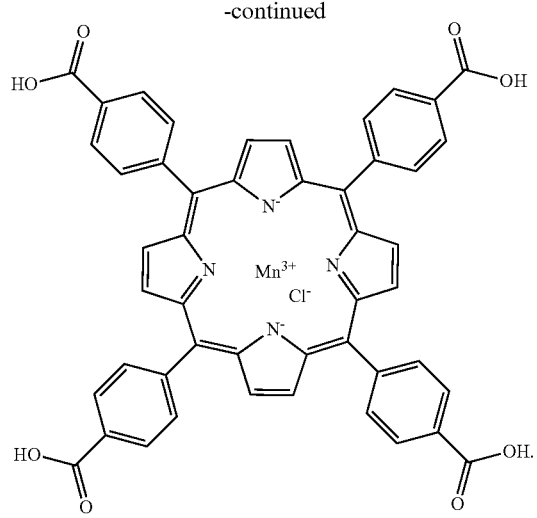

5. The method according to claim 1, further comprising the steps of:
   a. contacting a biological sample from the patient with at least one marker specific for at least one species selected in the group of: POLG1 protein, HTRA3 protein, HTRA2 protein, or any combination of these species, in conditions enabling said marker(s) to react with their respective targets, and
   b. determining the level of at least one species selected in step a) from the group of: POLG1 protein, HTRA3 protein, HTRA2 protein, or any combination of these species in said biological sample through measurement of the marker(s) that has(have) reacted with its (their) respective species in step a), or through measurement of the reaction product(s) obtained after reacting the marker(s) with its (their) respective species in step a), and
   c. comparing the level(s) determined in step b) with respective normal threshold value(s) determined for healthy subject(s) for each species selected in the group set forth in step a) and b) to carry out said steps, and
   d. from the comparison made in step c), concluding about the existence of a dysfunction in mtDNA replication.

6. The method of claim 1, comprising administering to the patient a protease inhibitor which interacts with protease(s) degrading POLG1 in combination with a nitroso-redox stress scavenger compound.

7. The method according to claim 6, wherein the protease inhibitor is administered before the nitroso-redox stress scavenger.

8. The method according to claim 6, wherein the protease inhibitor is administered after the nitroso-redox stress scavenger.

\* \* \* \* \*